United States Patent
Moon et al.

(10) Patent No.: US 10,636,980 B2
(45) Date of Patent: *Apr. 28, 2020

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD, Chungcheongnam-do (KR)

(72) Inventors: Doo-Hyeon Moon, Gyeonggi-do (KR); Ji-Song Jun, Gyeonggi-do (KR)

(73) Assignee: Rohm and Haas Electronic Materials Korea Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/315,178

(22) PCT Filed: Jul. 27, 2017

(86) PCT No.: PCT/KR2017/008083
§ 371 (c)(1),
(2) Date: Jan. 4, 2019

(87) PCT Pub. No.: WO2018/021841
PCT Pub. Date: Feb. 1, 2018

(65) Prior Publication Data
US 2019/0312212 A1    Oct. 10, 2019

(30) Foreign Application Priority Data

Jul. 27, 2016 (KR) .................. 10-2016-0095622
Jul. 26, 2017 (KR) .................. 10-2017-0094723

(51) Int. Cl.
| | | |
|---|---|---|
| *C07D 487/06* | (2006.01) | |
| *C07D 487/16* | (2006.01) | |
| *C07D 487/22* | (2006.01) | |
| *C09K 11/02* | (2006.01) | |
| *C09K 11/06* | (2006.01) | |
| *H01L 51/00* | (2006.01) | |
| *C09B 57/00* | (2006.01) | |
| *H01L 51/50* | (2006.01) | |

(52) U.S. Cl.
CPC ........ *H01L 51/0072* (2013.01); *C07D 487/16* (2013.01); *C07D 487/22* (2013.01); *C09B 57/00* (2013.01); *C09K 11/06* (2013.01); *H01L 51/0067* (2013.01); *C09K 2211/1018* (2013.01); *H01L 51/0059* (2013.01); *H01L 51/5016* (2013.01); *H01L 51/5056* (2013.01)

(58) Field of Classification Search
CPC .. C07D 487/06; C07D 487/16; C07D 487/22; C09K 11/02; C09K 11/06; H01L 51/00
See application file for complete search history.

(56) References Cited

U.S. PATENT DOCUMENTS

| | | |
|---|---|---|
| 2016/0163998 A1 | 6/2016 | Saito et al. |
| 2018/0223184 A1 | 8/2018 | Moon et al. |
| 2018/0337340 A1 | 11/2018 | Moon |

FOREIGN PATENT DOCUMENTS

| | | |
|---|---|---|
| KR | 2015-0077220 A | 7/2015 |
| WO | 2016/080791 A1 | 5/2016 |

*Primary Examiner* — Brenda L Coleman
(74) *Attorney, Agent, or Firm* — S. Mathew Cairns

(57) ABSTRACT

The present disclosure relates to an organic electroluminescent compound and an organic electroluminescent device comprising the same. By using the organic electroluminescent compound of the present disclosure, an organic electroluminescent device having low driving voltage, high luminous efficiency, and or excellent lifespan characteristic can be produced.

10 Claims, 1 Drawing Sheet

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

Among display devices, an electroluminescent device (EL device) is a self-light-emitting device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

The most important factor determining luminous efficiency in an organic electroluminescent device is light-emitting materials. Until now, fluorescent materials have been widely used as a light-emitting material. However, in view of electroluminescent mechanisms, since phosphorescent light-emitting materials theoretically enhance luminous efficiency by four (4) times compared to fluorescent light-emitting materials, development of phosphorescent light-emitting materials are widely being researched. To date, iridium(III) complexes have been widely known as phosphorescent materials, including bis(2-(2'-benzothienyl)-pyridinato-N,C3')iridium(acetylacetonate) ((acac)Ir(btp)2), tris(2-phenylpyridine)iridium (Ir(ppy)$_3$) and bis(4,6-difluorophenylpyridinato-N,C2)picolinate iridium (Firpic) as red, green, and blue materials, respectively.

At present, 4,4'-N,N'-dicarbazol-biphenyl (CBP) is the most widely known phosphorescent host material. Recently, Pioneer (Japan) et al. developed a high performance organic electroluminescent device using bathocuproine (BCP) and aluminum(III)bis(2-methyl-8-quinolinate)(4-phenylphenolate) (BAlq) etc., which were used as hole blocking layer materials, as host materials.

Although these materials provide good light-emitting characteristics, they have the following disadvantages: (1) Due to their low glass transition temperature and poor thermal stability, their degradation may occur during a high-temperature deposition process in a vacuum, and the lifespan of the device decreases. (2) The power efficiency of an organic electroluminescent device is given by [(π/voltage)×current efficiency], and the power efficiency is inversely proportional to the voltage. Although an organic electroluminescent device comprising phosphorescent host materials provides higher current efficiency (cd/A) than one comprising fluorescent materials, a significantly high driving voltage is necessary. Thus, there is no merit in terms of power efficiency (lm/W). (3) Further, when these materials are used in an organic electroluminescent device, the operational lifespan of an organic electroluminescent device is short and luminous efficiency is still required to be improved.

In order to enhance luminous efficiency, driving voltage and/or lifespan, various materials or concepts for an organic layer of an organic electroluminescent device have been proposed. However, they were not satisfactory to use practically.

Korean Patent Appln. Laying-Open No. KR 2015-0077220 discloses a compound of a fused structure comprising a carbazole and an azepine as a compound for an organic electroluminescent device. However, said reference does not specifically disclose a compound of a fused structure comprising an indolocarbazole and an azepine.

DISCLOSURE OF THE INVENTION

Problems to be Solved

The objective of the present disclosure is to provide i) an organic electroluminescent compound which can produce an organic electroluminescent device having low driving voltage, high luminous efficiency, and/or excellent lifespan characteristic, and ii) an organic electroluminescent device comprising the compound.

Solution to Problems

As a result of intensive studies to solve the technical problem above, the present inventors found that the above objective can be achieved by an organic electroluminescent compound represented by the following formula 1:

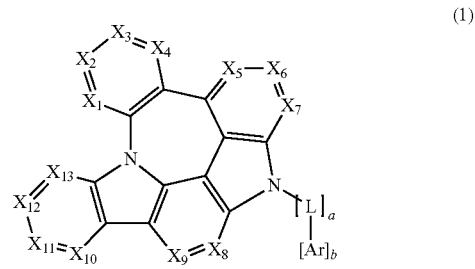

wherein $X_1$ to $X_{13}$ each independently represent N or $CR_1$;

L represents a single bond, a substituted or unsubstituted (C1-C30)alkylene, a substituted or unsubstituted (C6-C30) arylene, a substituted or unsubstituted 3- to 30-membered heteroarylene, or a substituted or unsubstituted (C3-C30) cycloalkylene;

Ar and $R_1$ each independently represent hydrogen, deuterium, a halogen, a cyano, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or are linked to an adjacent substituent to form a substituted or unsubstituted, mono- or polycyclic, (C3-C30) alicyclic or aromatic ring, whose carbon atom(s) may be replaced with at least one heteroatom selected from nitrogen, oxygen, and sulfur;

the heteroaryl(ene) contains at least one heteroatom selected from B, N, O, S, Si, and P; and a and b each independently represent an integer of 1 to 2.

EFFECTS OF THE INVENTION

By using the organic electroluminescent compound according to the present disclosure, an organic electroluminescent device having low driving voltage, high luminous efficiency, and/or excellent lifespan characteristic can be produced.

BRIEF DESCRIPTIONS OF THE FIGURES

The FIGURE shows that the compound according to the present disclosure has a reduced steric hindrance compared to a conventional compound.

EMBODIMENTS OF THE INVENTION

Hereinafter, the present disclosure will be described in detail. However, the following description is intended to explain the disclosure, and is not meant in any way to restrict the scope of the disclosure.

The present disclosure relates to an organic electroluminescent compound represented by formula 1, an organic electroluminescent material comprising the compound, and an organic electroluminescent device comprising the material.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. The compound represented by formula 1 may be comprised in at least one layer constituting an organic electroluminescent device, and may be comprised in a light-emitting layer, but is not limited thereto. When comprised in the light-emitting layer, it can be comprised as a phosphorescent host material.

Hereinafter, the organic electroluminescent compound represented by formula 1 will be described in detail.

The compound of formula 1 may be represented by any one of the following formulas 2 to 7:

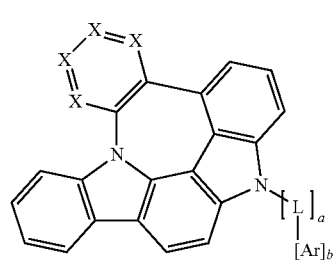

(2)

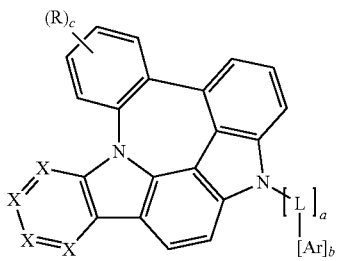

(3)

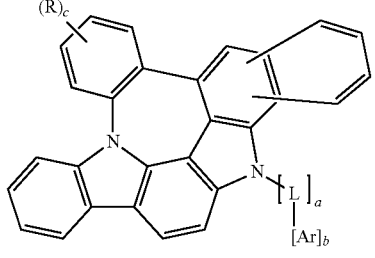

(4)

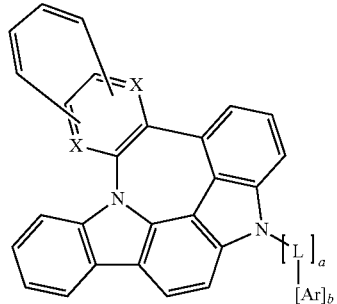

(5)

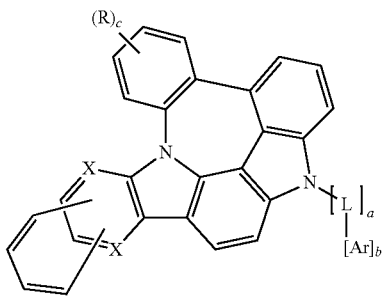

(6)

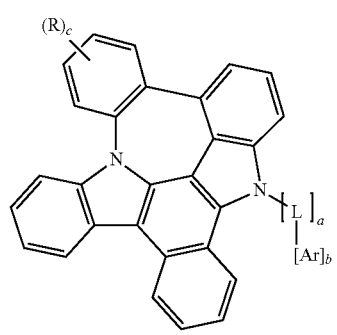

(7)

wherein

X represents N or $CR_1$;

R represents a substituted or unsubstituted mono- or di-(C6-C30)arylamino;

c represents an integer of 1 to 2; and

L, Ar, $R_1$, a, and b are as defined in formula 1.

Herein, "(C1-C30)alkyl(ene)" is meant to be a linear or branched alkyl(ene) having 1 to 30 carbon atoms, in which the number of carbon atoms is preferably 1 to 10, more preferably 1 to 6, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl(ene)" is meant to be a mono- or polycyclic hydrocarbon having 3 to 30 carbon atoms, in which the number of carbon atoms is preferably 3 to 20, more preferably 3 to 7, and includes cyclopropyl, cyclobutyl, cyclopentyl, cyclohexyl, etc. "3- to 7-membered heterocycloalkyl" is meant to be a cycloalkyl having at least one heteroatom selected from the group consisting of B, N, O, S, Si, and P, preferably O, S, and N, and 3 to 7 ring backbone atoms, and includes tetrahydrofuran, pyrrolidine, thiolan, tetrahydropyran, etc. "(C6-C30)aryl(ene)" is meant to be a monocyclic or fused ring radical derived from an aromatic hydrocarbon having 6 to 30 ring backbone carbon atoms, in which the number of ring backbone carbon atoms is preferably 6 to 20, more preferably 6 to 15, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc. "3- to 30-membered heteroaryl(ene)" is meant to be an aryl group having at least one, preferably 1 to 4 heteroatoms selected from the group consisting of B, N, O, S, Si, and P, and 3 to 30 ring backbone atoms; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, benzoquinazolinyl, quinoxalinyl, benzoquinoxalinyl, carbazolyl, benzocarbazolyl, phenoxazinyl, phenanthridinyl, benzodioxolyl, etc. "Halogen" includes F, Cl, Br, and I.

Herein, "substituted" in the expression "substituted or unsubstituted" means that a hydrogen atom in a certain functional group is replaced with another atom or functional group, i.e., a substituent. The substituents of the substituted (C1-C30)alkyl(ene), the substituted (C6-C30)aryl(ene), the substituted 3- to 30-membered heteroaryl(ene), the substituted (C3-C30)cycloalkyl(ene), the substituted (C1-C30) alkoxy, the substituted tri(C1-C30)alkylsilyl, the substituted di(C1-C30)alkyl(C6-C30)arylsilyl, the substituted (C1-C30) alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted mono- or polycyclic, (C3-C30) alicyclic or aromatic ring in Ar, L, and $R_1$ each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl unsubstituted or substituted with a (C6-C30)aryl, a (C6-C30)aryl unsubstituted or substituted with a 5- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30) arylamino unsubstituted or substituted with a (C1-C30) alkyl, a (C1-C30)alkyl(C6-C30)arylamino, a (C1-C30)alkylcarbonyl, a (C1-C30)alkoxycarbonyl, a (C6-C30) arylcarbonyl, a di(C6-C30)arylboronyl, a di(C1-C30) alkylboronyl, a (C1-C30)alkyl(C6-C30)arylboronyl, a (C6-C30)aryl(C1-C30)alkyl, and a (C1-C30)alkyl(C6-C30)aryl; and preferably each independently are at least one selected from the group consisting of a (C1-C6)alkyl; a (C6-C25)aryl unsubstituted or substituted with a (C1-C6)alkyl or a (C6-C12)aryl; a 5- to 20-membered heteroaryl unsubstituted or substituted with a (C6-C12)aryl; and a (C1-C6)alkyl (C6-C12)aryl.

In formula 1 above, $X_1$ to $X_{13}$ each independently represent N or $CR_1$.

L represents a single bond, a substituted or unsubstituted (C1-C30)alkylene, a substituted or unsubstituted (C6-C30) arylene, a substituted or unsubstituted 3- to 30-membered heteroarylene, or a substituted or unsubstituted (C3-C30) cycloalkylene, preferably represents a single bond, a substituted or unsubstituted (C6-C15)arylene, or a substituted or unsubstituted 5- to 15-membered heteroarylene, and more preferably represents a single bond, an unsubstituted (C6-C15)arylene, or an unsubstituted 5- to 15-membered heteroarylene.

Ar and $R_1$ each independently represent hydrogen, deuterium, a halogen, a cyano, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or are linked to an adjacent substituent to form a substituted or unsubstituted, mono- or polycyclic, (C3-C30) alicyclic or aromatic ring, whose carbon atom(s) may be replaced with at least one heteroatom selected from nitrogen, oxygen, and sulfur. Ar preferably represents hydrogen, a substituted or unsubstituted (C6-C20)aryl, a substituted or unsubstituted 5- to 20-membered heteroaryl, or a substituted or unsubstituted di(C6-C15)arylamino; and more preferably represents hydrogen, an unsubstituted (C6-C20)aryl, a 5- to 20-membered heteroaryl unsubstituted or substituted with a (C1-C6)alkyl, a (C6-C25)aryl, a 5- to 20-membered heteroaryl, or a (C1-C6)alkyl(C6-C15)aryl, or an unsubstituted di(C6-C15)arylamino. $R_1$ preferably represents hydrogen, or a substituted or unsubstituted di(C6-C15)arylamino; or is linked to an adjacent substituent to form a substituted or unsubstituted, mono- or polycyclic, (C3-C15) alicyclic or aromatic ring, whose carbon atom(s) may be replaced with at least one heteroatom selected from nitrogen, oxygen, and sulfur; and more preferably represents hydrogen, or a di(C6-C15)arylamino unsubstituted or substituted with a (C1-C6)alkyl; or is linked to an adjacent substituent to form an unsubstituted monocyclic (C3-C15) aromatic ring, for example, a benzene ring.

Specifically, Ar may be a substituted or unsubstituted phenyl, a substituted or unsubstituted naphthyl, a substituted or unsubstituted biphenyl, a substituted or unsubstituted terphenyl, a substituted or unsubstituted triazinyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted dibenzothiophenyl, a substituted or unsubstituted benzothiophenyl, a substituted or unsubstituted dibenzofuranyl, or a substituted or unsubstituted benzofuranyl. More specifically, Ar may be a triazinyl, pyrimidinyl, quinazolinyl, benzoquinazolinyl, quinoxalinyl, benzoquinoxalinyl, quinolyl, benzoquinolyl, isoquinolyl, benzoisoquinolyl, triazolyl, pyrazolyl, dibenzothiophenyl, benzothiophenyl, dibenzofuranyl, or benzofuranyl, substituted with an aryl or a heteroaryl.

According to one embodiment of the present disclosure, in formula 1 above, $X_1$ to $X_{13}$ each independently represent N or $CR_1$; L represents a single bond, a substituted or unsubstituted (C6-C15)arylene, or a substituted or unsubstituted 5- to 15-membered heteroarylene; Ar represents hydrogen, a substituted or unsubstituted (C6-C20)aryl, a substituted or unsubstituted 5- to 20-membered heteroaryl, or a substituted or unsubstituted di(C6-C15)arylamino; and $R_1$ represents hydrogen, or a substituted or unsubstituted di(C6-C15)arylamino; or is linked to an adjacent substituent to form a substituted or unsubstituted, mono- or polycyclic, (C3-C15) alicyclic or aromatic ring, whose carbon atom(s) may be replaced with at least one heteroatom selected from nitrogen, oxygen, and sulfur.

According to another embodiment of the present disclosure, in formula 1 above, $X_1$ to $X_{13}$ each independently represent N or $CR_1$; L represents a single bond, an unsubstituted (C6-C15)arylene, or an unsubstituted 5- to 15-membered heteroarylene; Ar represents hydrogen; an unsubstituted (C6-C20)aryl; a 5- to 20-membered heteroaryl unsubstituted or substituted with a (C1-C6)alkyl, a (C6-C25)aryl, a 5- to 20-membered heteroaryl, or a (C1-C6)alkyl(C6-C15)aryl; or an unsubstituted di(C6-C15)arylamino; and $R_1$ represents hydrogen, or a di(C6-C15)arylamino unsubstituted or substituted with a (C1-C6)alkyl; or is linked to an adjacent substituent to form an unsubstituted monocyclic (C3-C15) aromatic ring.

The organic electroluminescent compound represented by formula 1 includes the following compounds, but is not limited thereto:

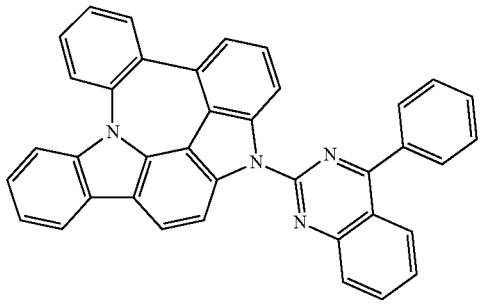

C-1

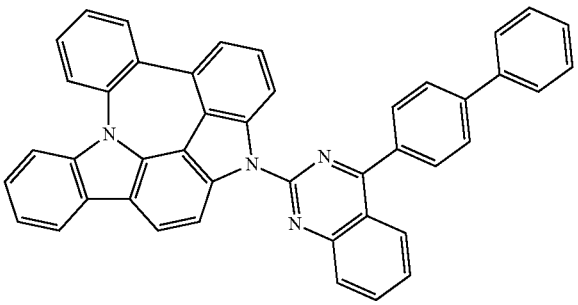

C-2

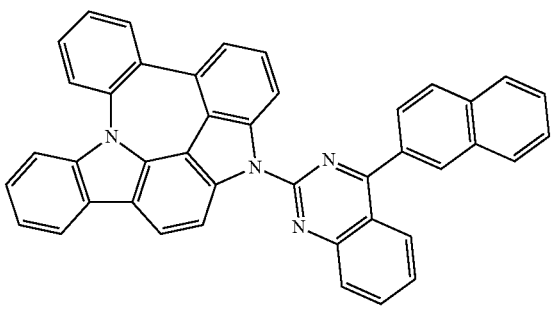

C-3

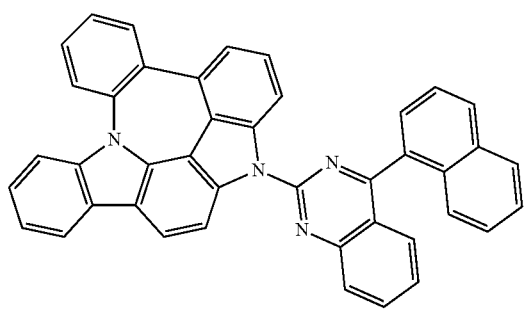

C-4

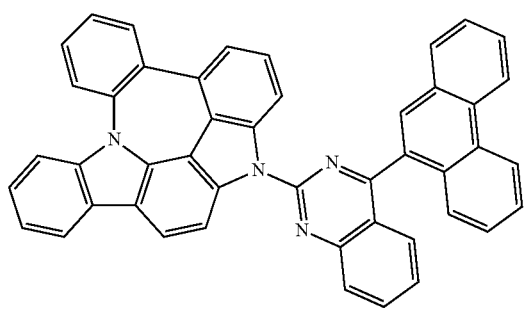

C-5

C-6
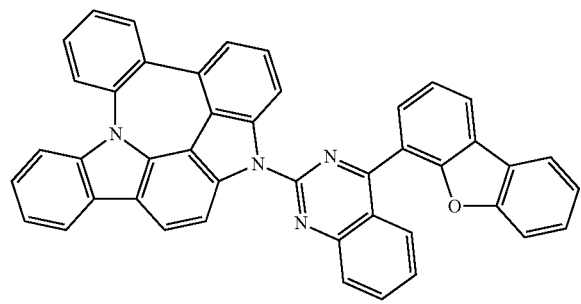
C-10
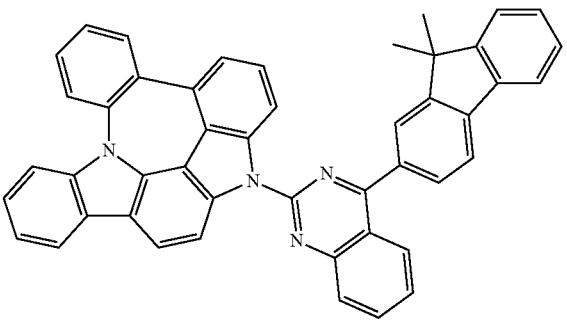
C-7
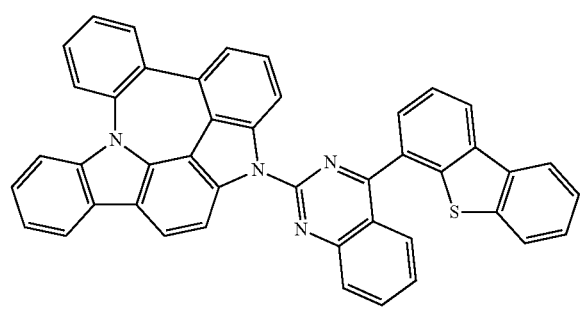
C-11
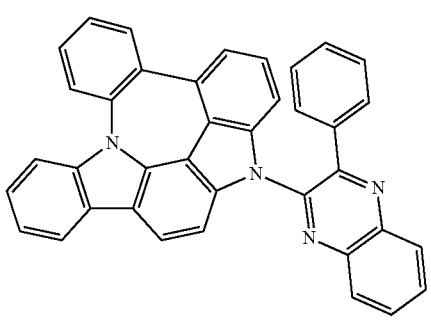
C-8
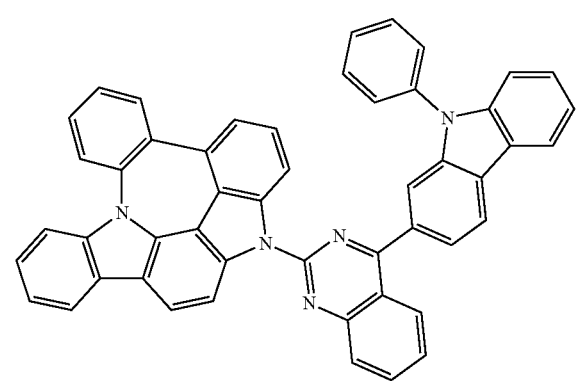
C-12
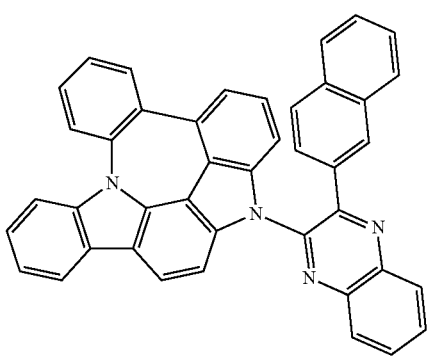
C-9
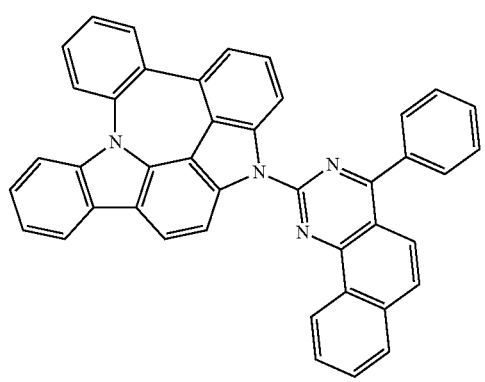
C-13
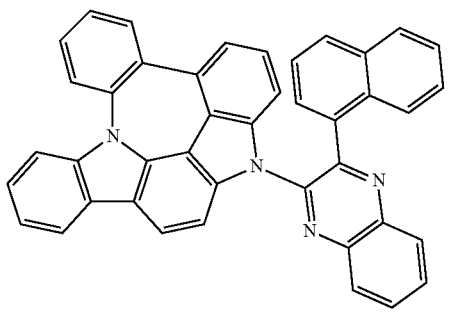

C-14
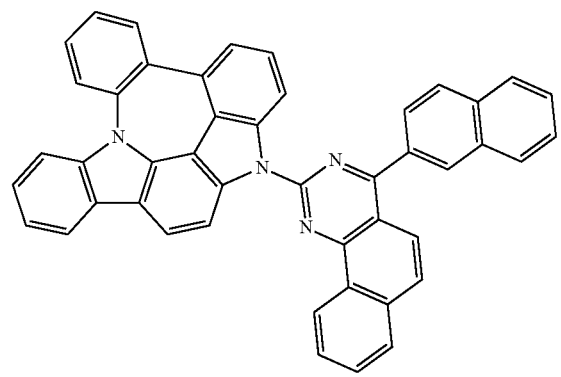
C-15
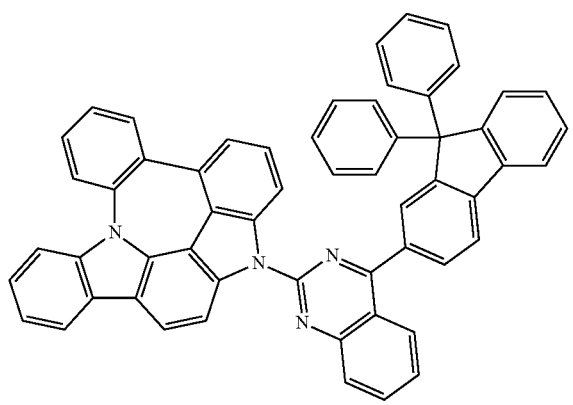
C-16
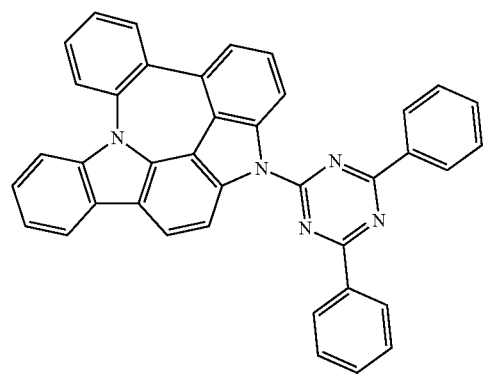
C-17
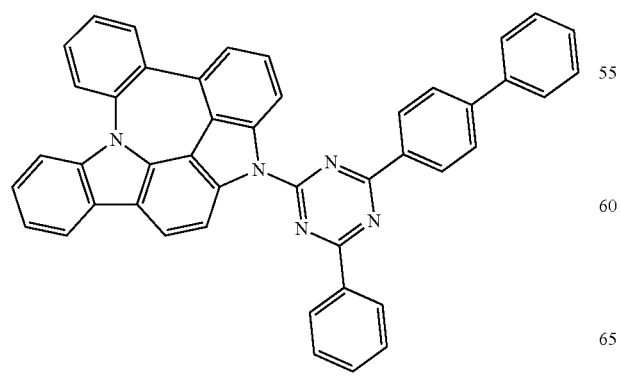
C-18
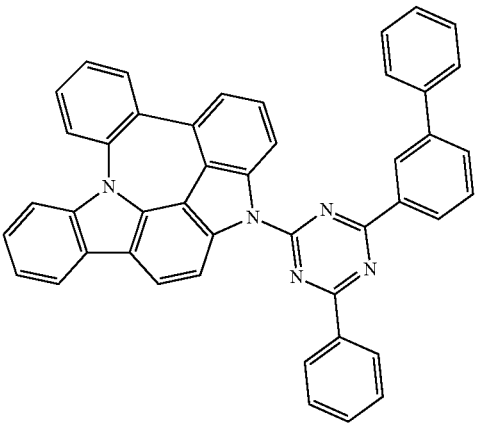
C-19
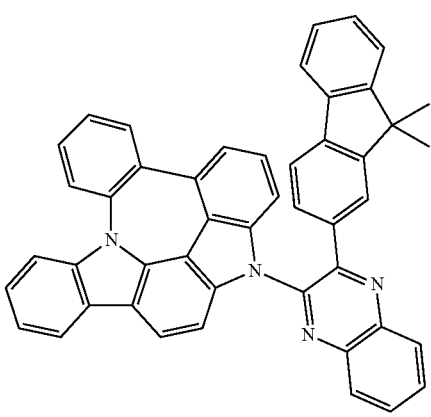
C-20
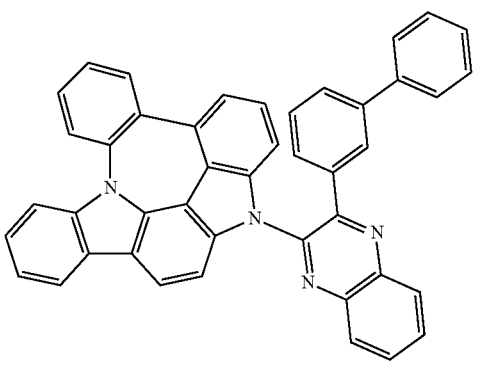
C-21
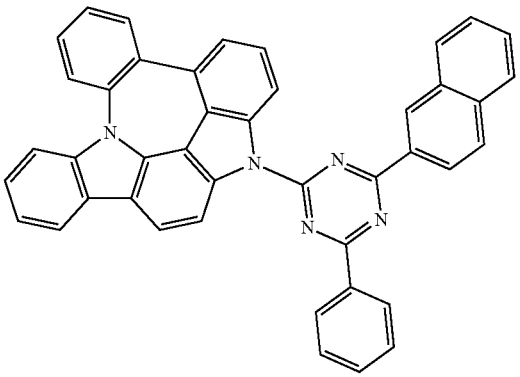

C-22
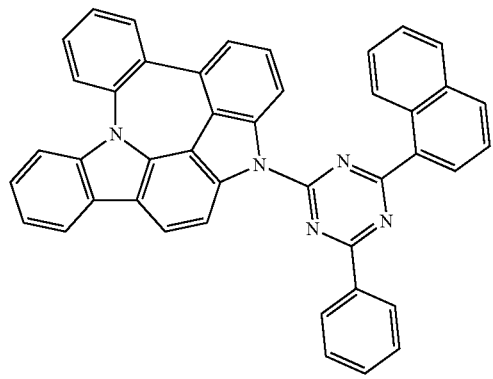
C-26
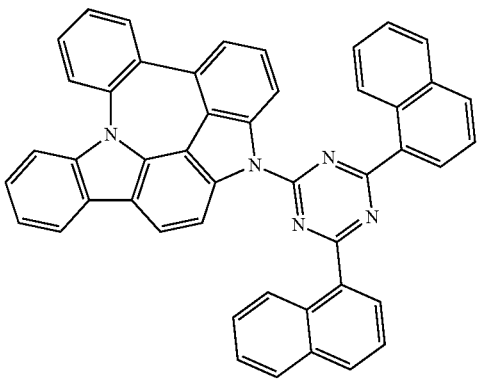
C-23
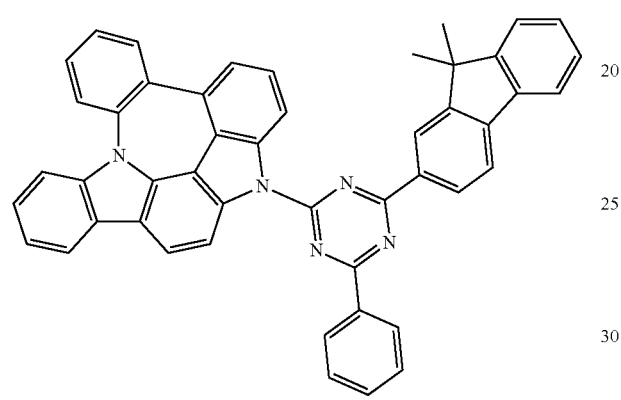
C-24
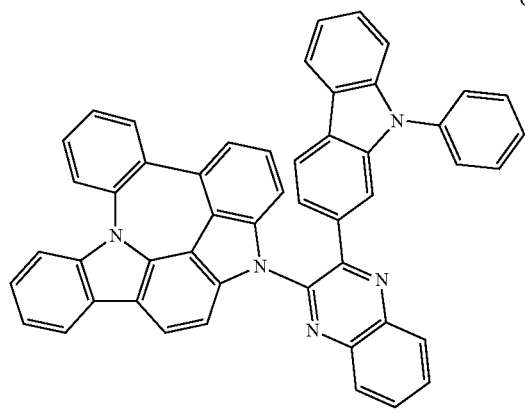
C-27
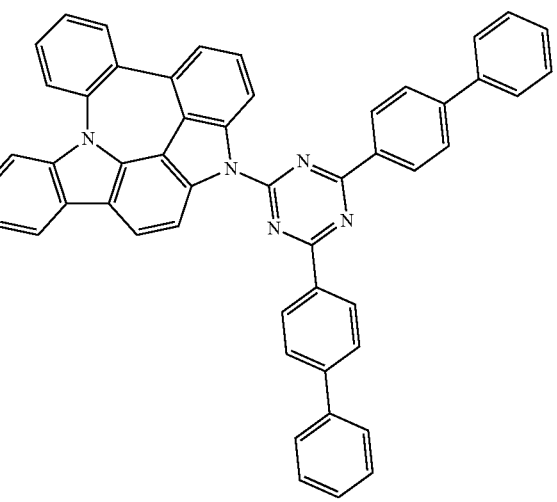
C-25
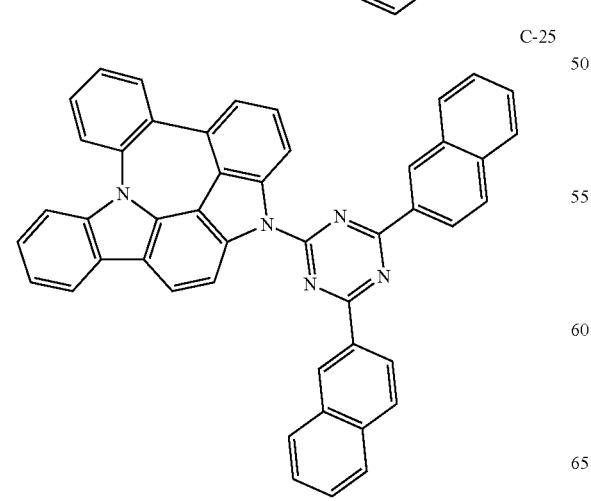
C-28
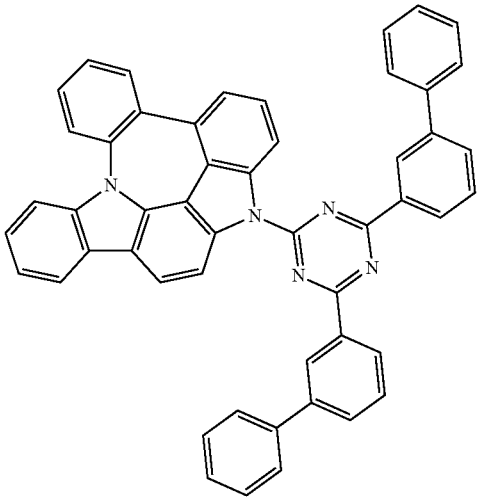

C-29
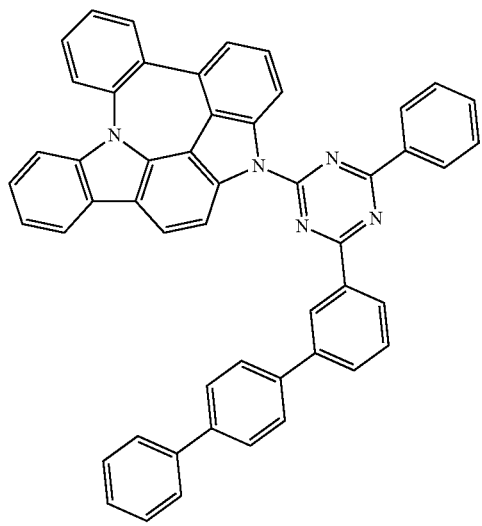
C-32
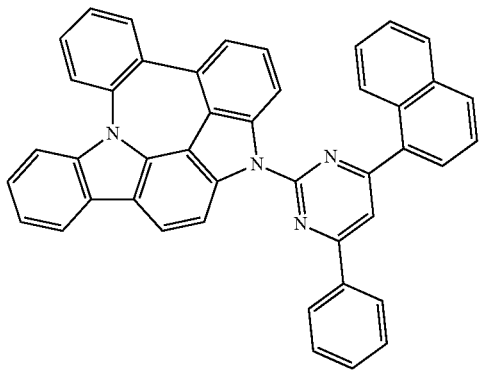
C-33
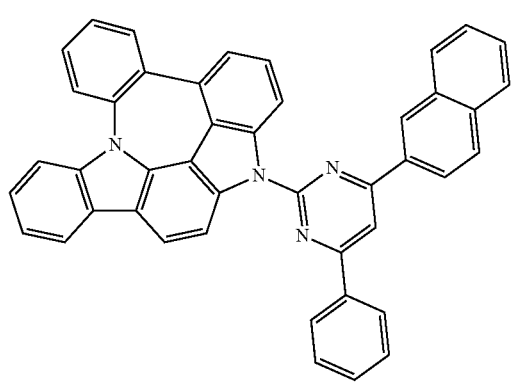
C-30
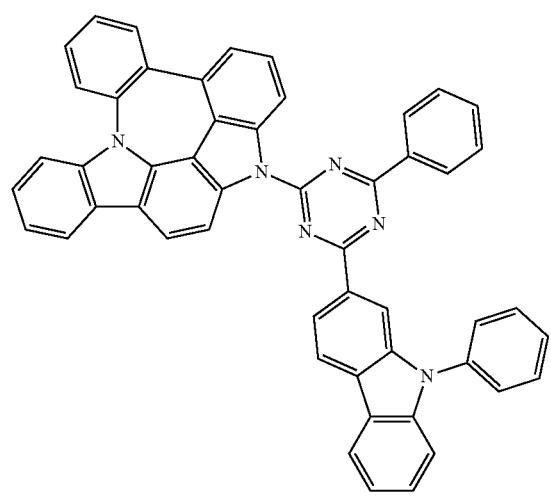
C-34
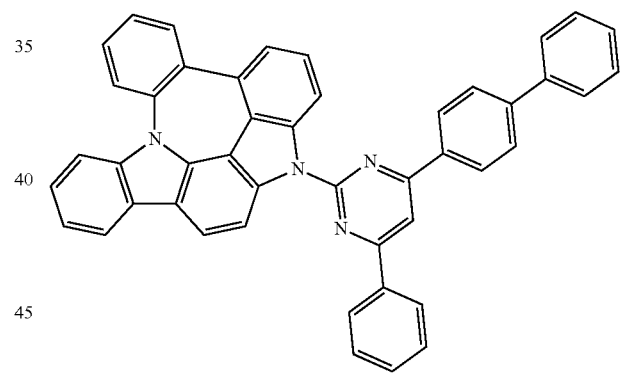
C-31
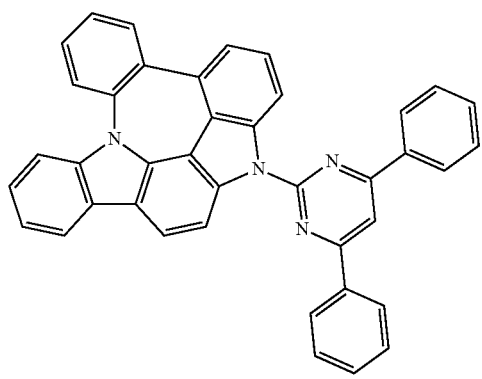
C-35
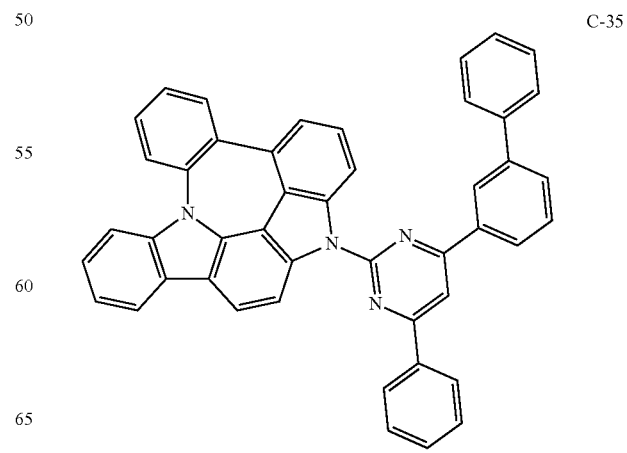

C-36
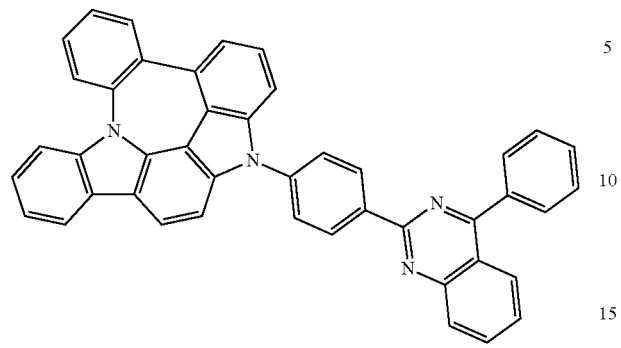
C-37
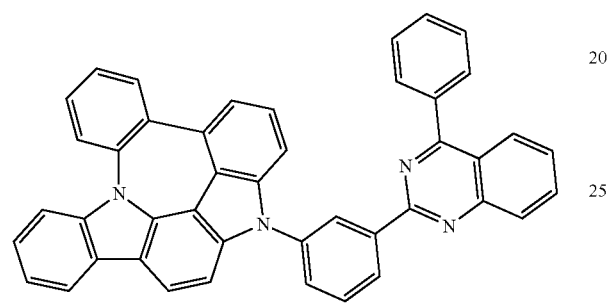
C-38
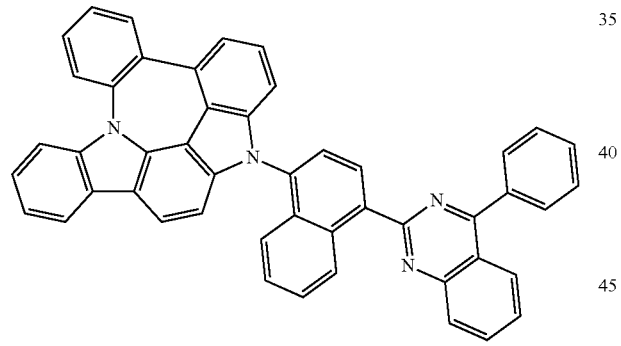
C-39
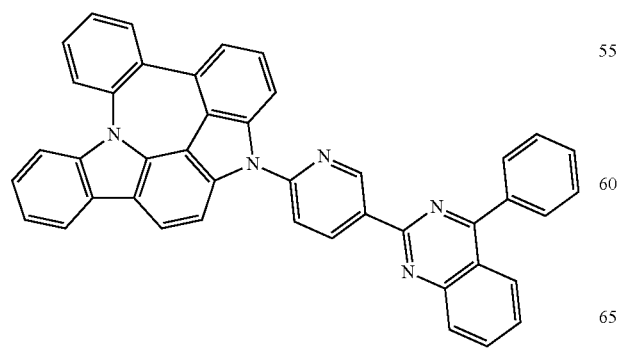
C-40
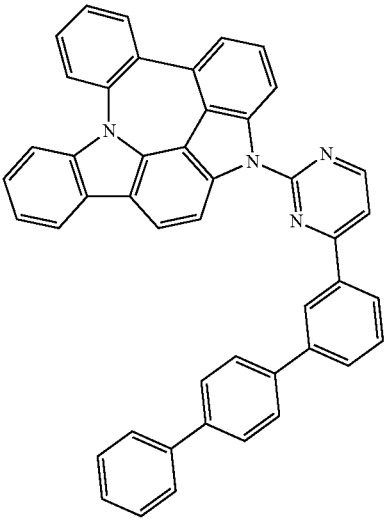
C-41
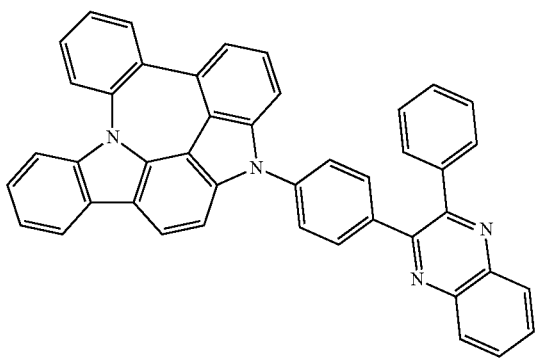
C-42
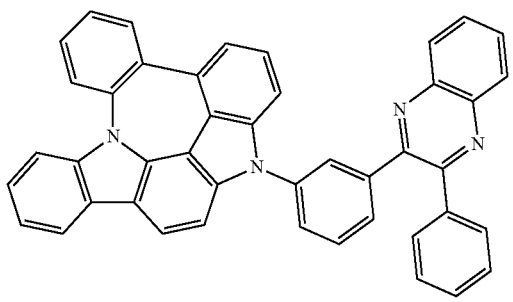
C-43
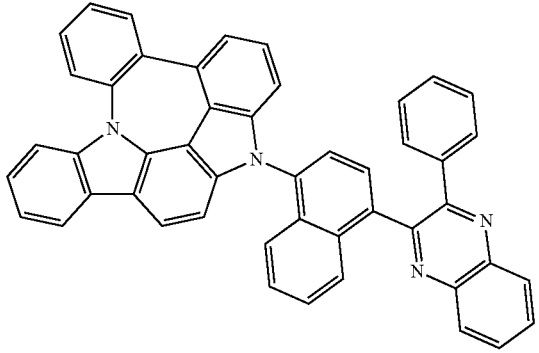

C-44
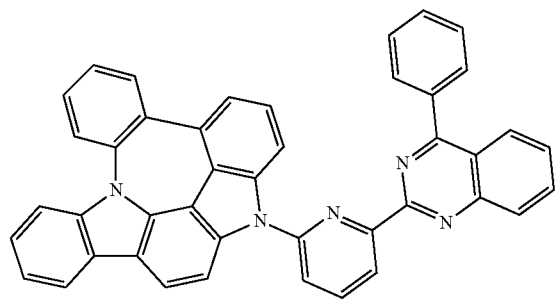
C-45
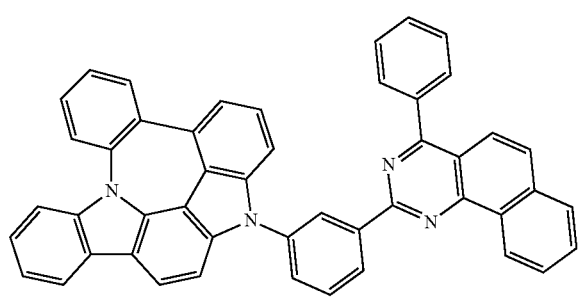
C-46
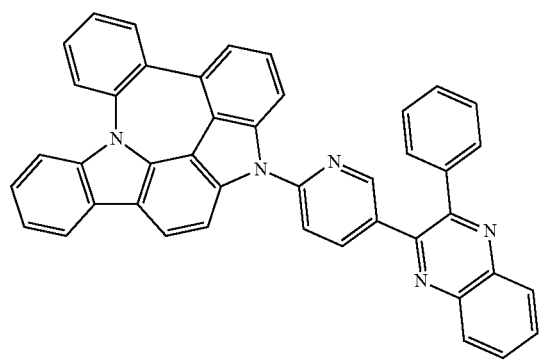
C-47
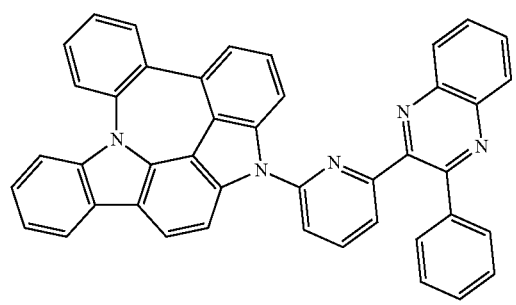
C-48
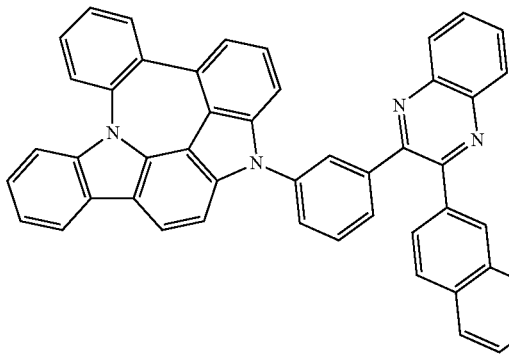
C-49
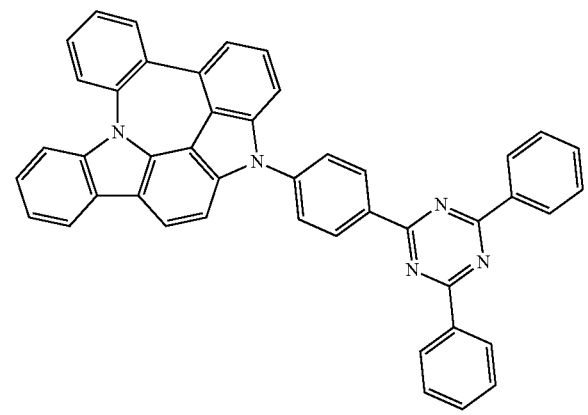
C-50
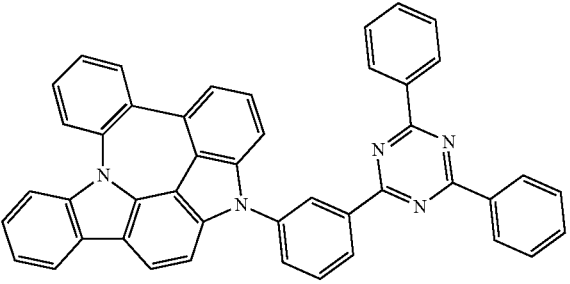
C-51
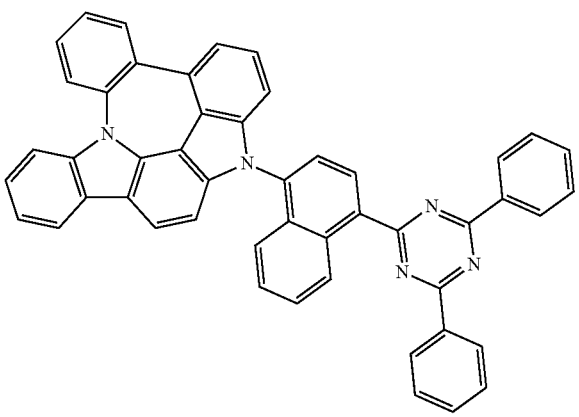

C-52
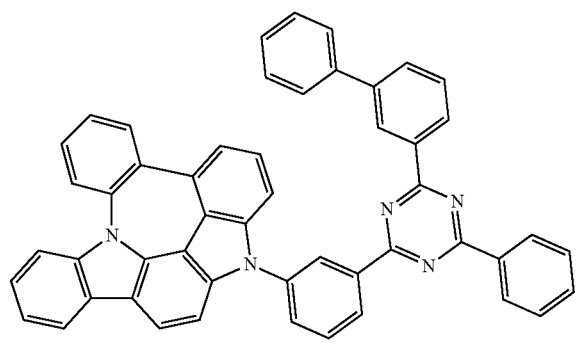
C-55
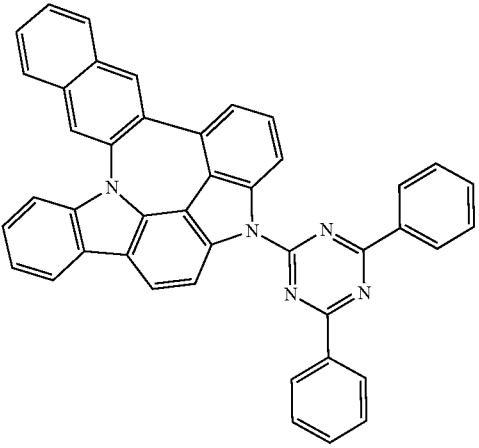
C-53
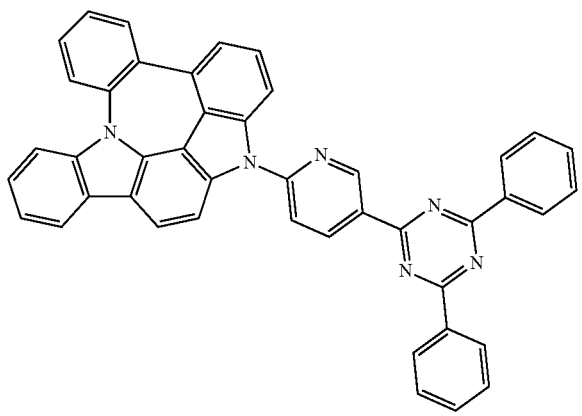
C-56
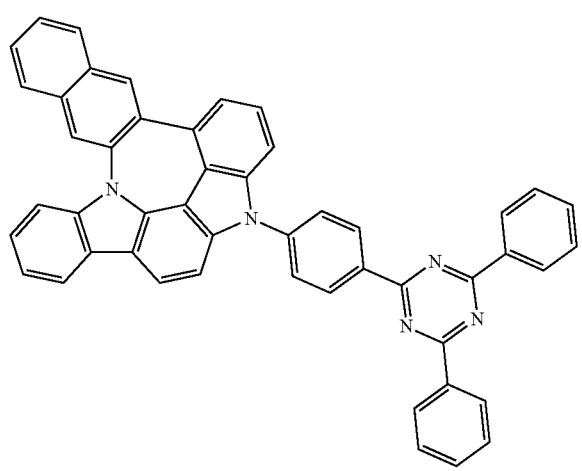
C-54
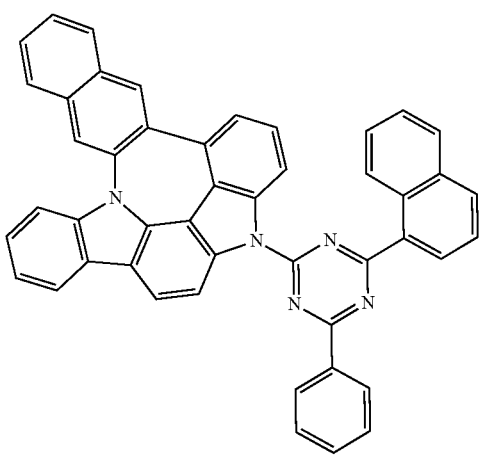
C-57
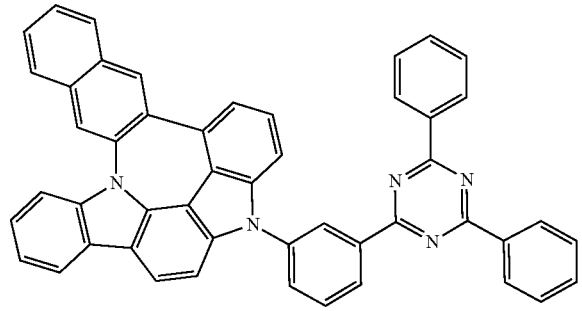

C-58
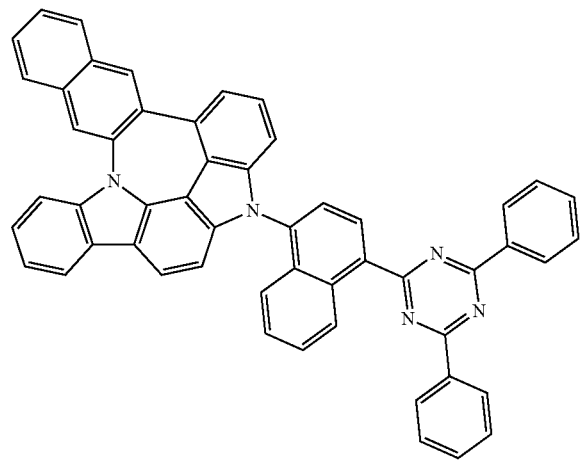
C-59
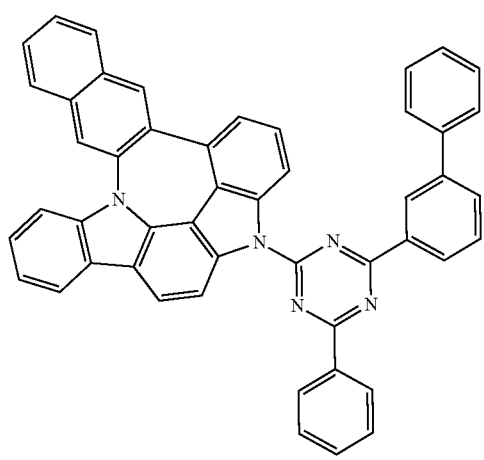
C-60
C-61
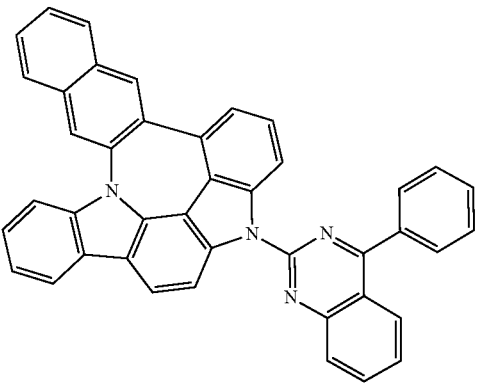
C-62
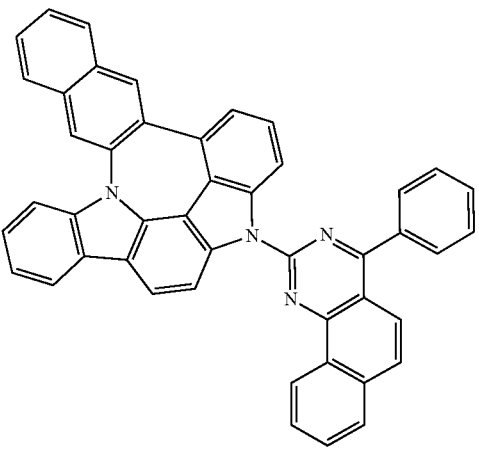
C-63
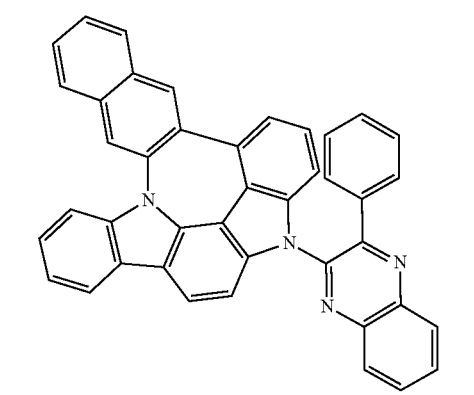
C-64
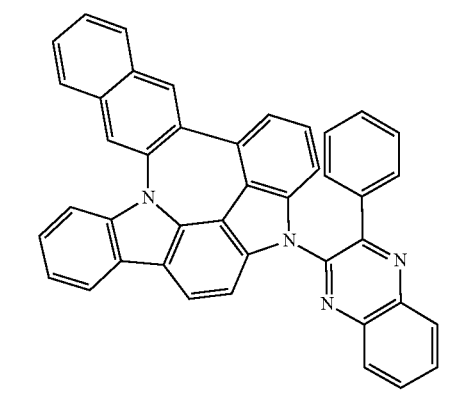

C-65
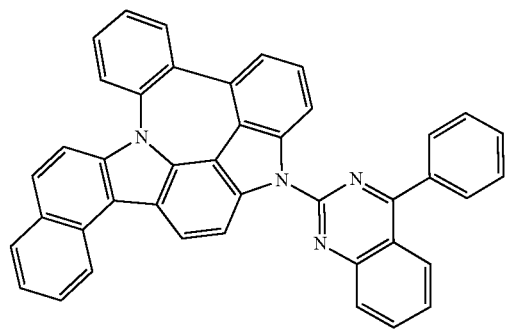
C-66
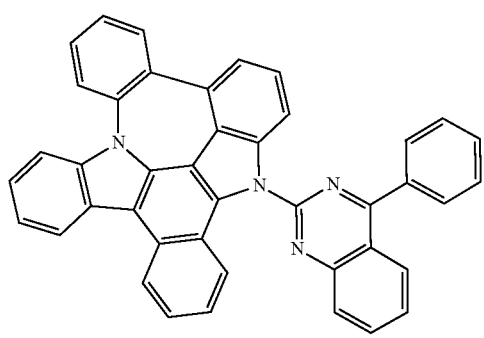
C-67
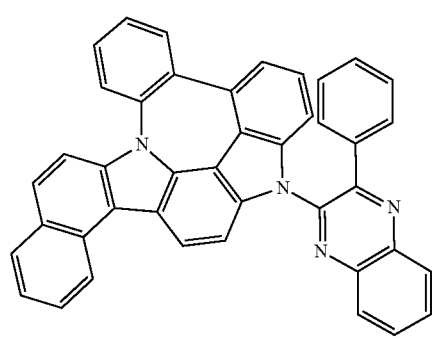
C-68
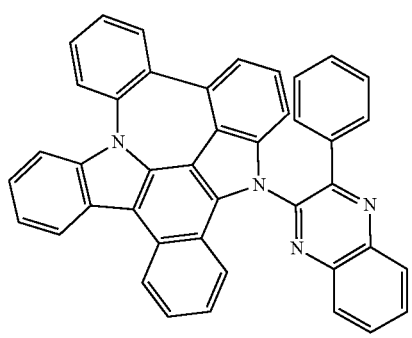
C-69
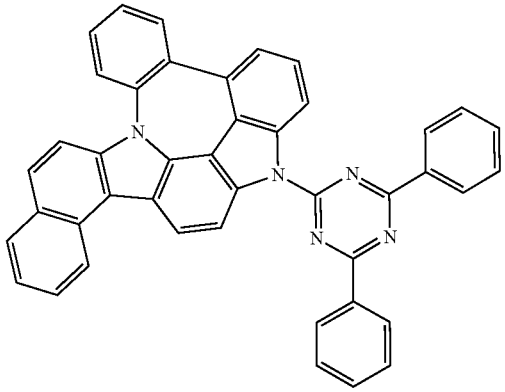
C-70
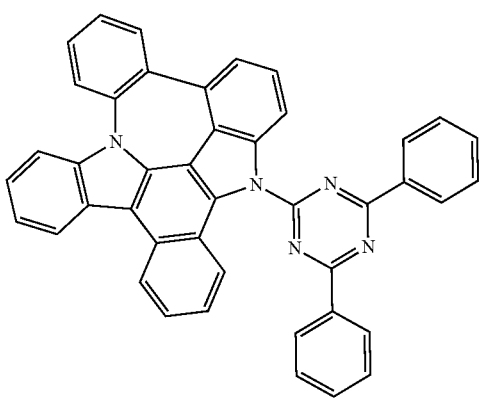
C-71
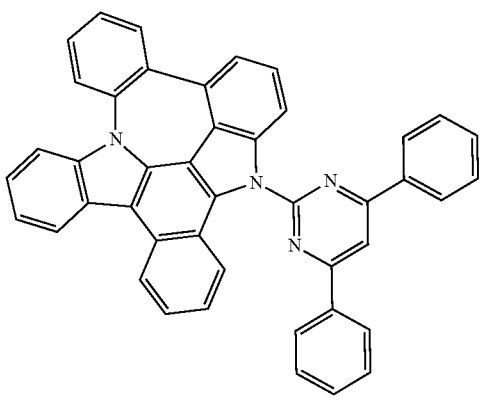
C-72
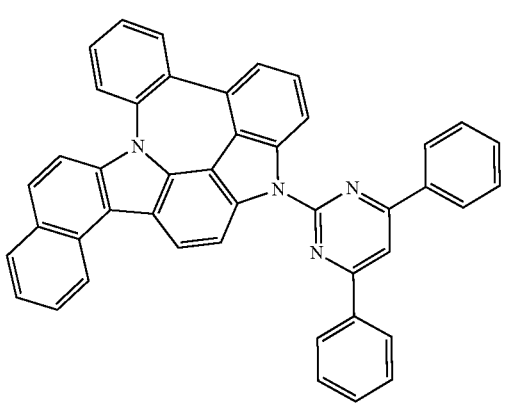

C-73
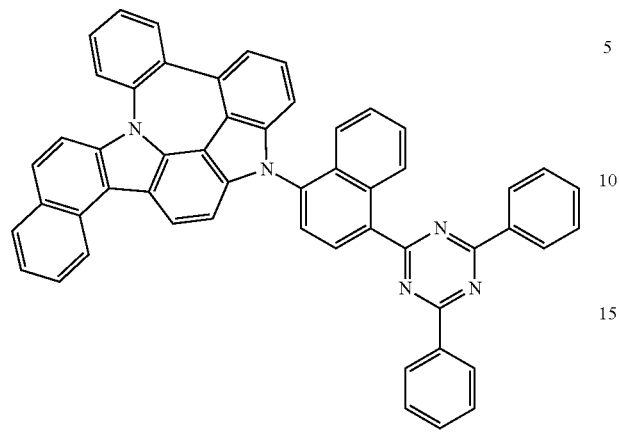
C-74
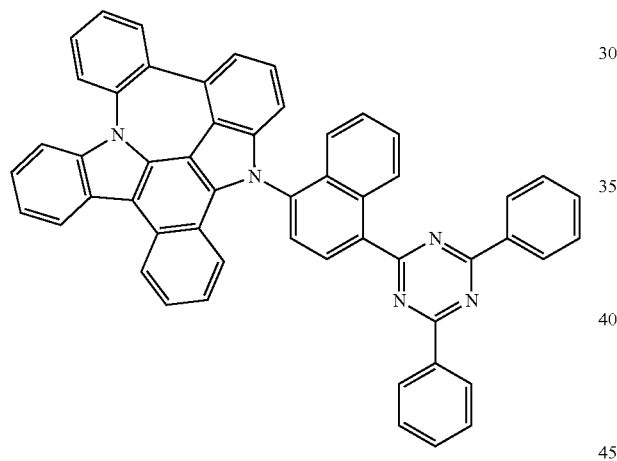
C-75
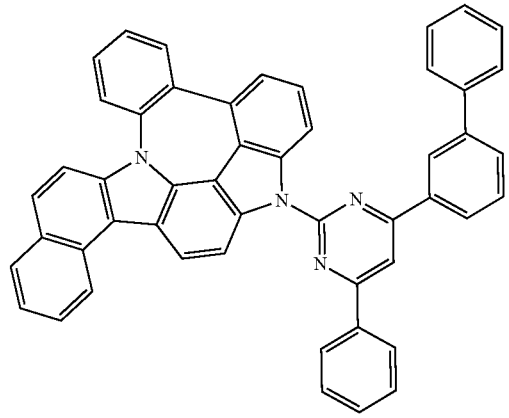
C-76
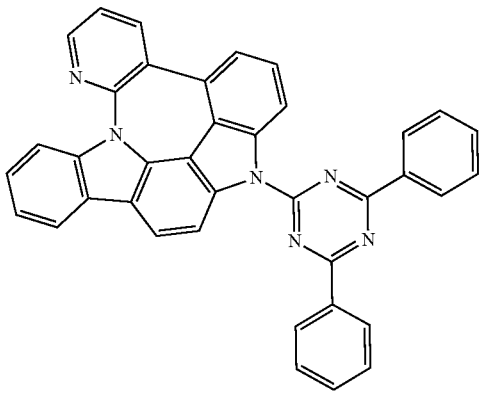
C-77
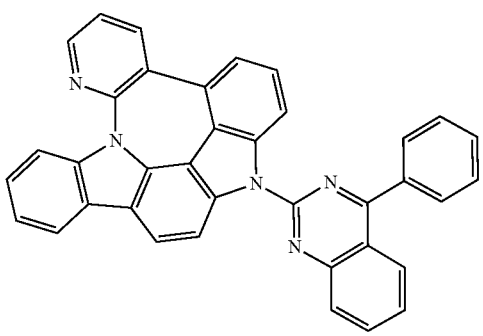
C-78
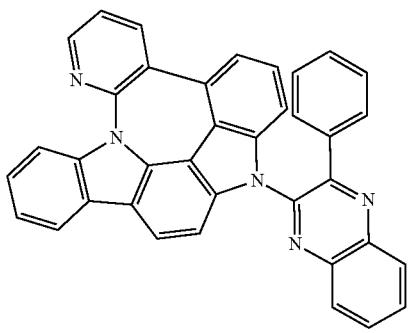
C-79
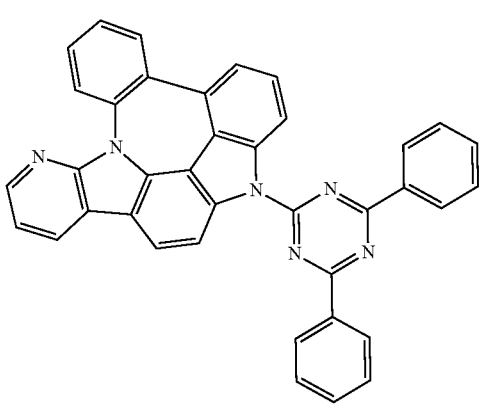

C-80
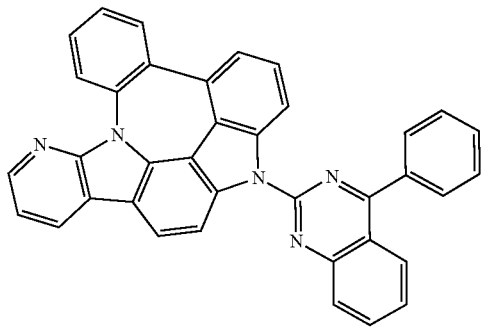
C-81
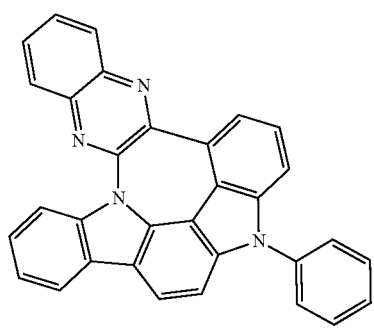
C-82
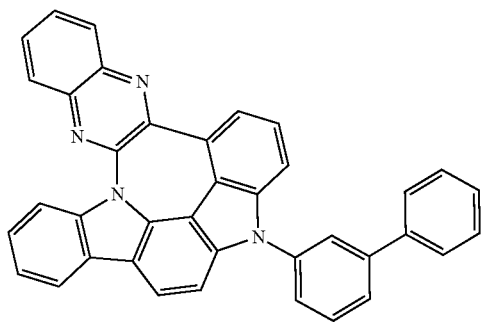
C-83
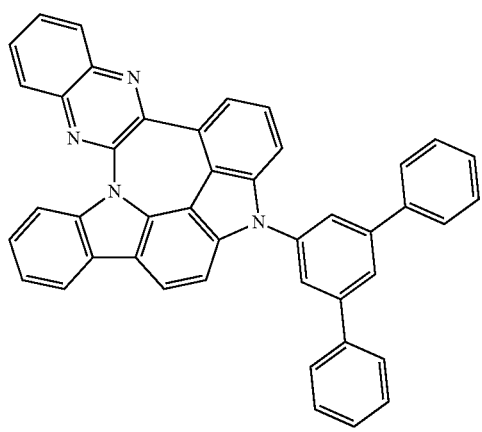
C-84
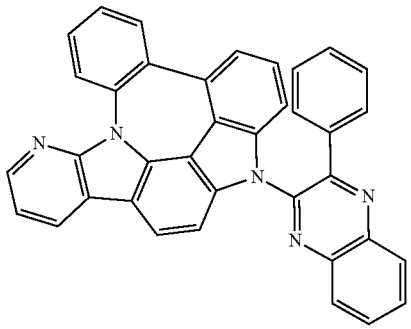
C-85
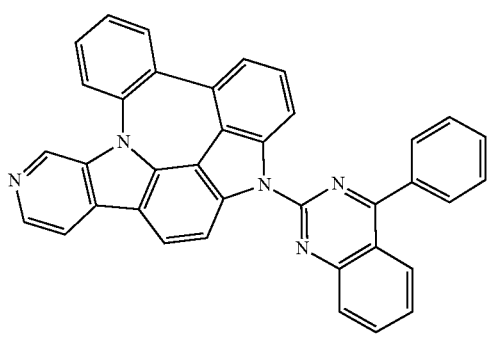
C-86
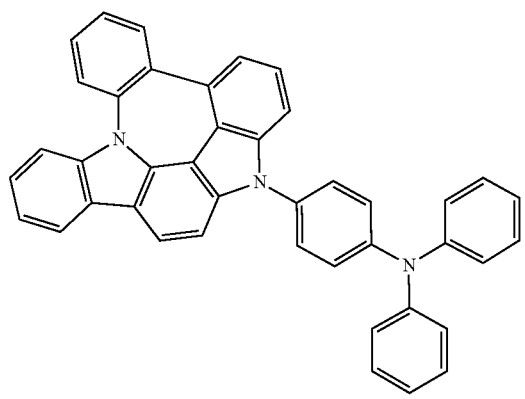
C-87
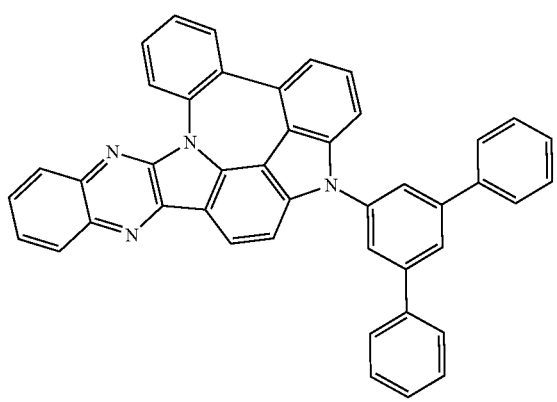

-continued
C-88
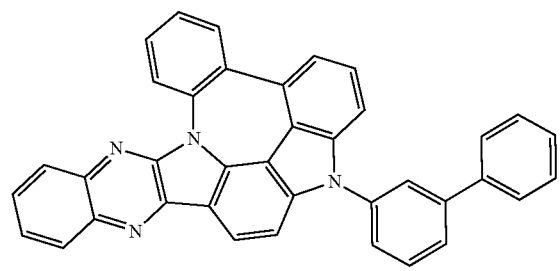
C-89
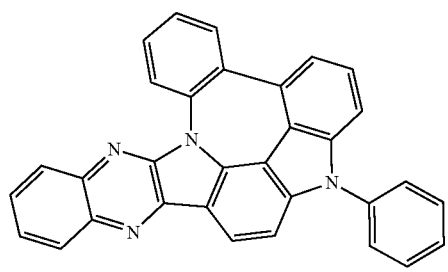
C-90
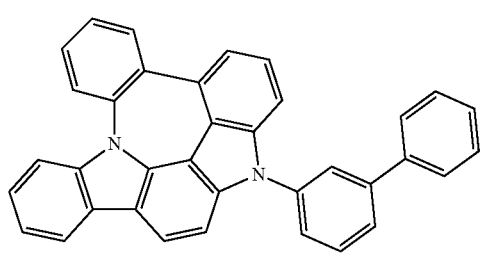
C-91
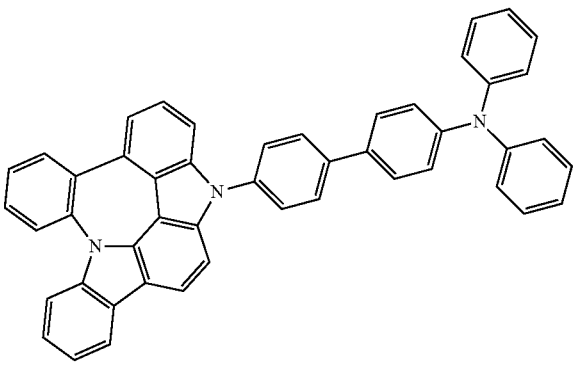
C-92
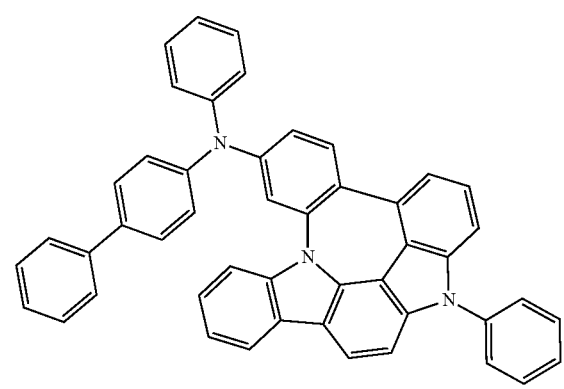
-continued
C-93
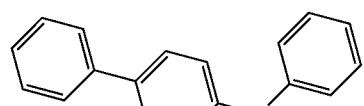
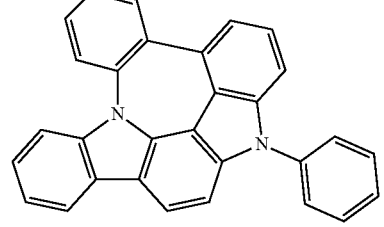
C-94
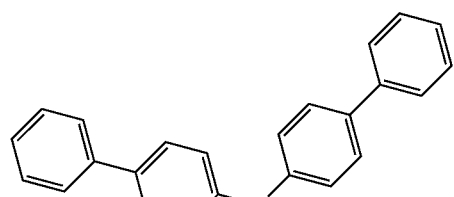
C-95
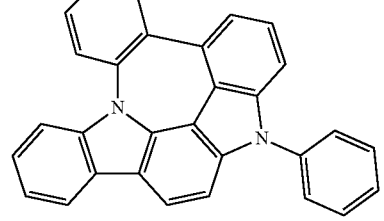
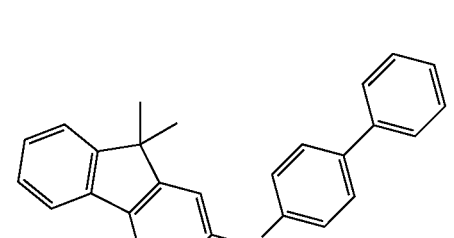
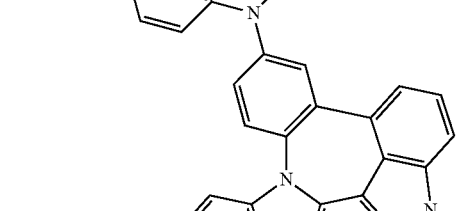
C-96
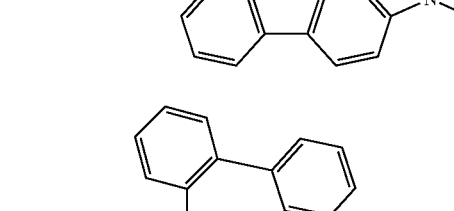
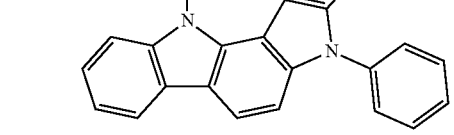

-continued
C-97
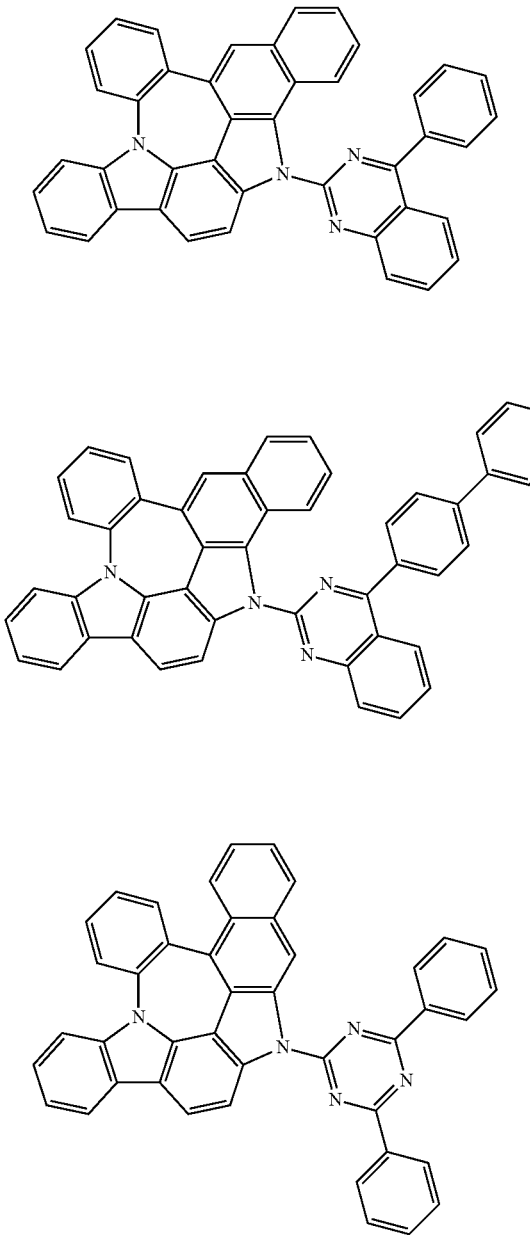
C-98
C-99
C-100
-continued
C-101
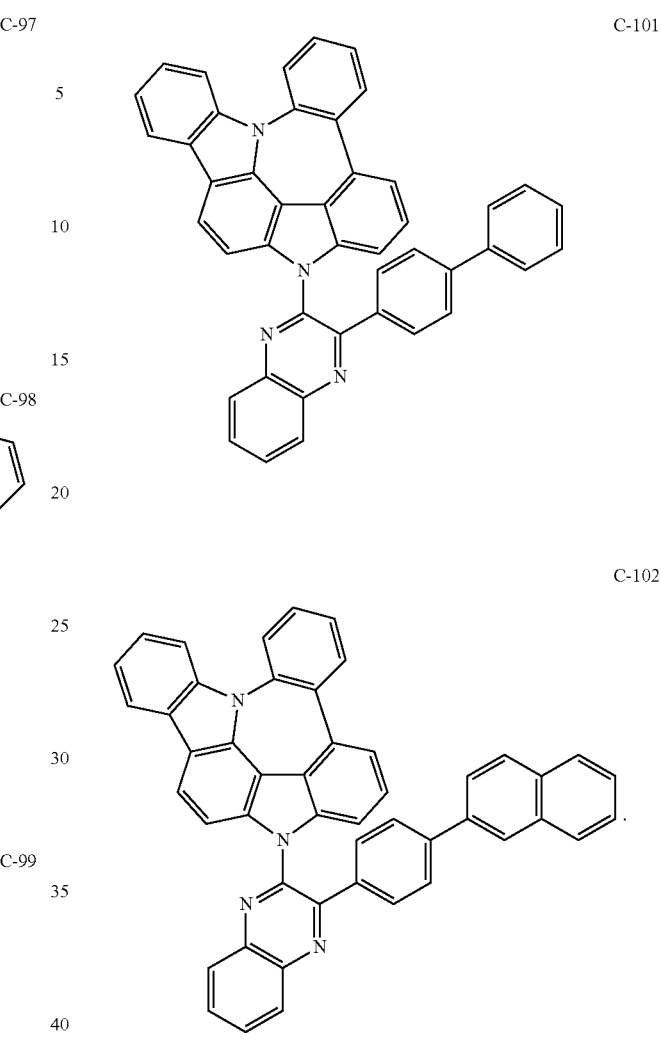
C-102
The organic electroluminescent compound according to the present disclosure can be prepared by a synthetic method known to a person skilled in the art. For example, it can be prepared according to the following reaction scheme.
[Reaction Scheme 1]
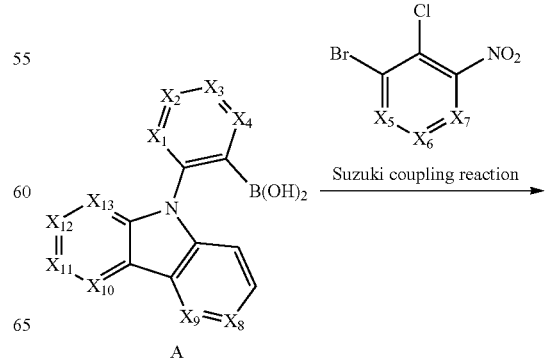

-continued

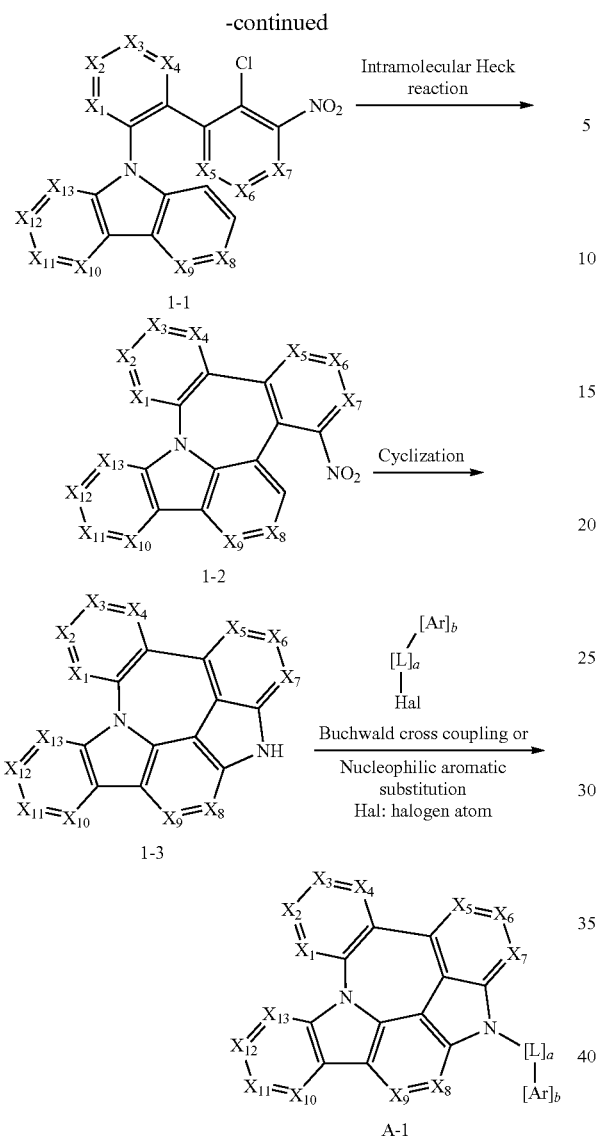

wherein $X_1$ to $X_{13}$, L, Ar, $R_1$, a, and b are as defined in formula 1, and Hal represents a halogen.

The present disclosure provides an organic electroluminescent material comprising the organic electroluminescent compound of formula 1, and an organic electroluminescent device comprising the material.

The above material can be comprised of the organic electroluminescent compound according to the present disclosure alone, or can further include conventional materials generally used in organic electroluminescent materials.

The organic electroluminescent device according to the present disclosure comprises a first electrode; a second electrode; and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The organic electroluminescent compound of formula 1 of the present disclosure may be comprised in the light-emitting layer. Where used in the light-emitting layer, the organic electroluminescent compound of formula 1 of the present disclosure can be comprised as a host material. Preferably, the light-emitting layer can further comprise one or more dopants. If necessary, the organic electroluminescent compound of the present disclosure can be used as a co-host material. That is, the light-emitting layer can additionally comprise a compound other than the organic electroluminescent compound of formula 1 of the present disclosure (first host material) as a second host material. Herein, the weight ratio of the first host material to the second host material is in the range of 1:99 to 99:1.

The second host material can be any of the known hosts. The host selected from the group consisting of the compounds of formulas 11 to 16 below may be preferable in terms of luminous efficiency.

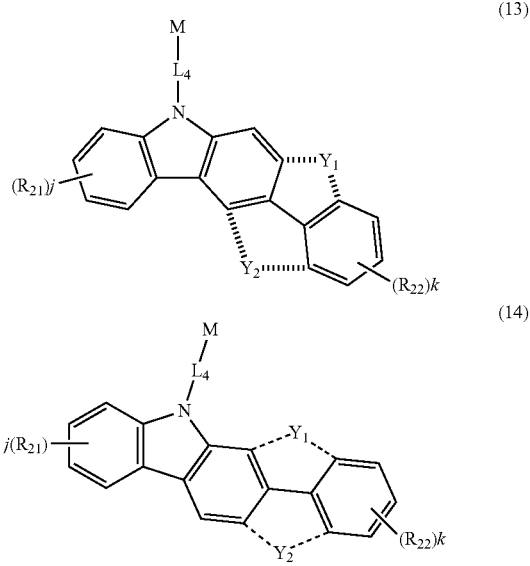

wherein
Cz represents the following structure:

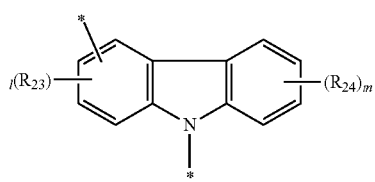

A represents —O— or —S—; and

R$_{21}$ to R$_{24}$, each independently, represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, or —SiR$_{25}$R$_{26}$R$_{27}$; in which R$_{25}$ to R$_{27}$, each independently, represent a substituted or unsubstituted (C1-C30)alkyl, or a substituted or unsubstituted (C6-C30)aryl; L$_4$ represents a single bond, a substituted or unsubstituted (C6-C30)arylene, or a substituted or unsubstituted 5- to 30-membered heteroarylene; M represents a substituted or unsubstituted (C6-C30)aryl, or a substituted or unsubstituted 5- to 30-membered heteroaryl; Y$_1$ and Y$_2$, each independently, represent —O—, —S—, —N(R$_{31}$)— or —C(R$_{32}$)(R$_{33}$)—, with the proviso that Y$_1$ and Y$_2$ are not present simultaneously; R$_{31}$ to R$_{33}$, each independently, represent a substituted or unsubstituted (C1-C30)alkyl, a substituted or unsubstituted (C6-C30)aryl, or a substituted or unsubstituted 5- to 30-membered heteroaryl; R$_{32}$ and R$_{33}$ may be the same or different; h and i, each independently, represent an integer of 1 to 3; j, k, l, and m, each independently, represent an integer of 0 to 4; q represents an integer of 0 to 3; if h, i, j, k, l, m, or q represents an integer of 2 or more, each (Cz-L$_4$), each (Cz), each R$_{21}$, each R$_{22}$, each R$_{23}$, or each R$_{24}$ may be the same or different;

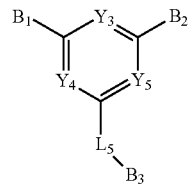
(16)

wherein

Y$_3$ to Y$_5$, each independently, represent CR$_{34}$ or N;

R$_{34}$ represents hydrogen, a substituted or unsubstituted (C1-C30)alkyl, a substituted or unsubstituted (C6-C30)aryl, or a substituted or unsubstituted 5- to 30-membered heteroaryl;

B$_1$ and B$_2$, each independently, represent hydrogen, a substituted or unsubstituted (C6-C30)aryl, or a substituted or unsubstituted 5- to 30-membered heteroaryl;

B$_3$ represents a substituted or unsubstituted (C6-C30)aryl, or a substituted or unsubstituted 5- to 30-membered heteroaryl; and L$_5$ represents a single bond, a substituted or unsubstituted (C6-C30)arylene, or a substituted or unsubstituted 5- to 30-membered heteroarylene.

Specifically, the examples of the second host material are as follows, but are not limited thereto.

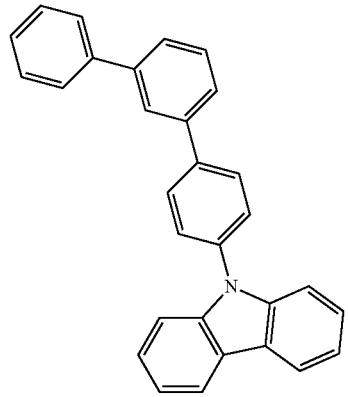
B-1

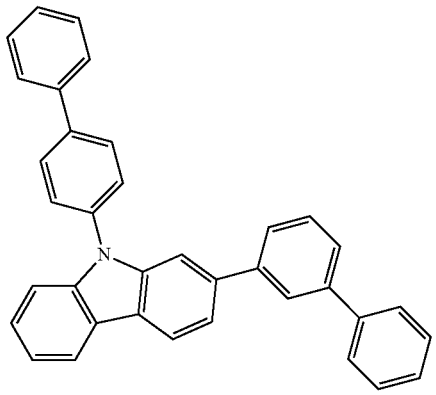
B-2

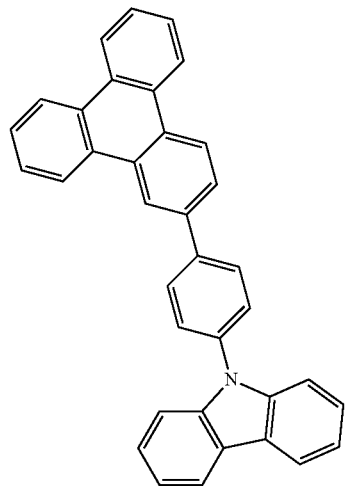
B-3

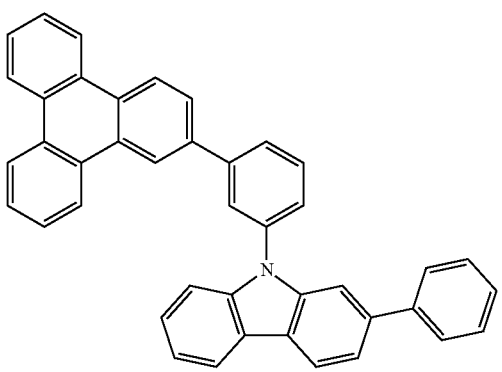
B-4

B-5
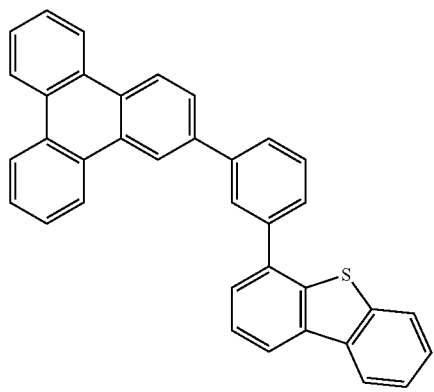
B-6
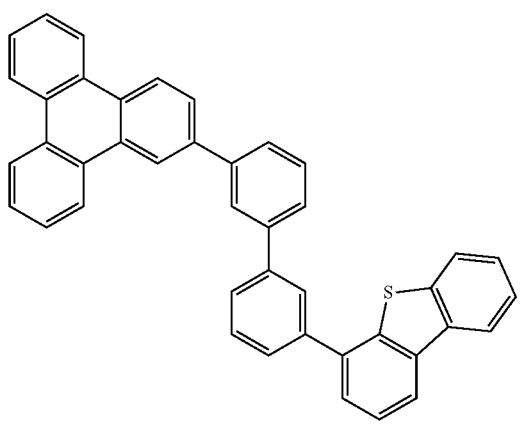
B-7
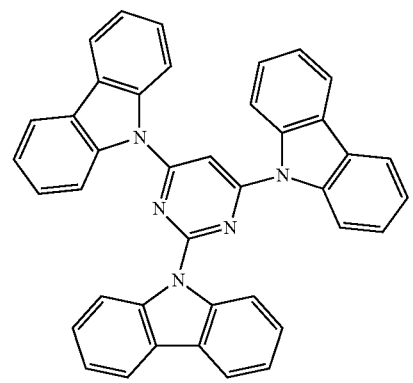
B-8
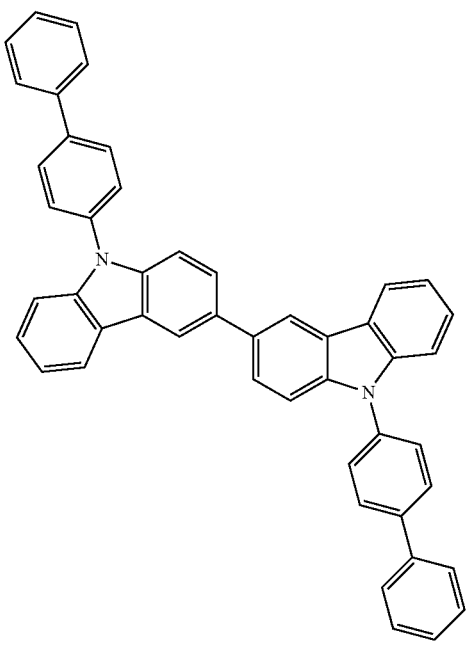
B-9
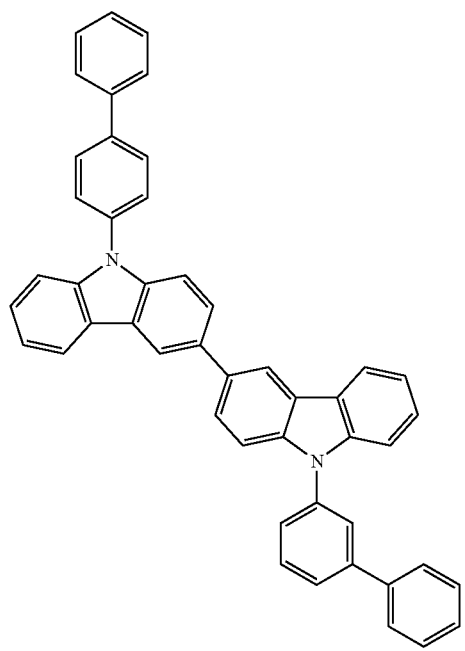

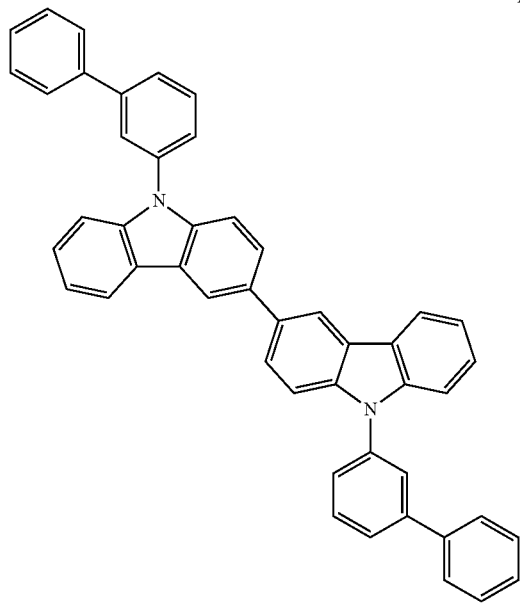
B-10
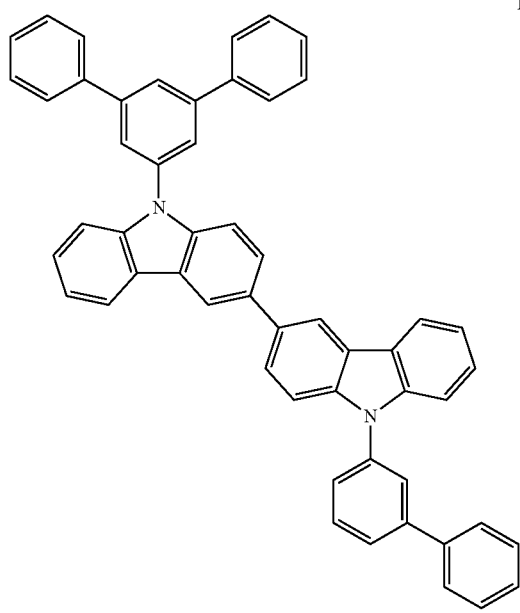
B-11
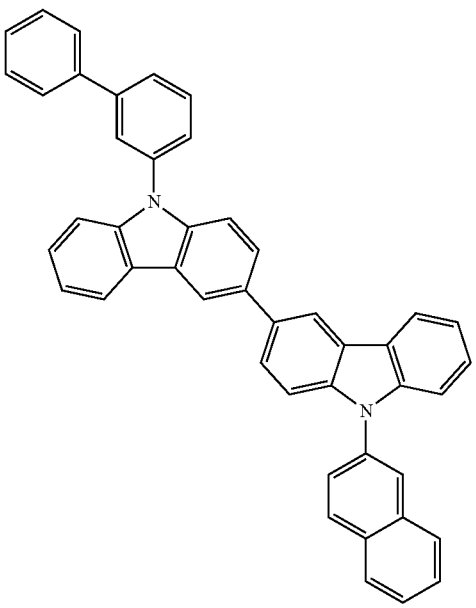
B-12
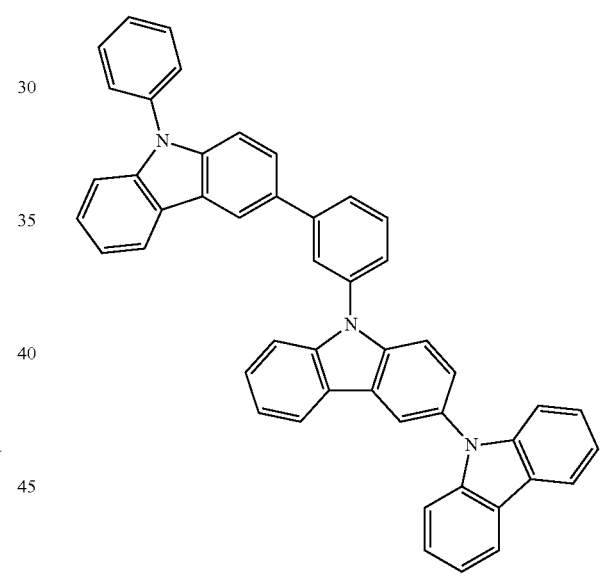
B-13
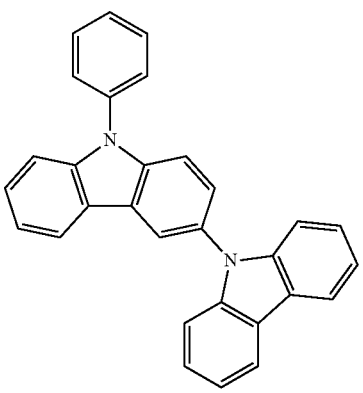
B-14

B-15
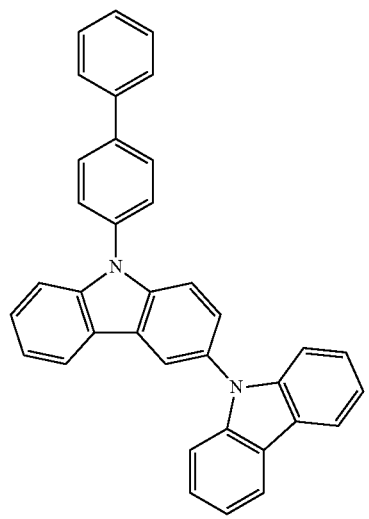
B-18
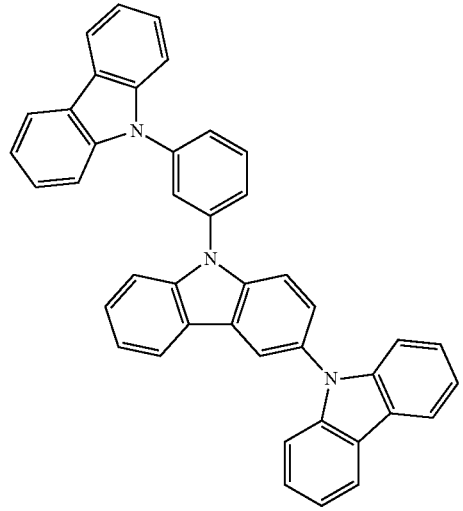
B-16
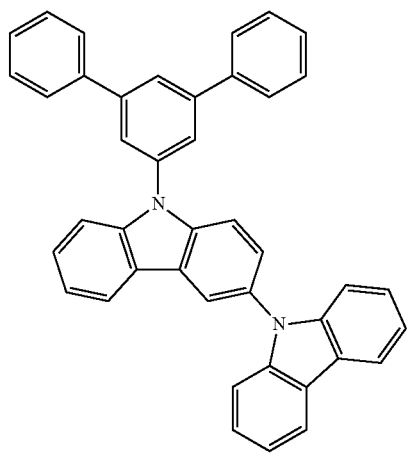
B-19
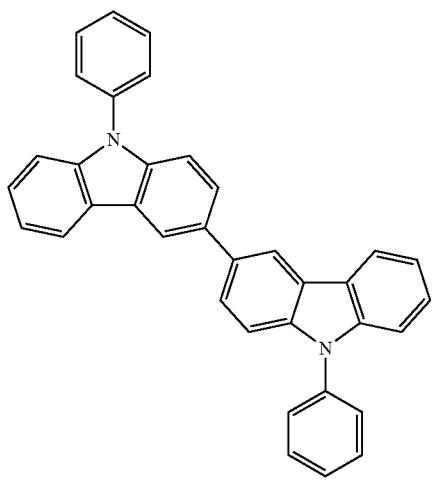
B-17
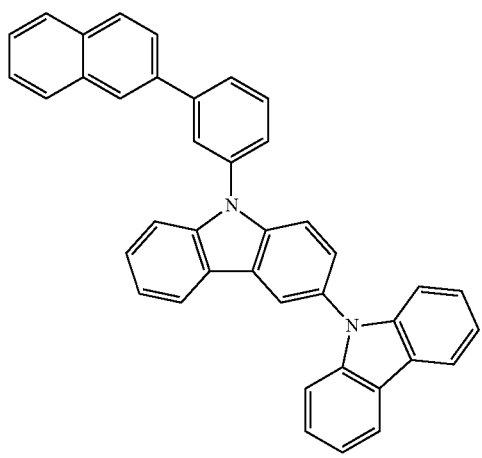
B-20
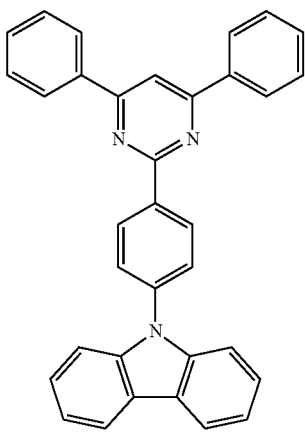

B-21
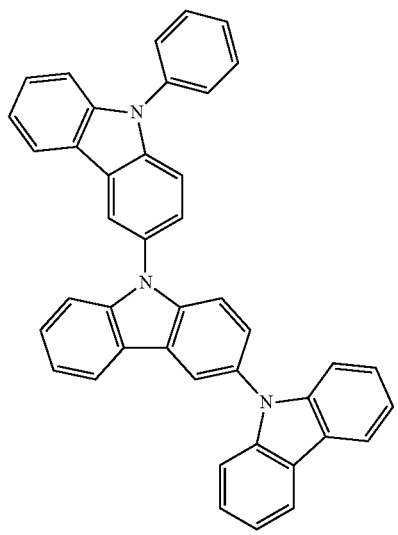
B-23
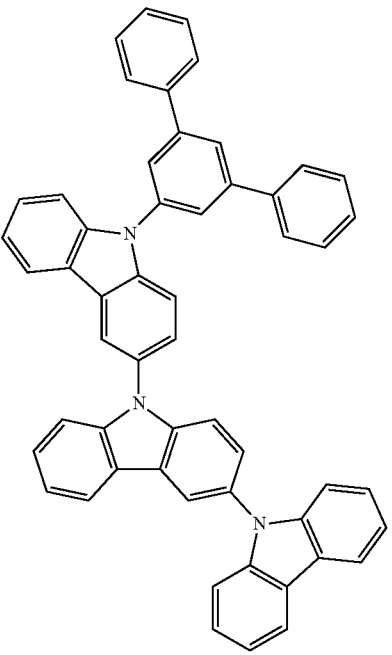
B-22
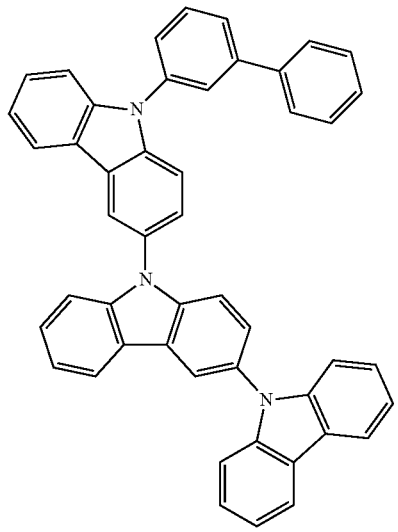
B-24
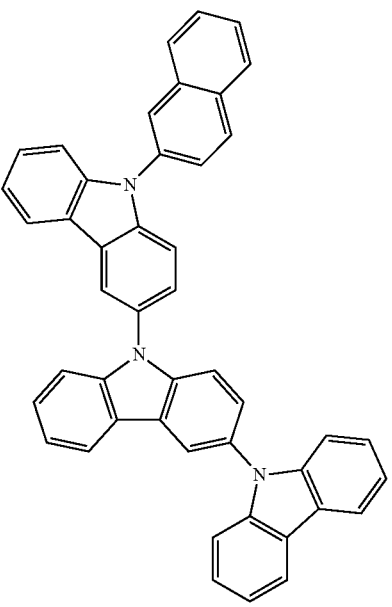

B-25

B-26

B-27

B-28

B-29

B-30

B-31

B-32
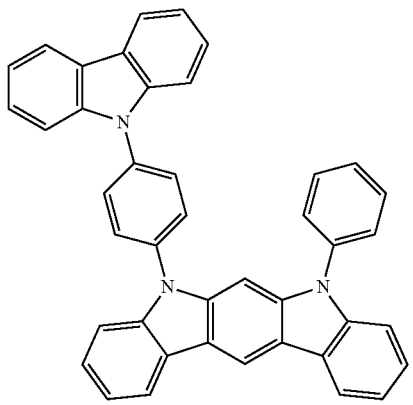
B-35
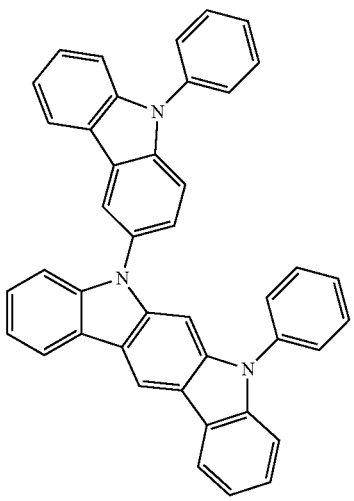
B-33
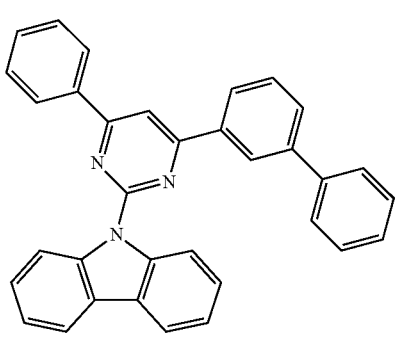
B-36
B-34
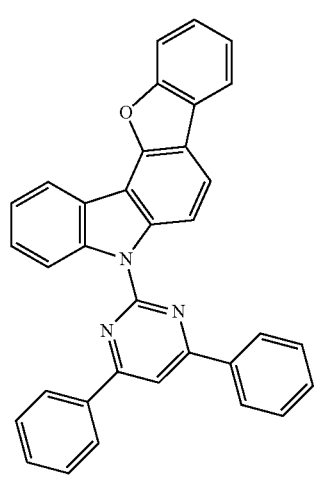
B-37
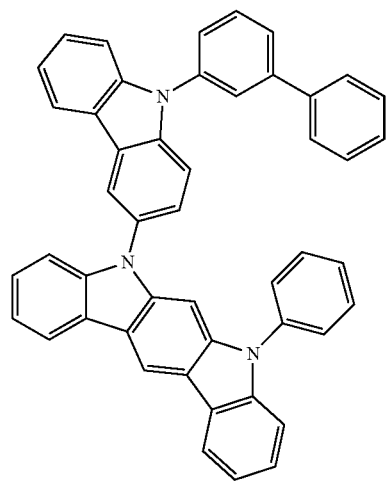

B-38
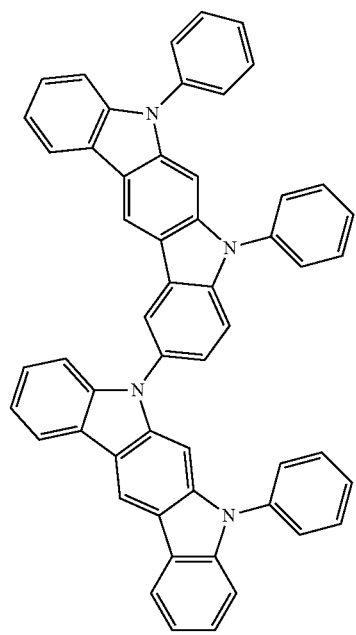
B-39
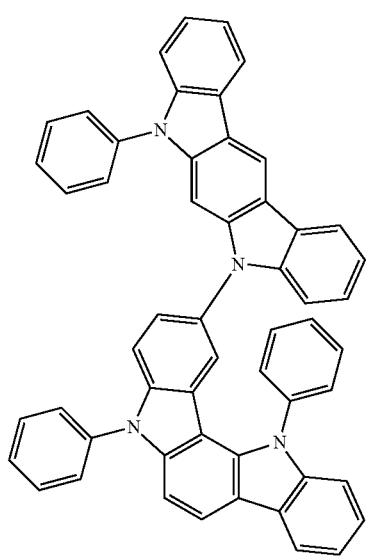
B-40
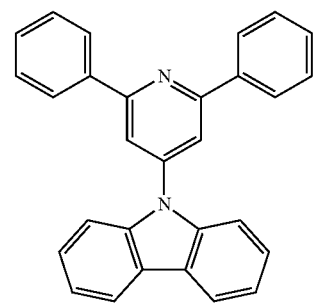
B-41
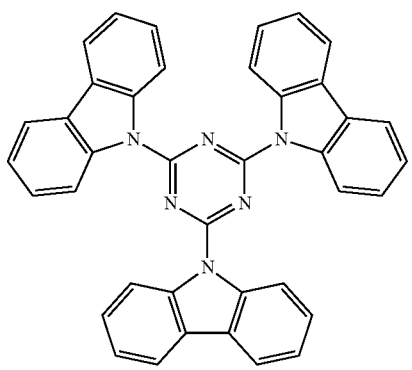
B-42
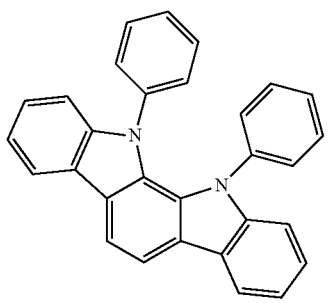
B-43
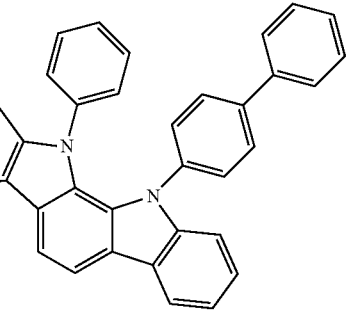
B-44
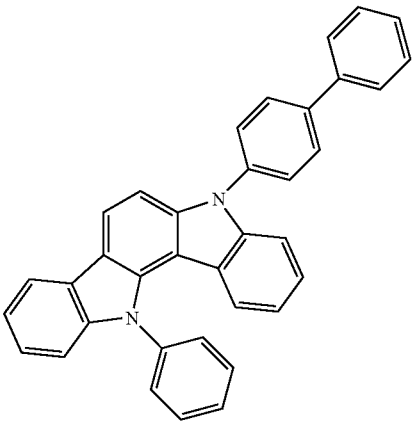

B-45
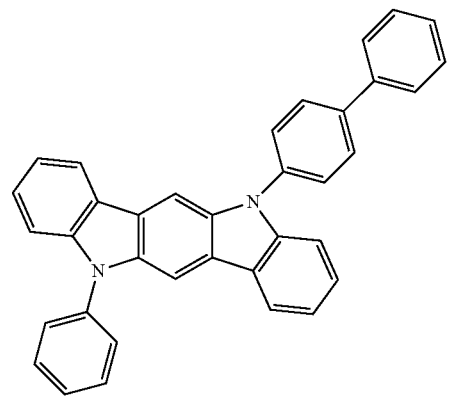
B-46
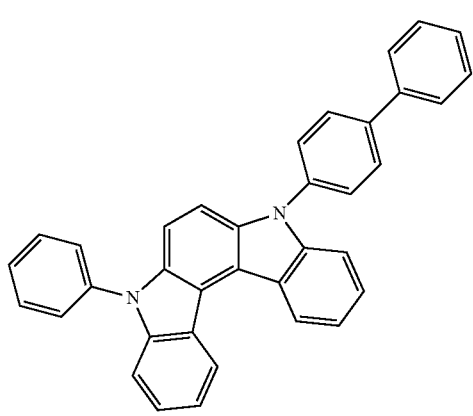
B-47
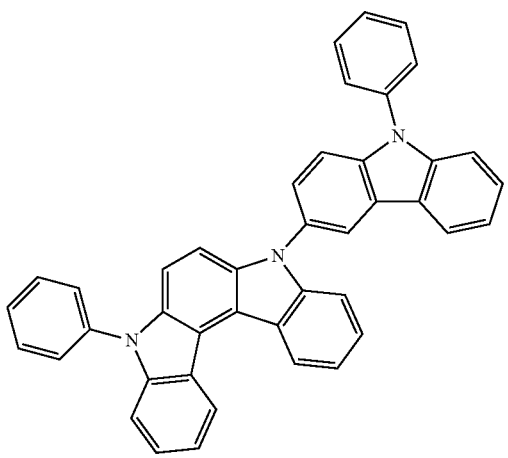
B-48
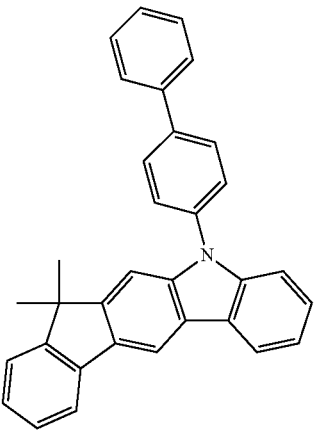
B-49
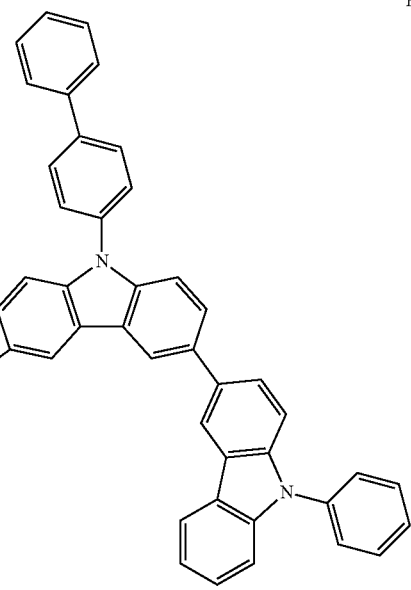
B-50
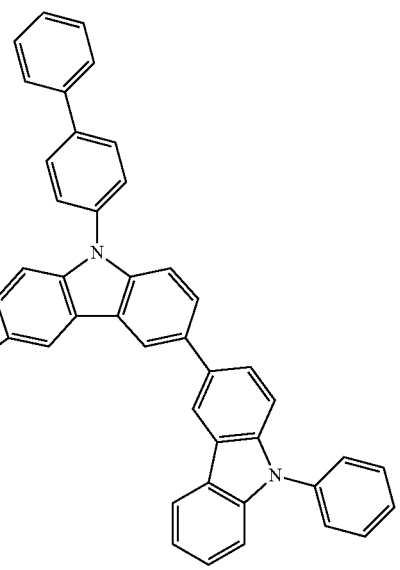

B-51
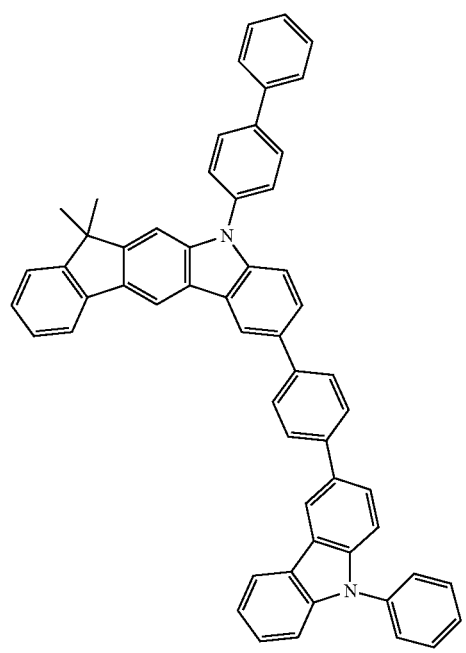
B-52
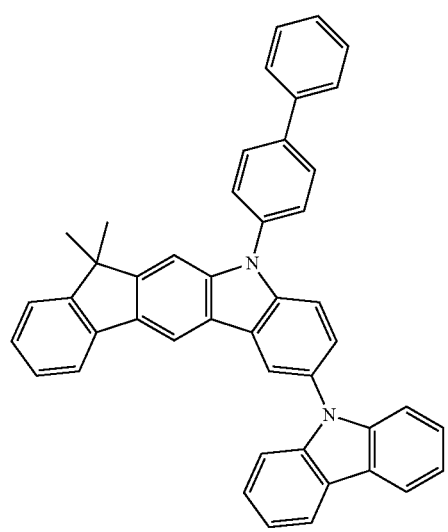
B-53
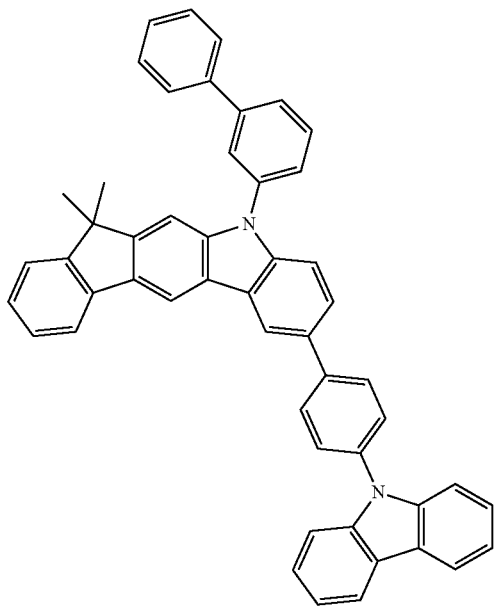
B-54
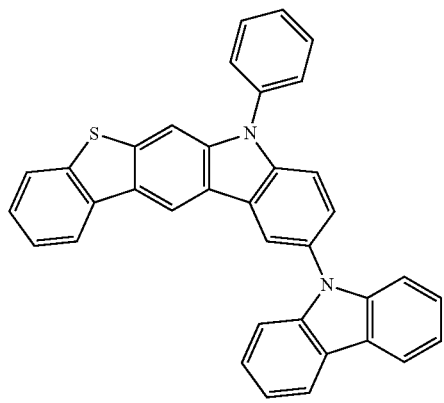
B-55
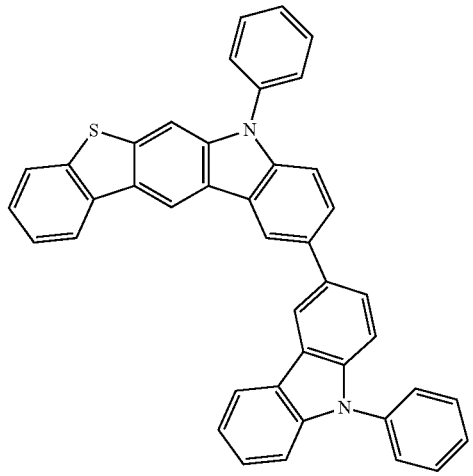

B-56
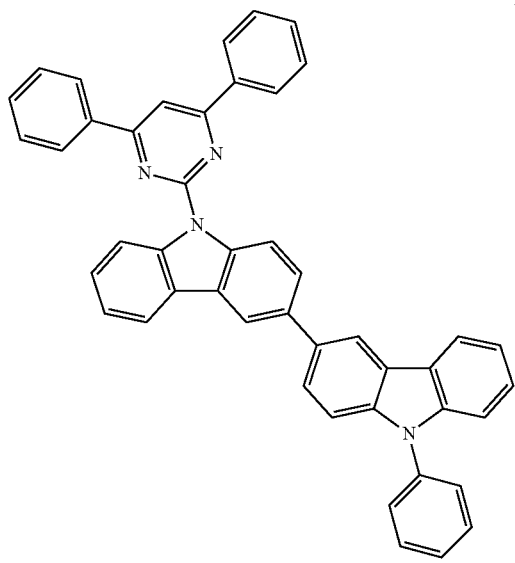
B-57
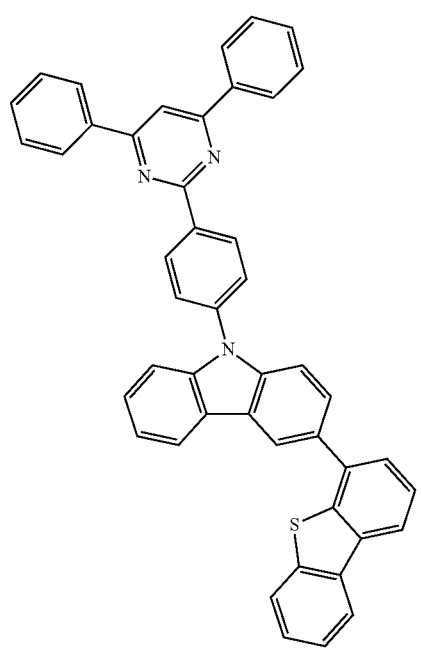
B-58
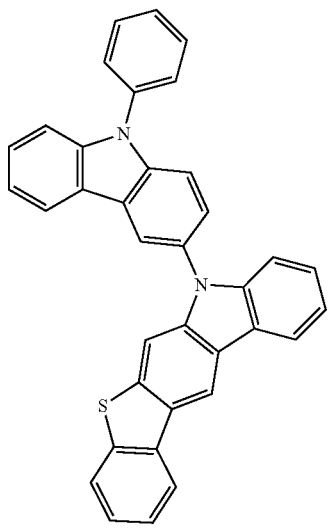
B-59
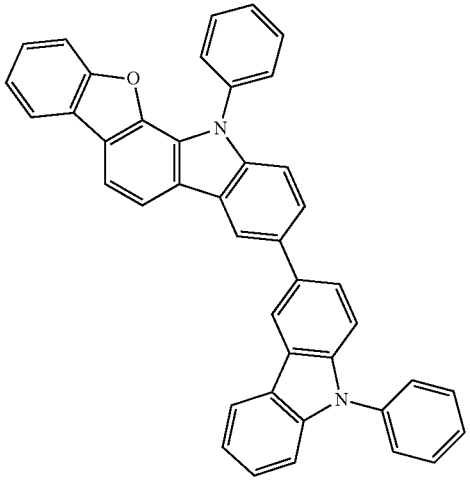
B-60

B-61
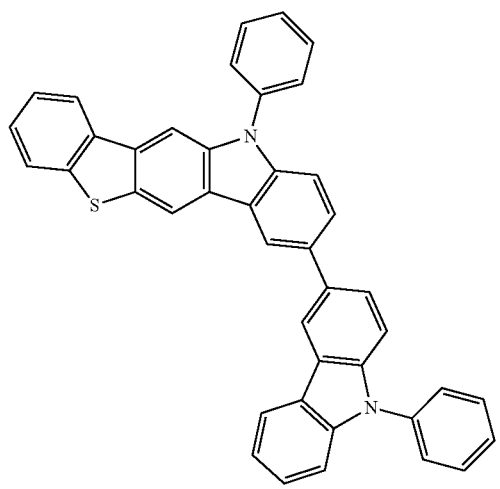
B-62
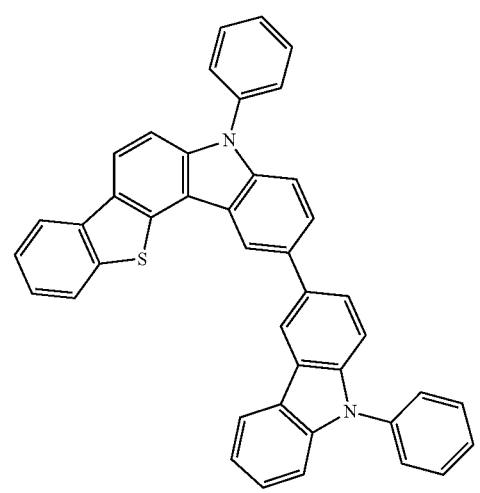
B-63
B-64
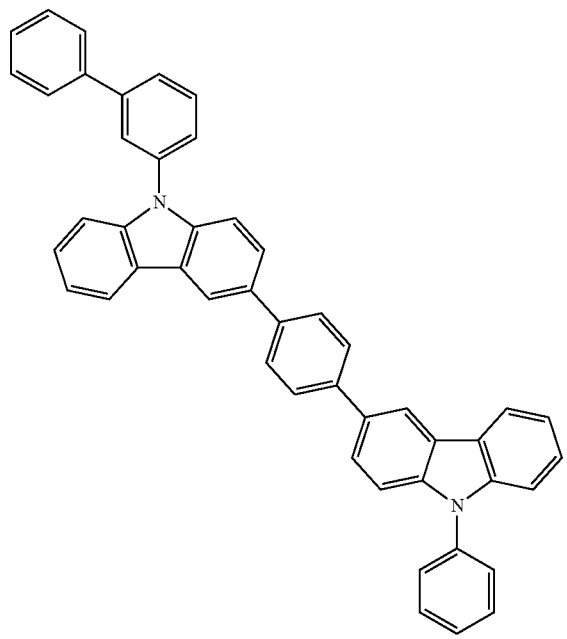
B-65
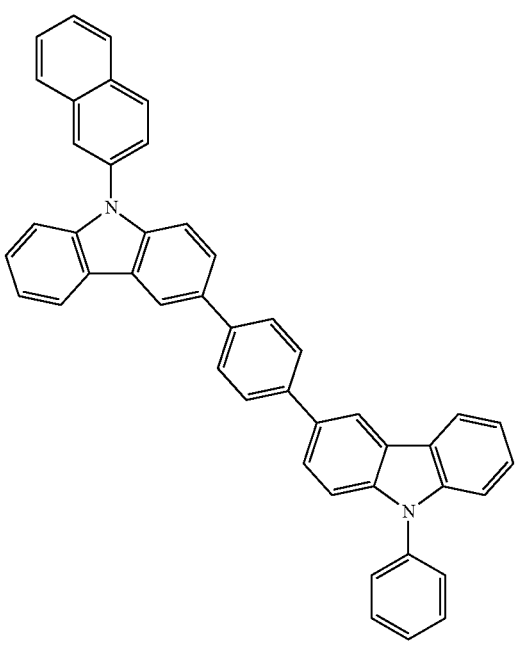

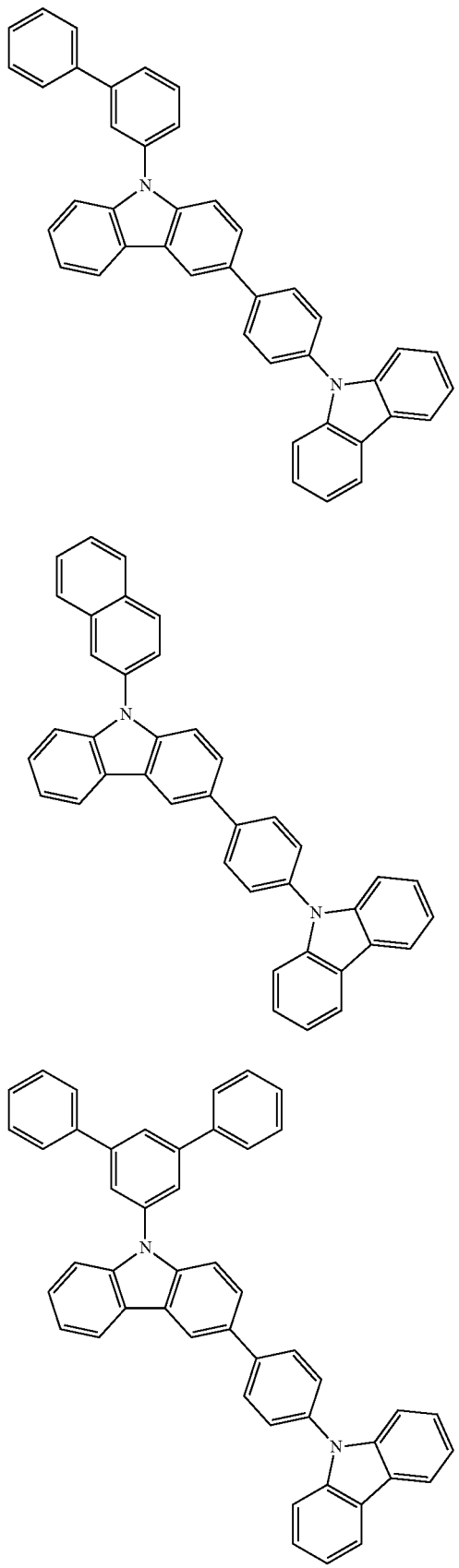
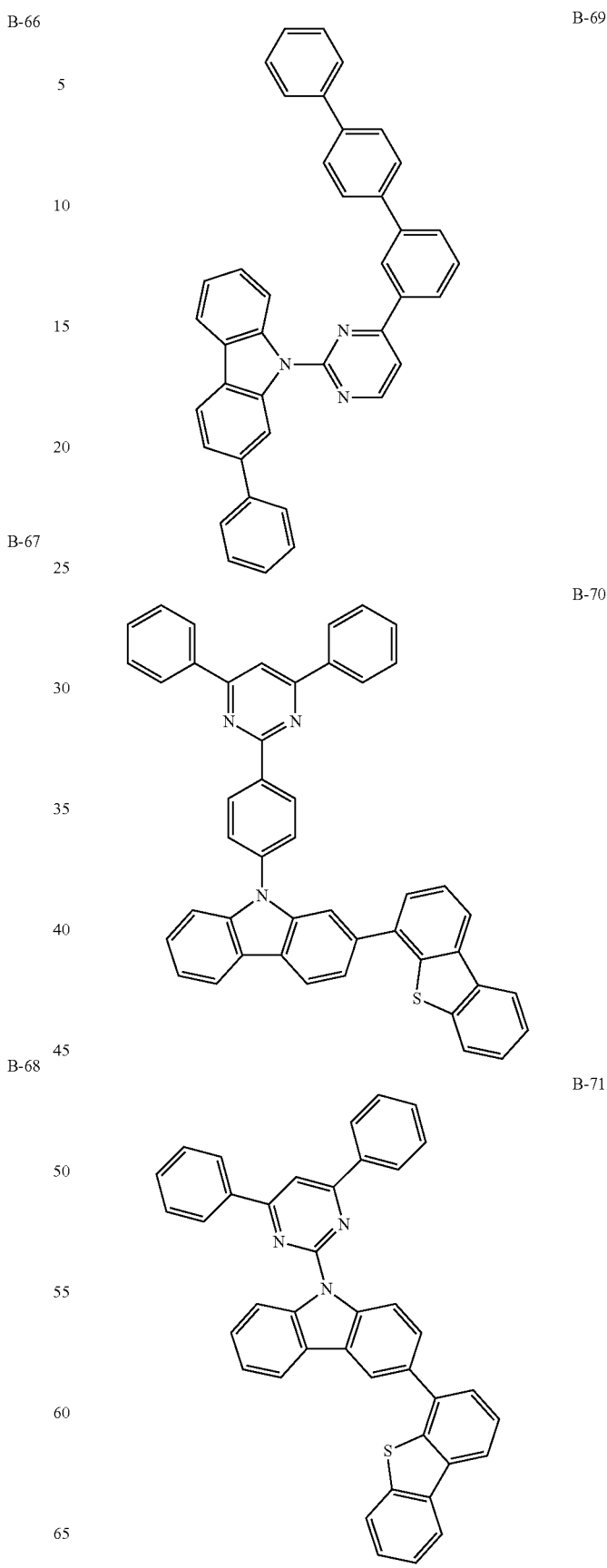

B-72
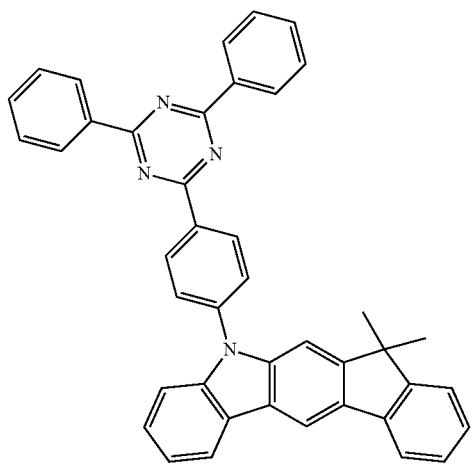
B-73
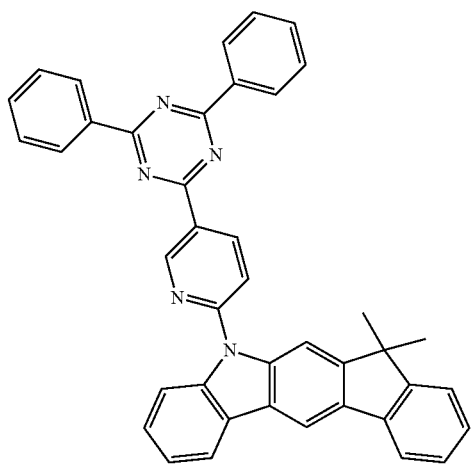
B-74
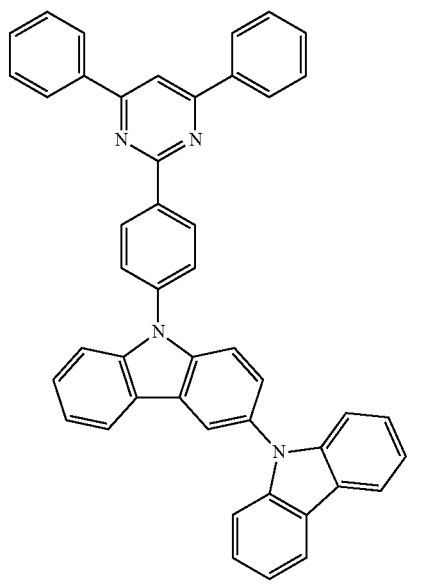
B-75
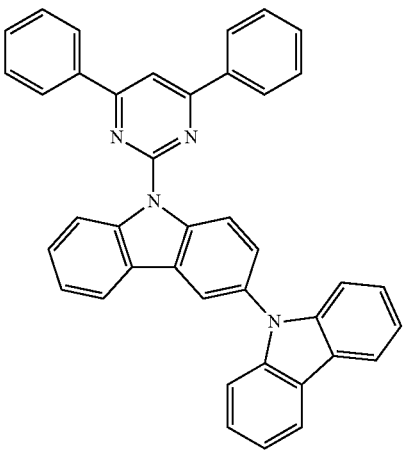
B-76
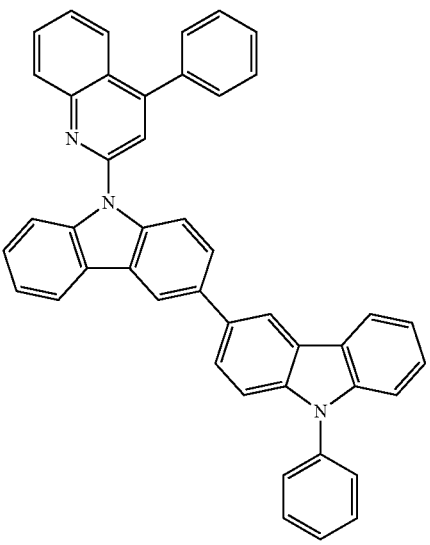
B-77
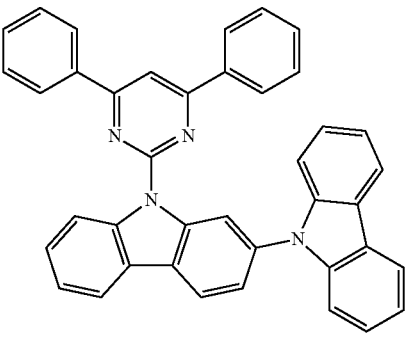

B-78
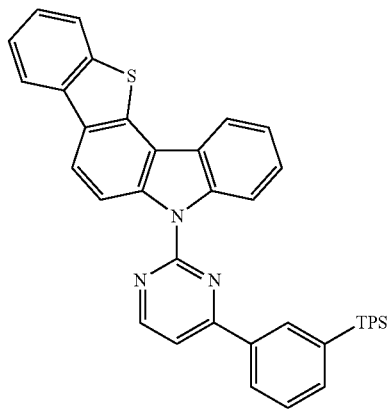
B-79
B-80
B-81
B-82
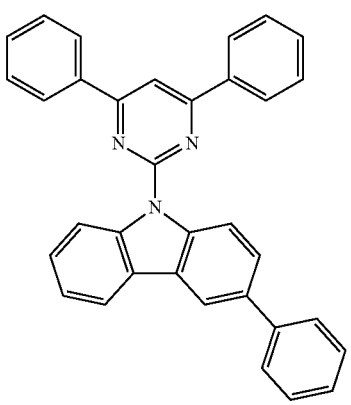
B-83
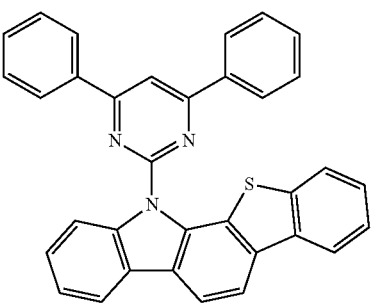
B-84
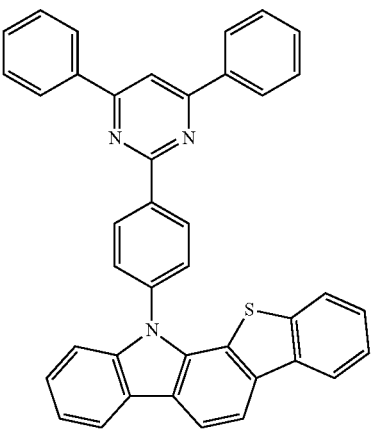
B-85
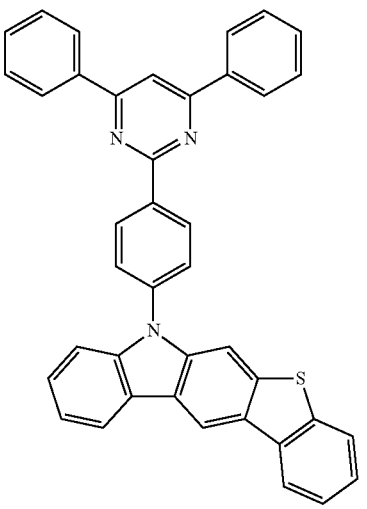

-continued
B-86
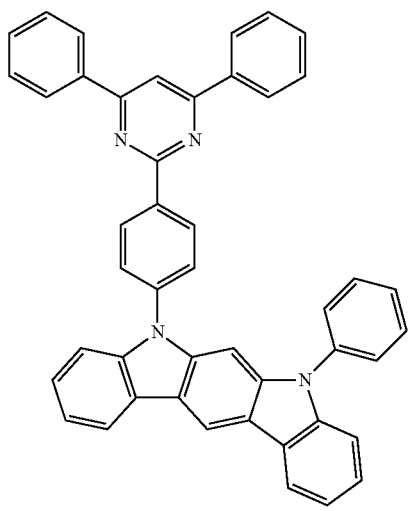
B-87
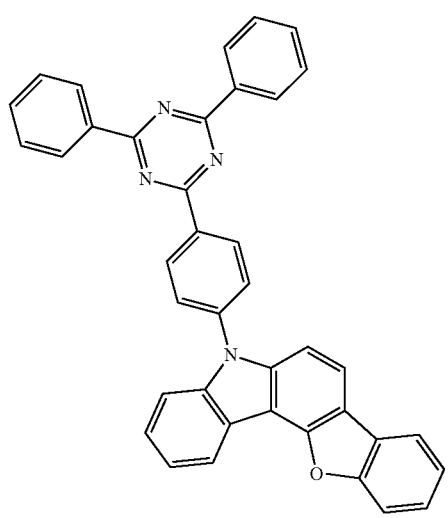
B-88
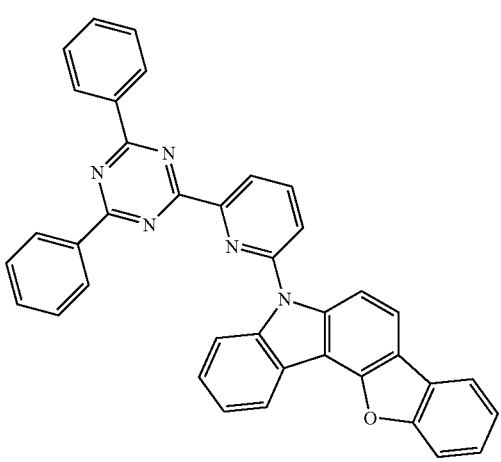
-continued
B-89
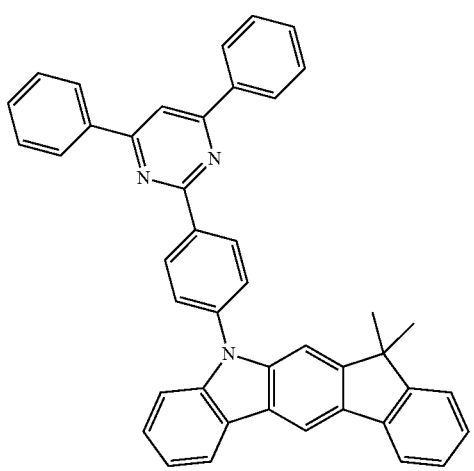
B-90
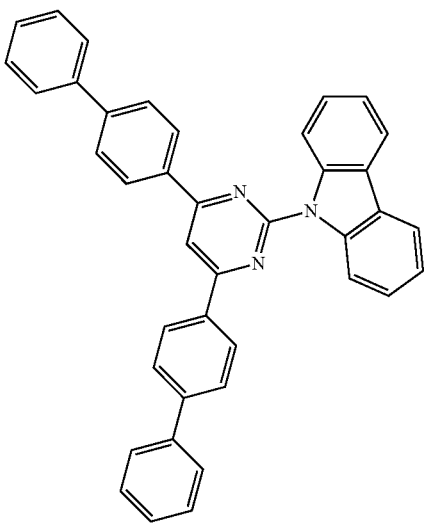
B-91
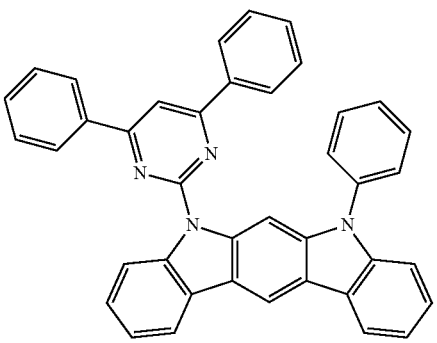

B-92
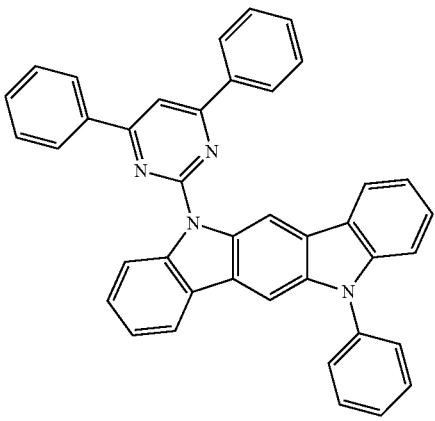
B-93
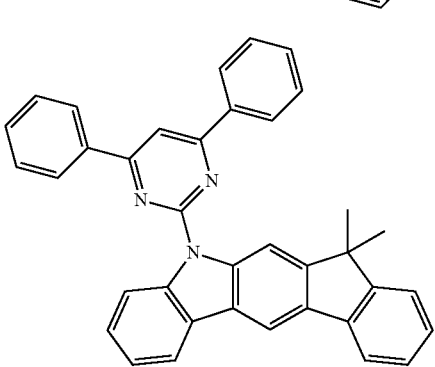
B-94
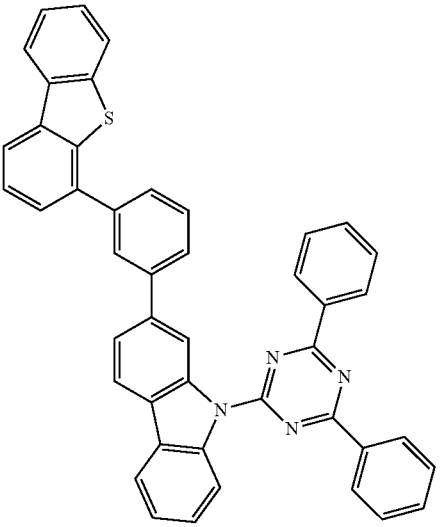
B-95
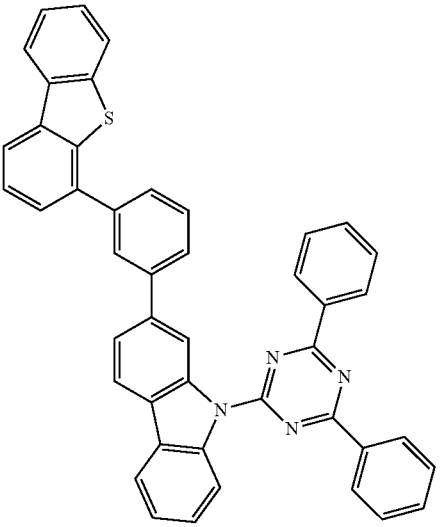
B-96
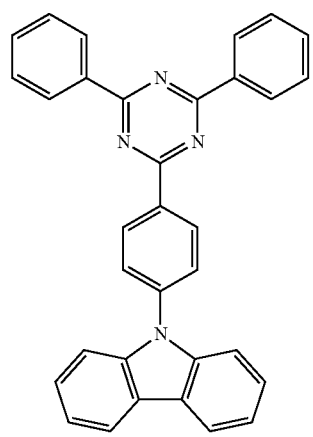
B-97
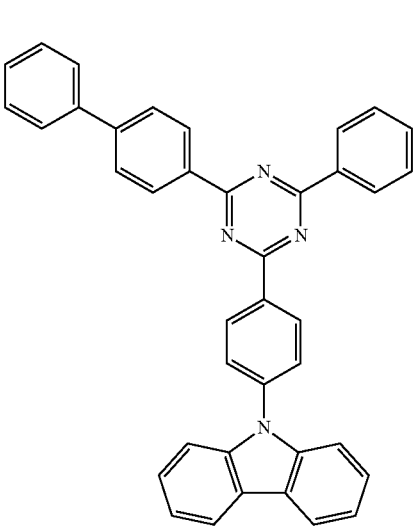
B-98
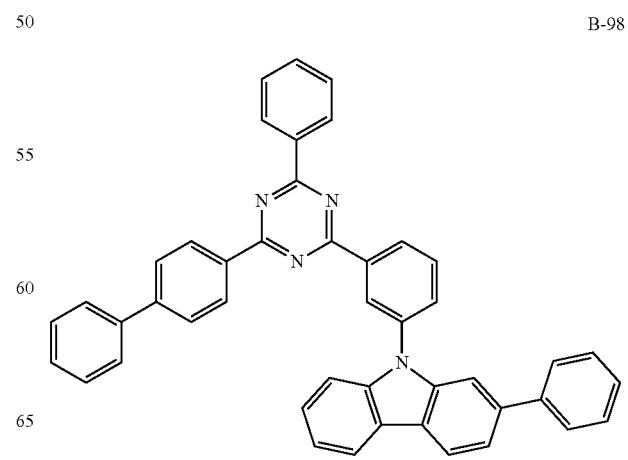

B-99
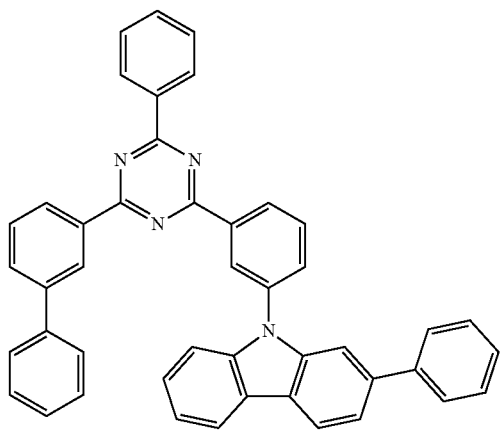
B-102
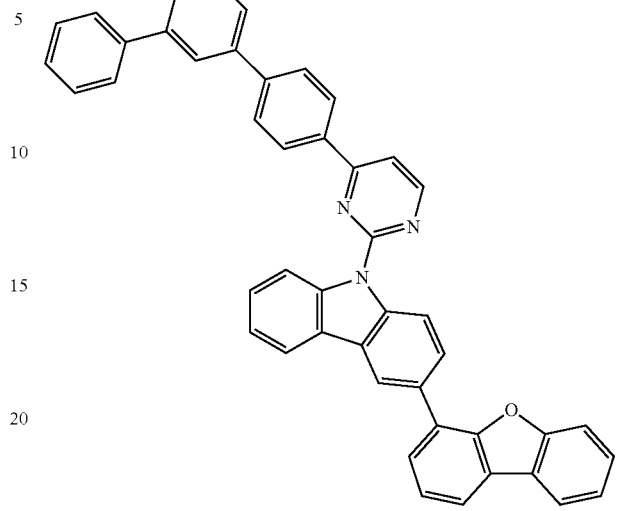
B-100
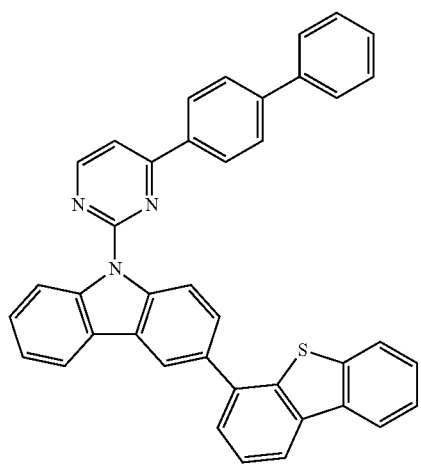
B-103
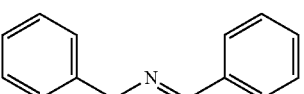
B-101
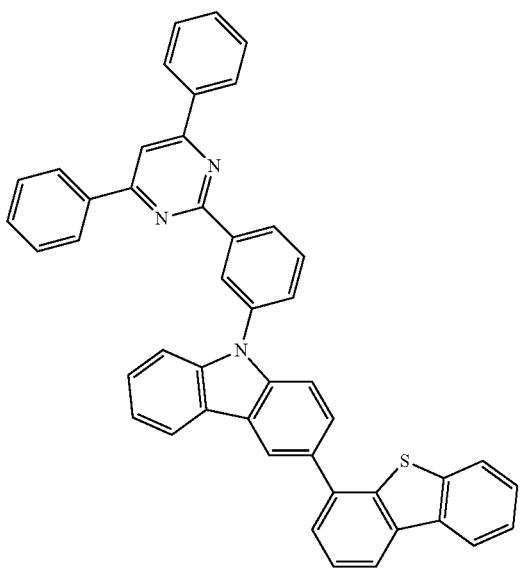
B-104
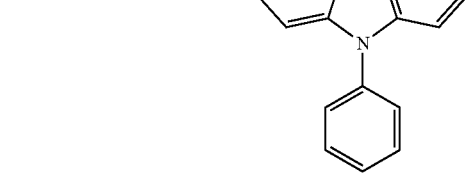

B-105
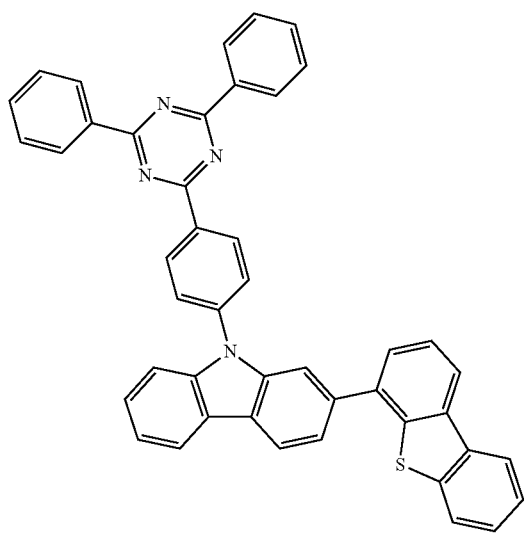
B-106
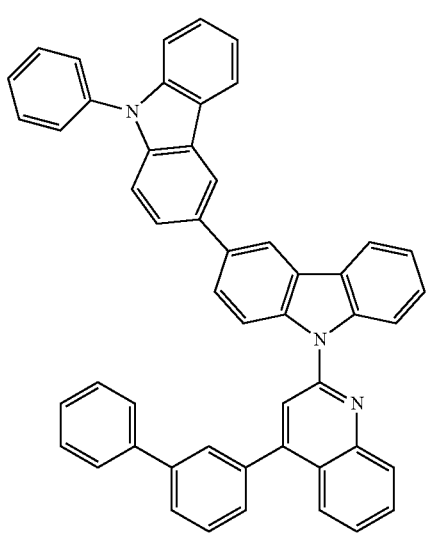
B-107
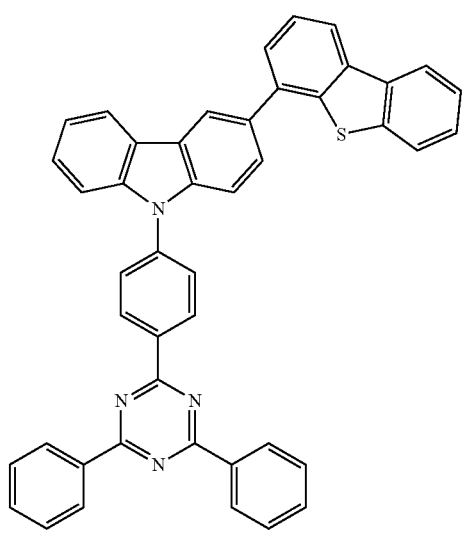
B-108
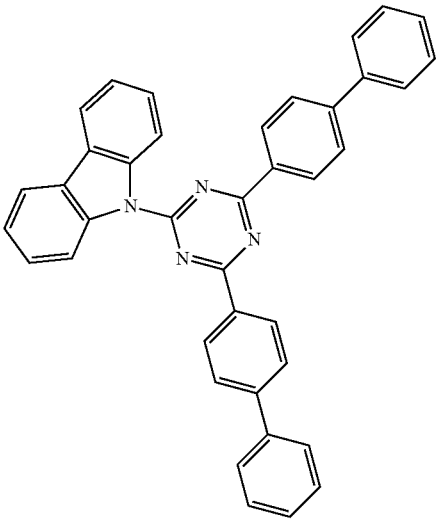
B-109
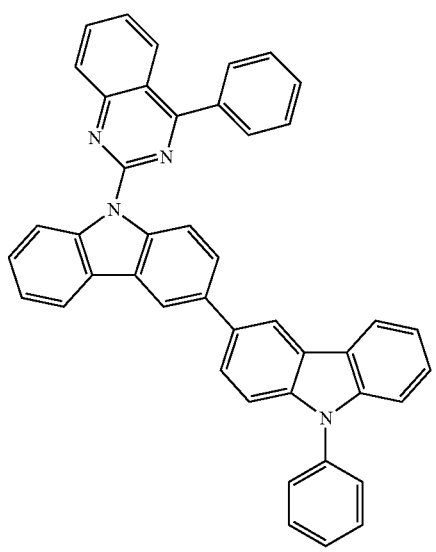
B-110
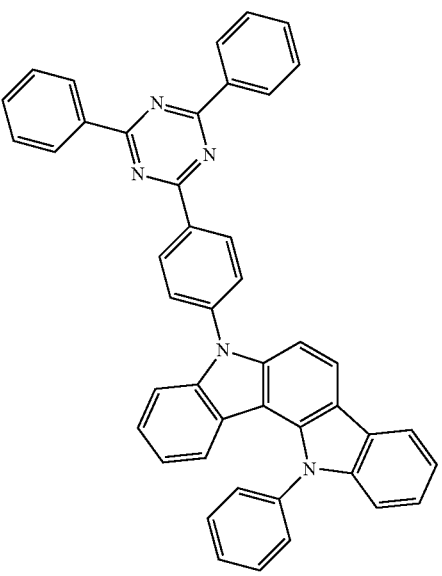

B-111
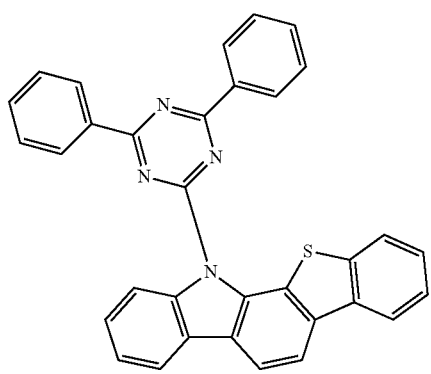
B-112
B-113
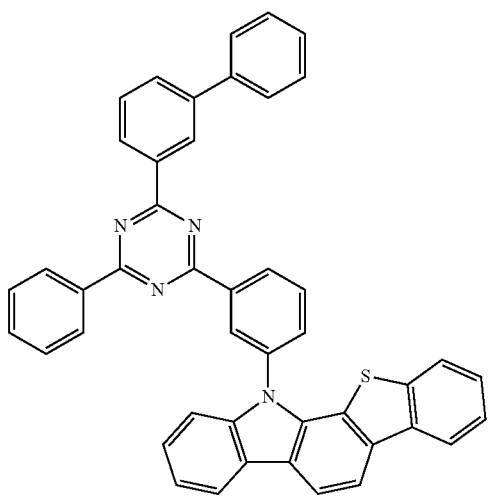
B-114
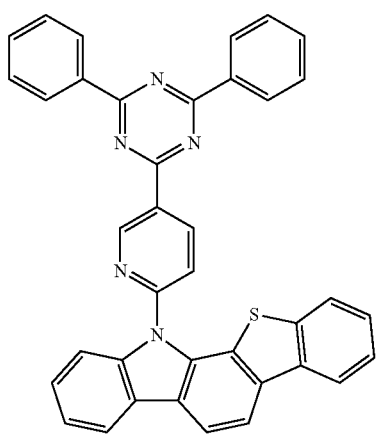
B-115
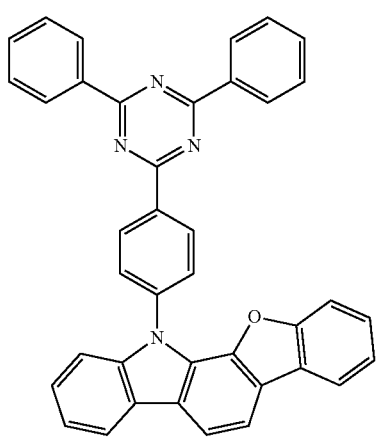
B-116
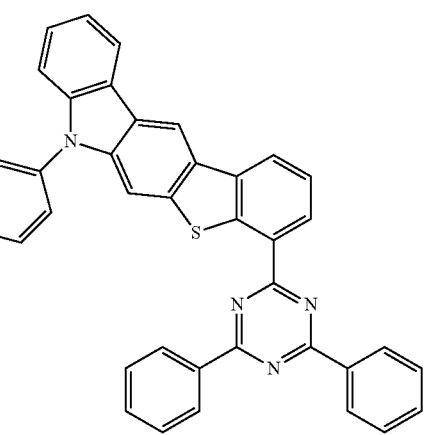

B-117
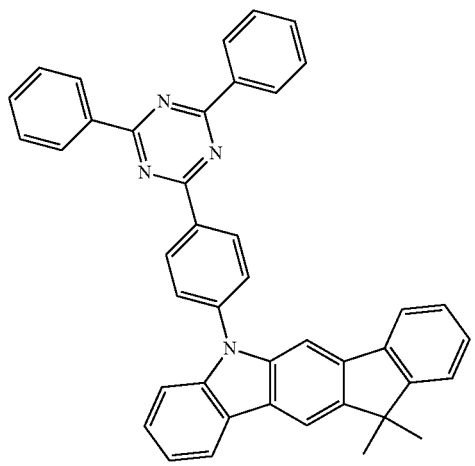
B-118
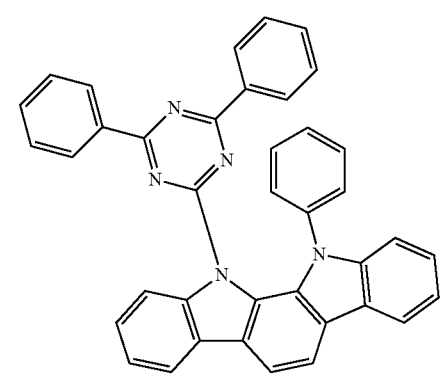
B-119
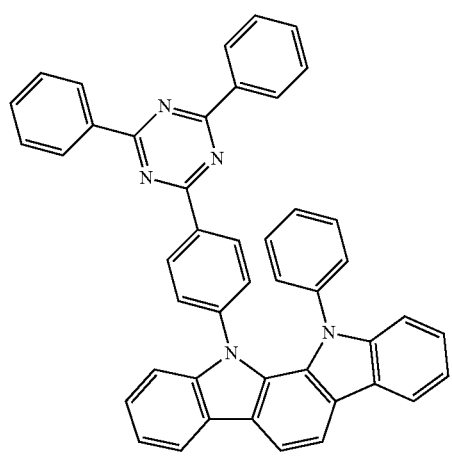
B-120
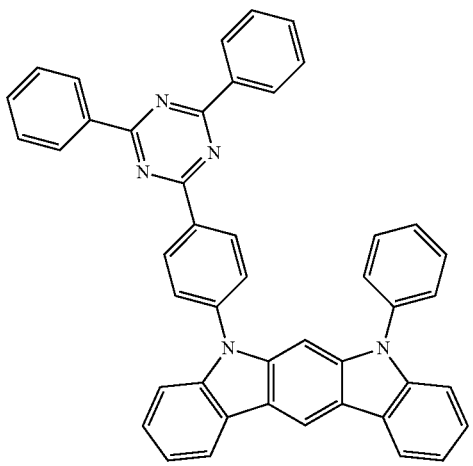
B-121
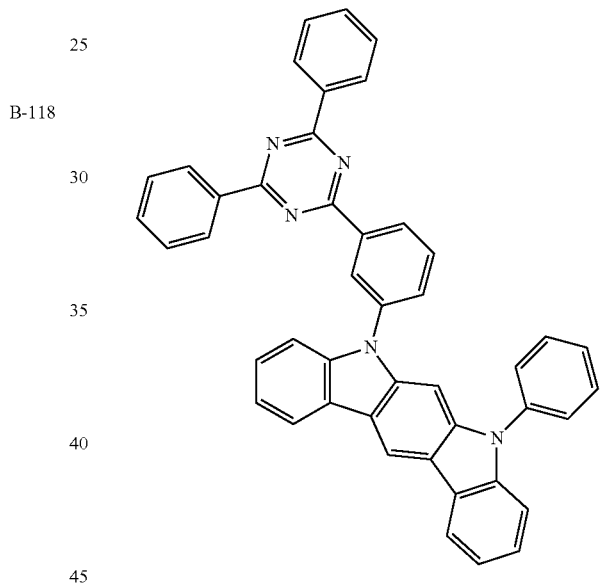
B-122
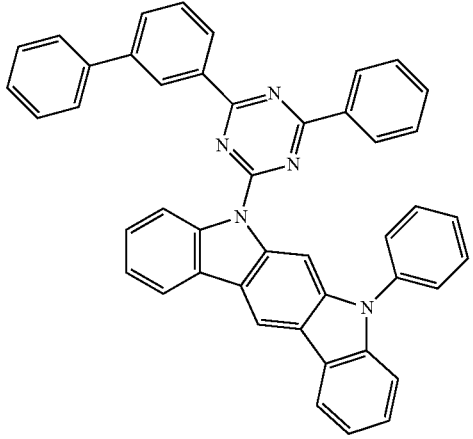

B-123
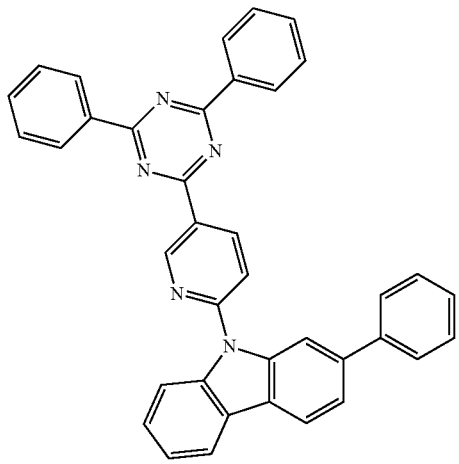
B-124
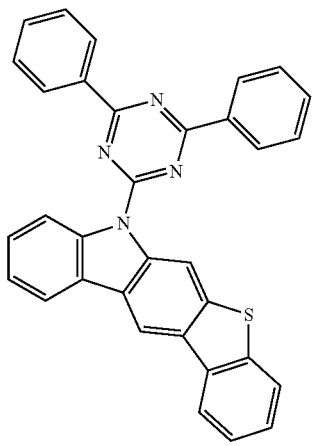
B-125
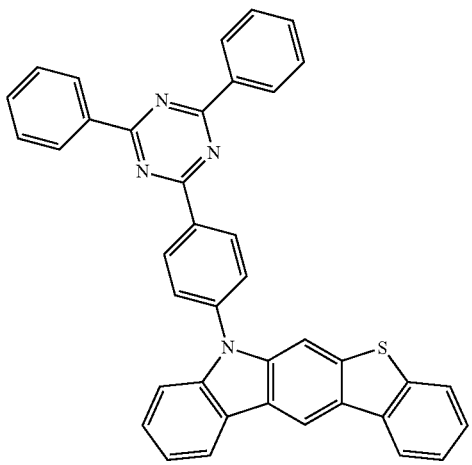
B-126
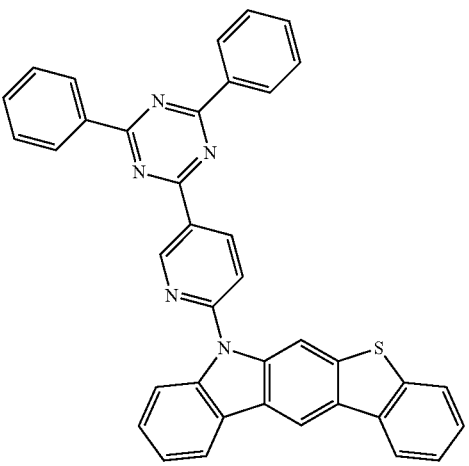
B-127
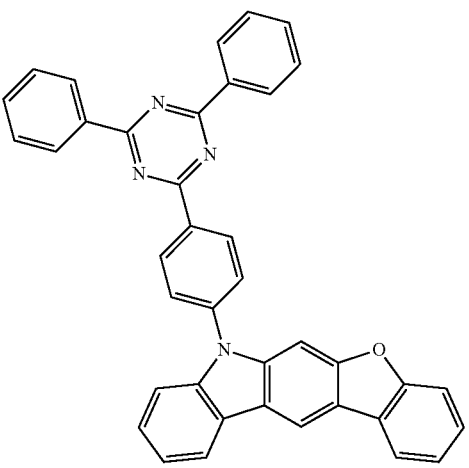
B-128
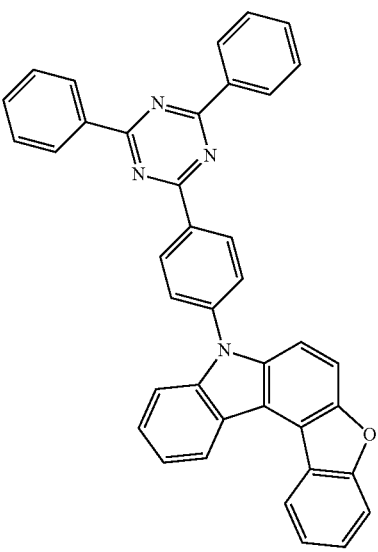

B-129
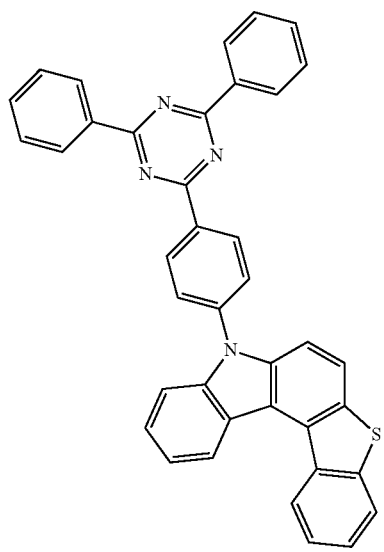
B-130
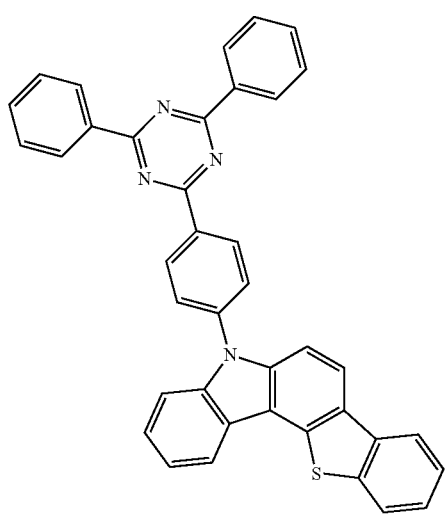
B-131
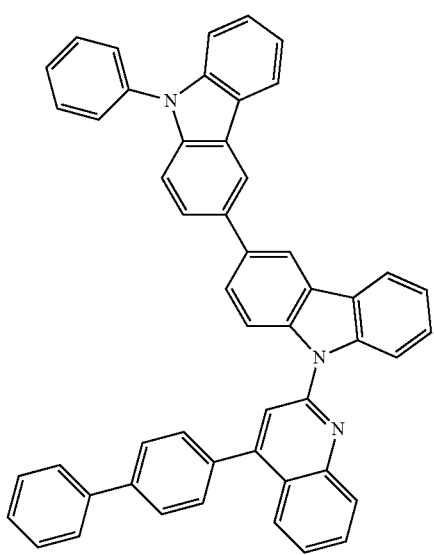
B-132
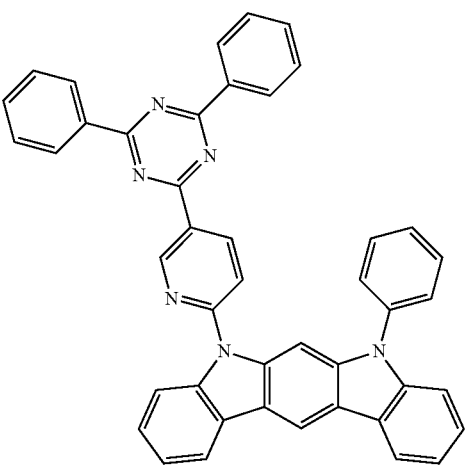
B-133
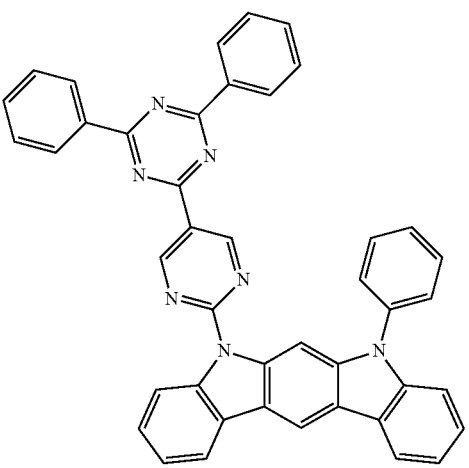
B-134
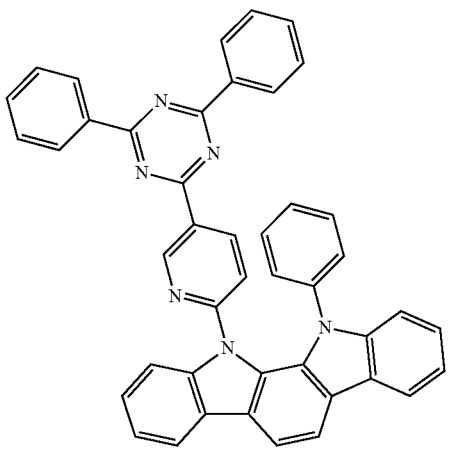

B-135
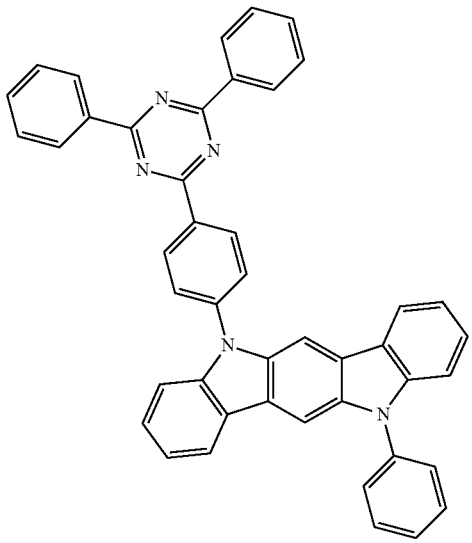
B-136
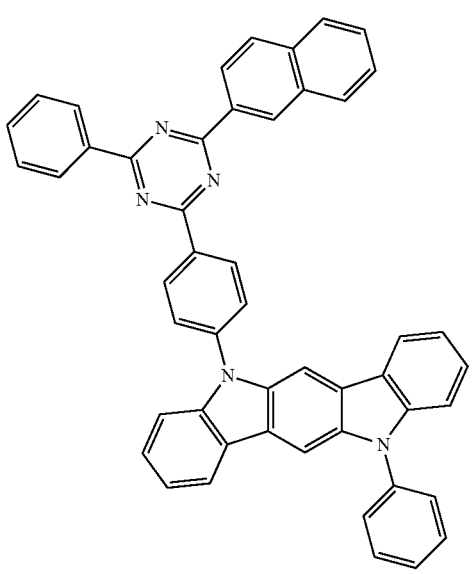
B-137
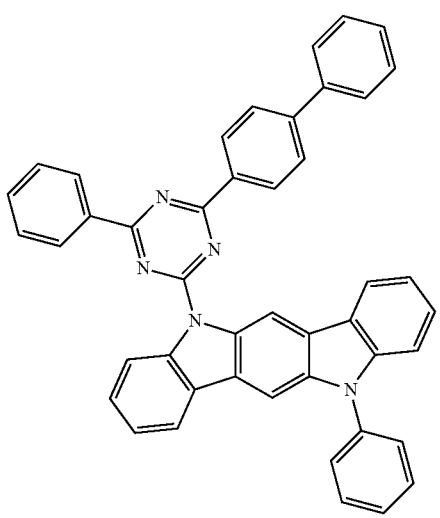
B-138
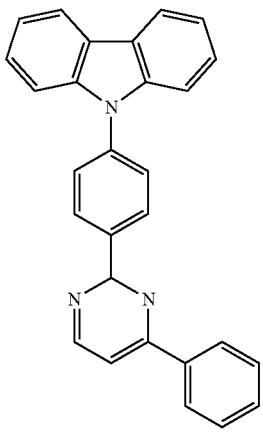
B-139
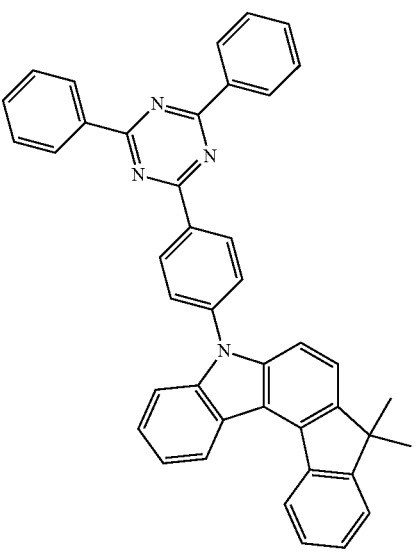
B-140
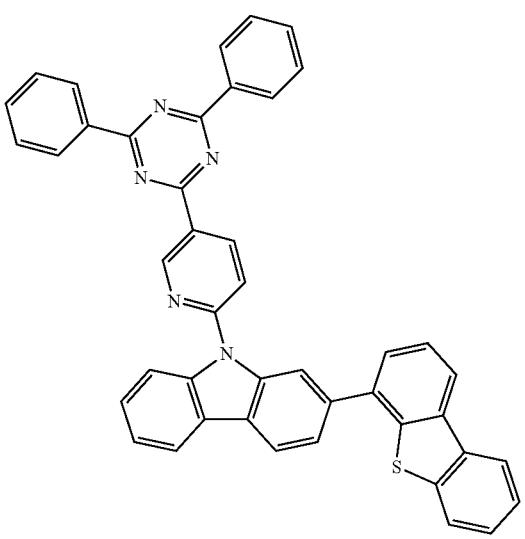

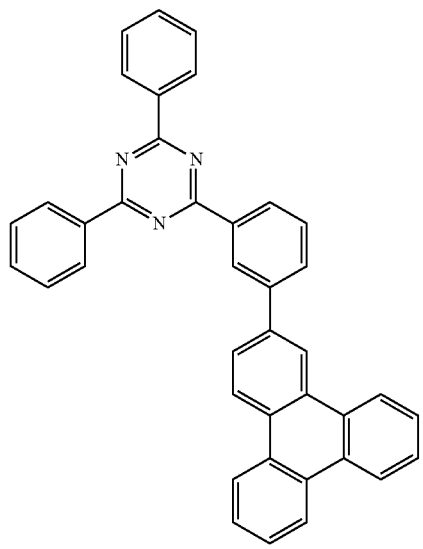
B-141
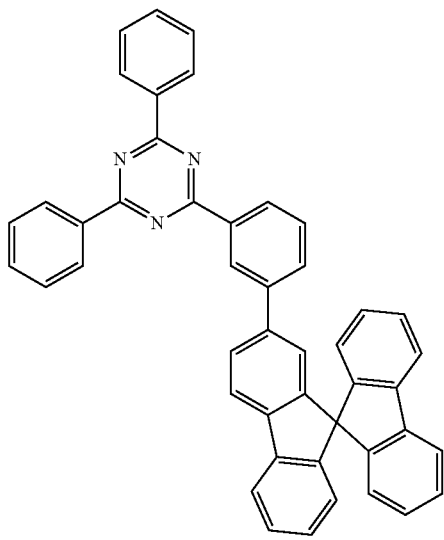
B-143
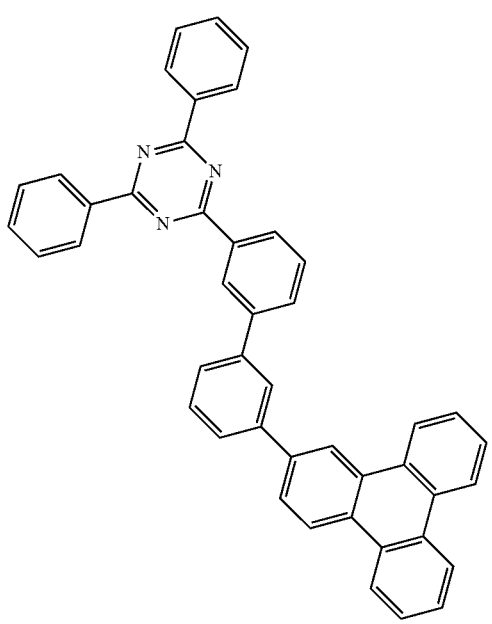
B-142
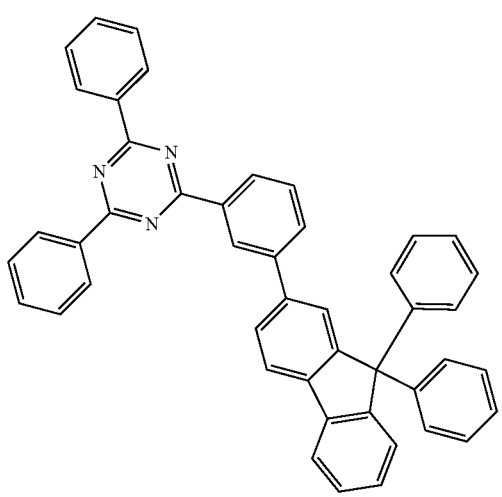
B-144
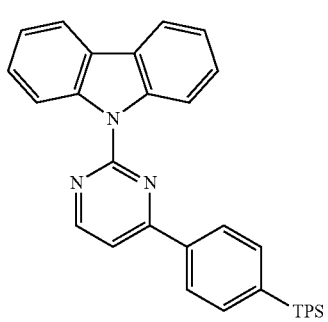
B-145

B-146
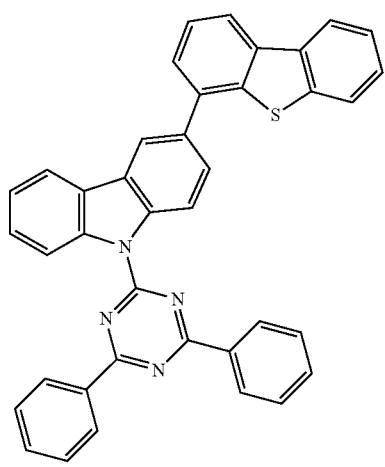
B-149
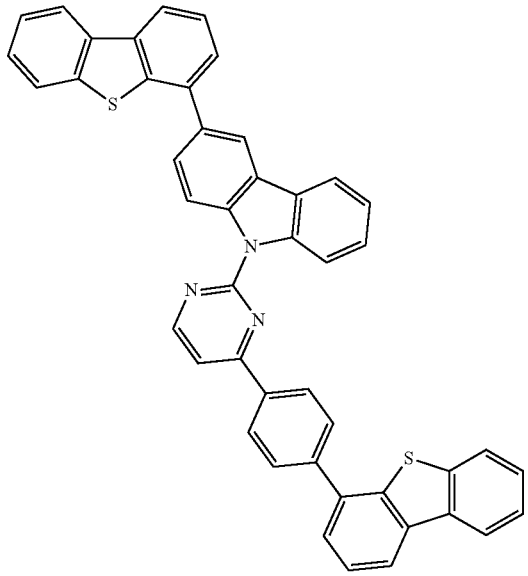
B-147
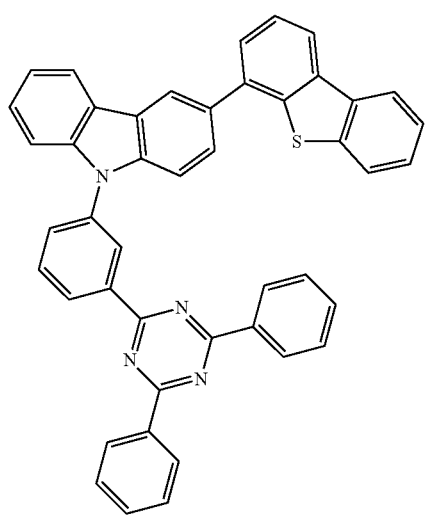
B-150
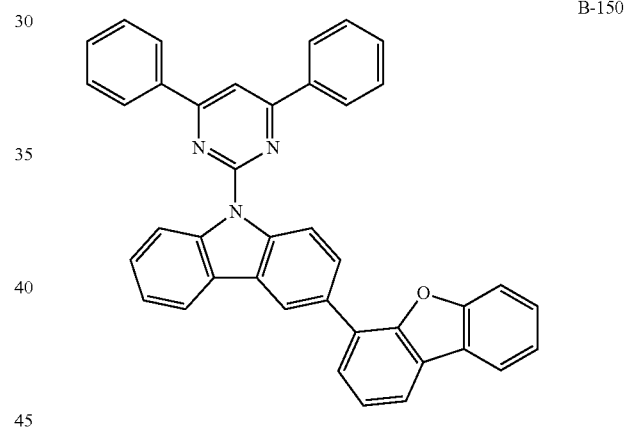
B-148
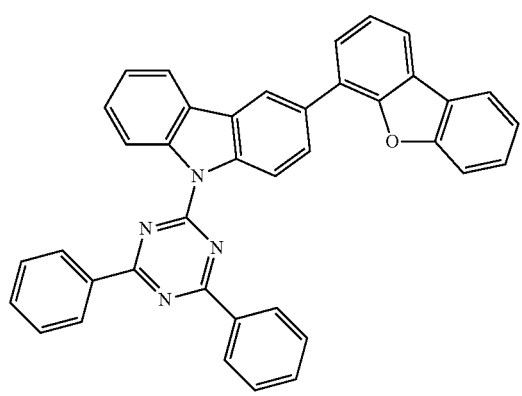
B-151
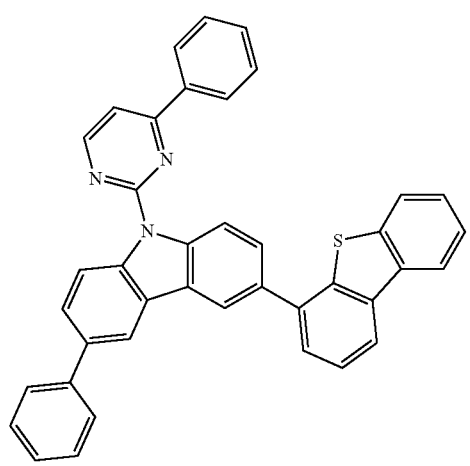

B-152
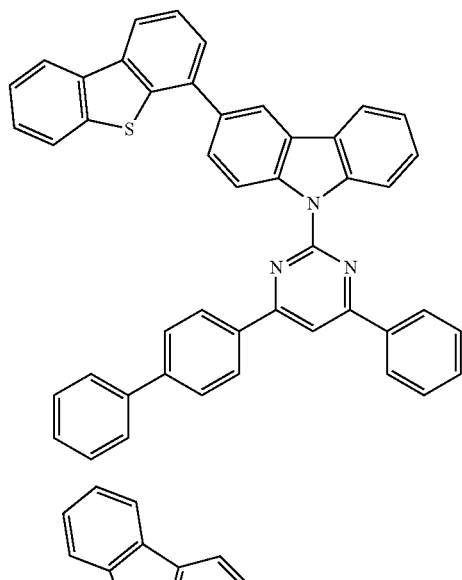
B-153
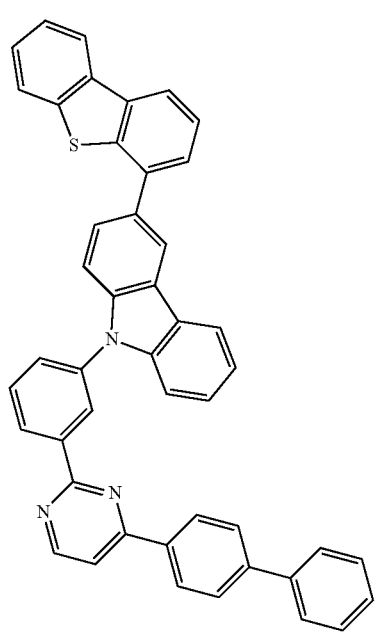
B-154
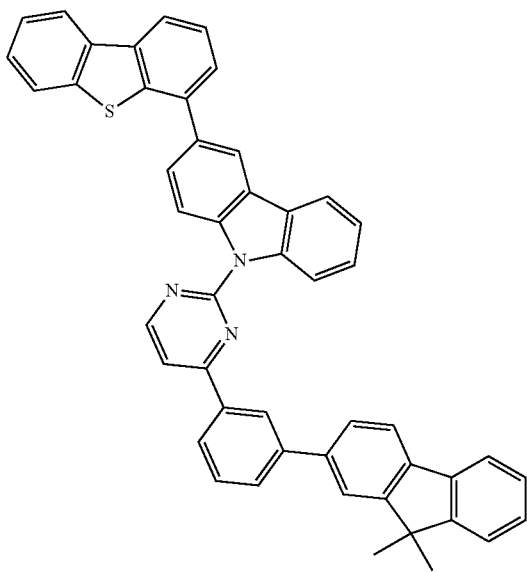
B-155
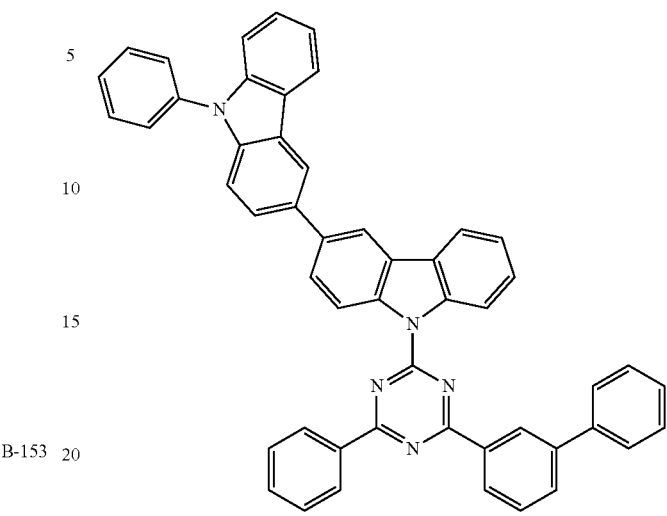
B-156
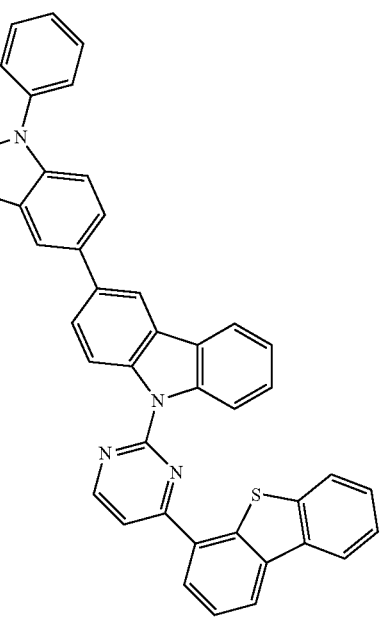

B-157
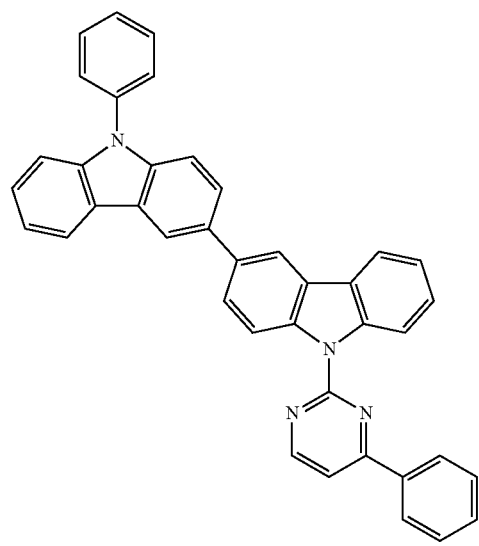
B-159
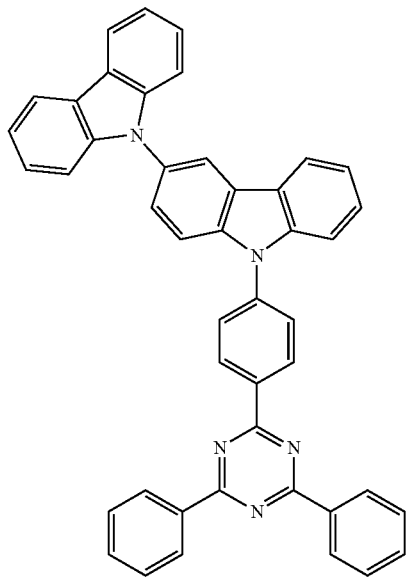
B-160
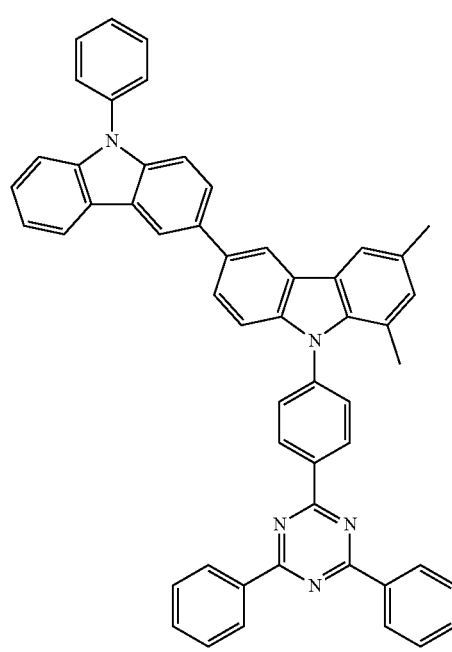
B-158
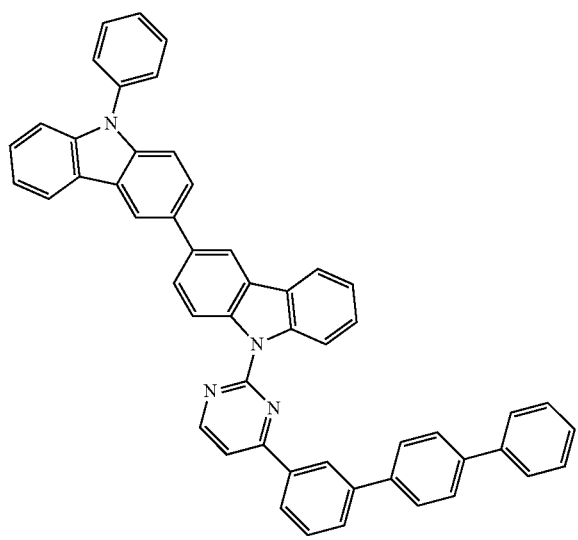
B-161
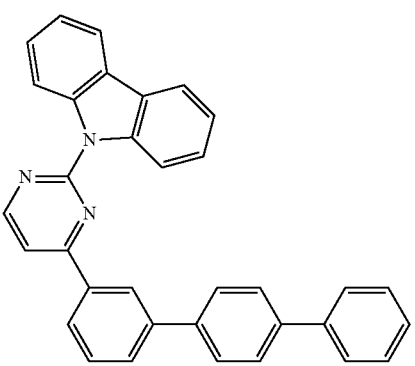

B-162
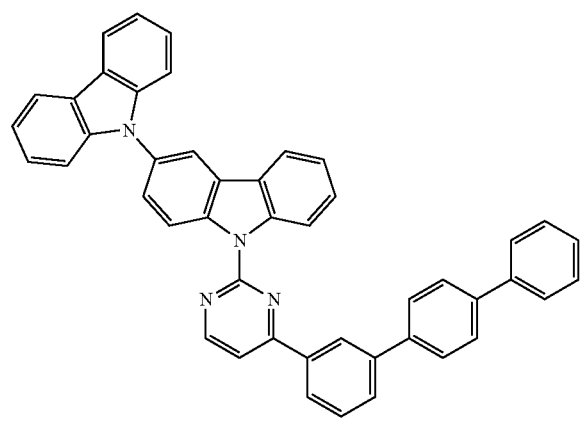
B-163
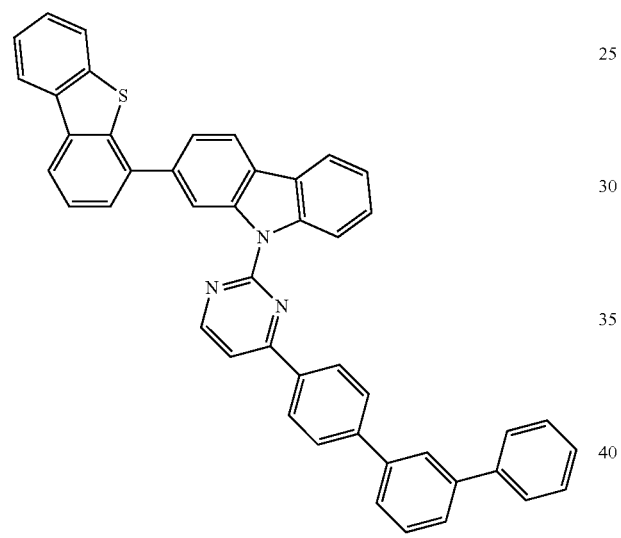
B-164
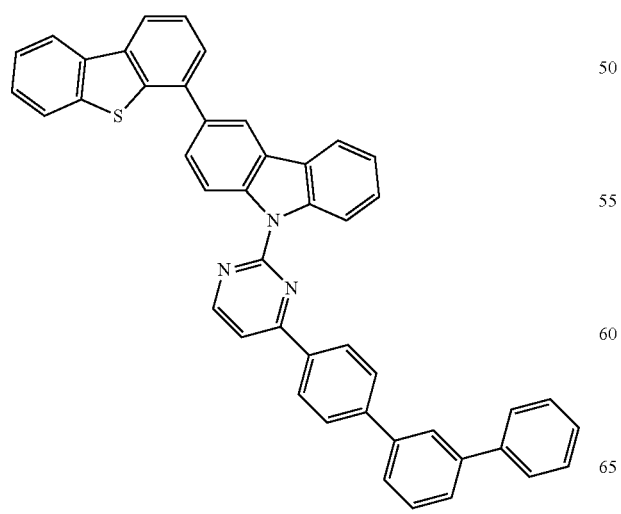
B-165
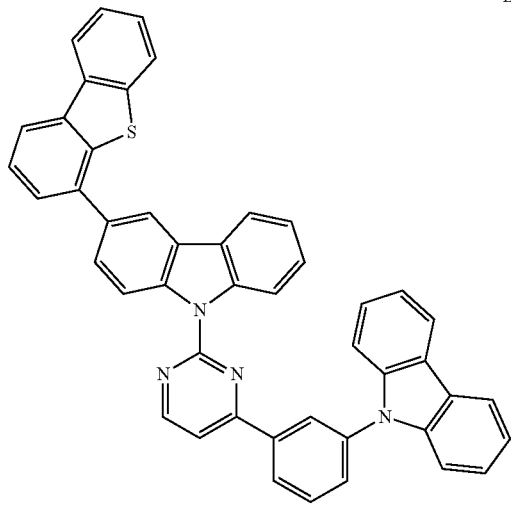
B-166
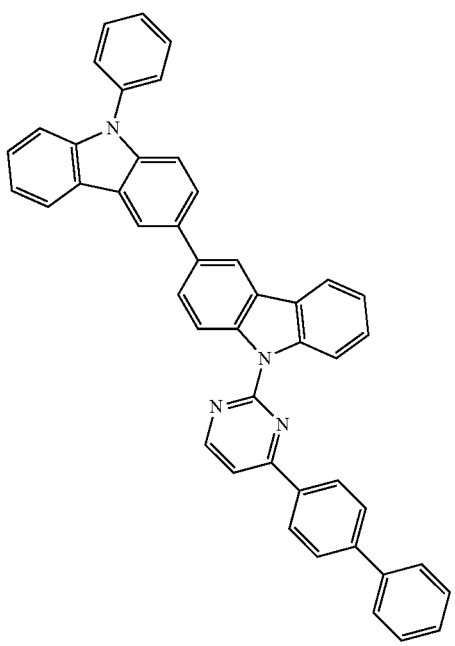

B-167
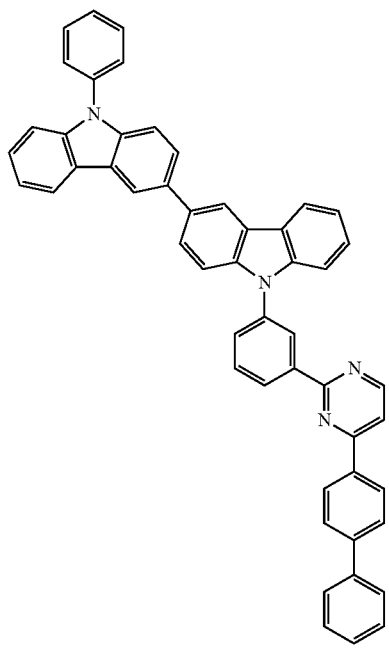
B-169
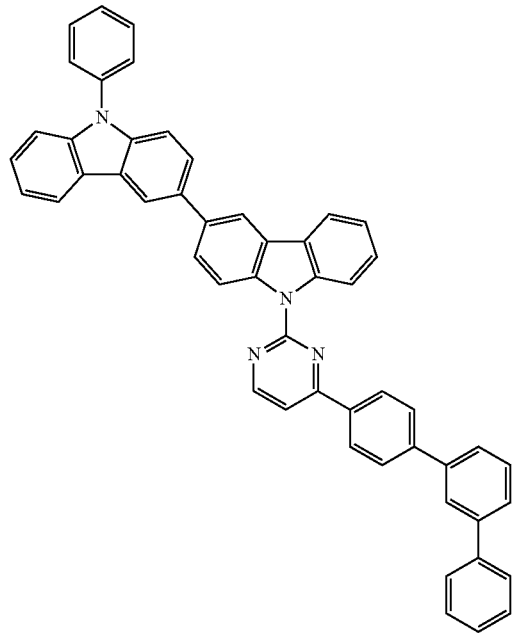
B-168
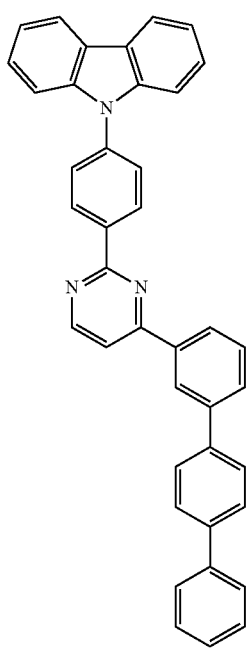
B-170
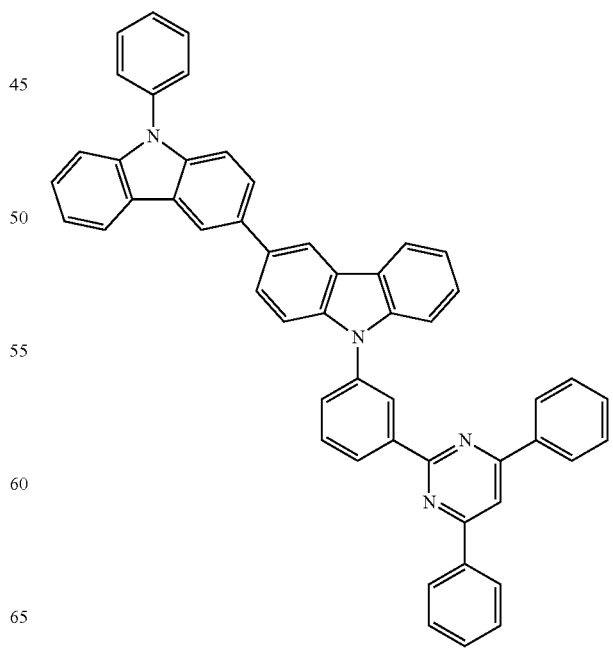

B-171
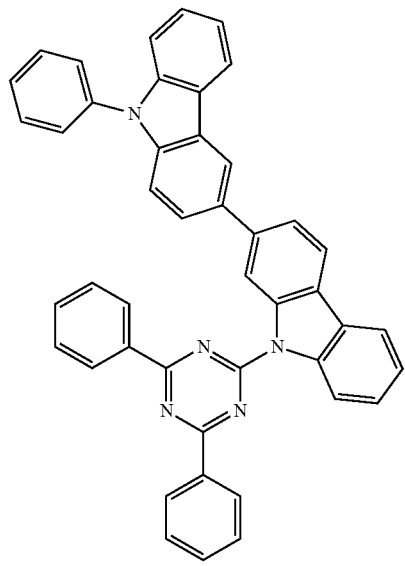
B-172
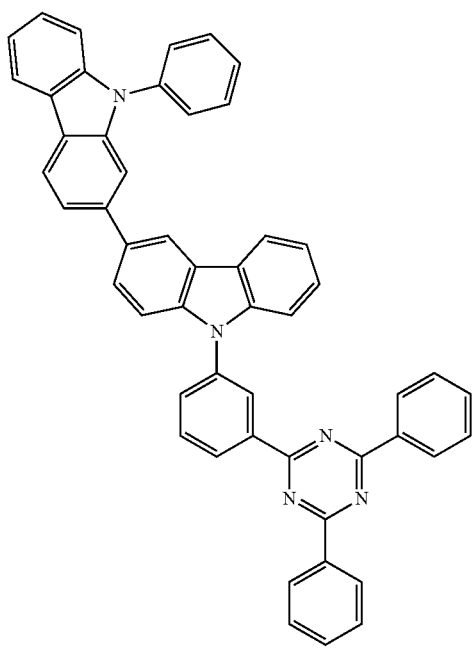
B-173
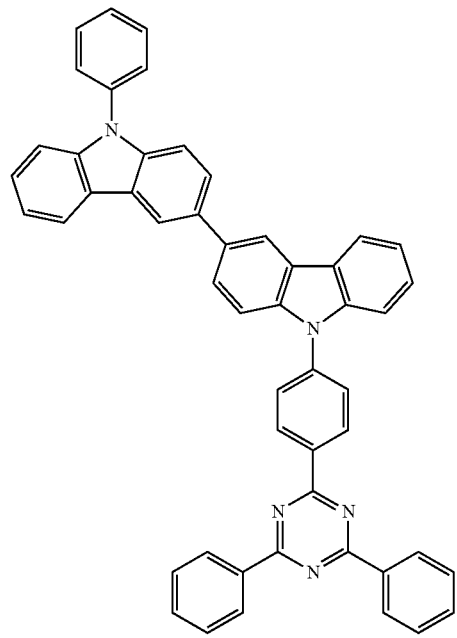
B-174
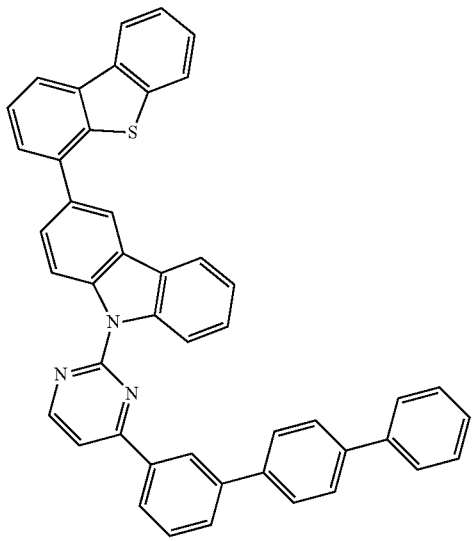

B-175
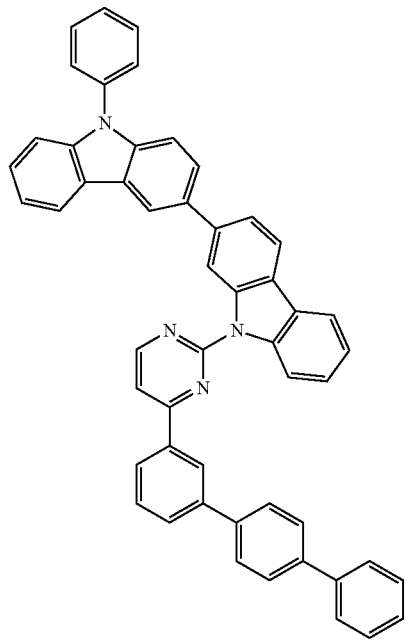
B-176
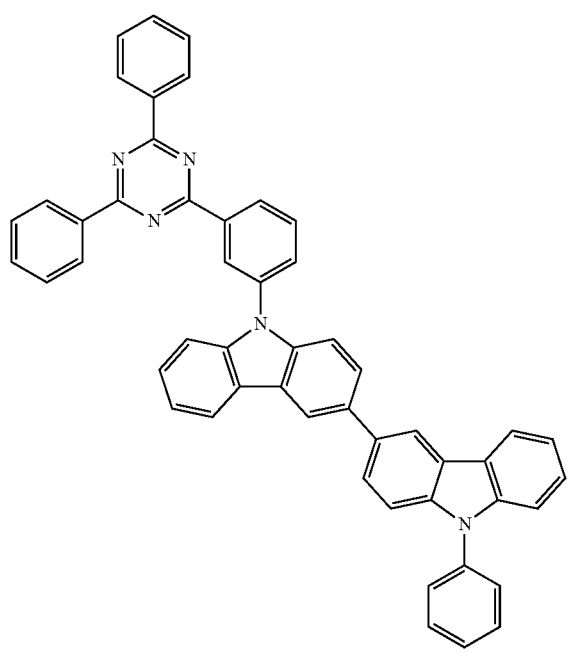
B-177
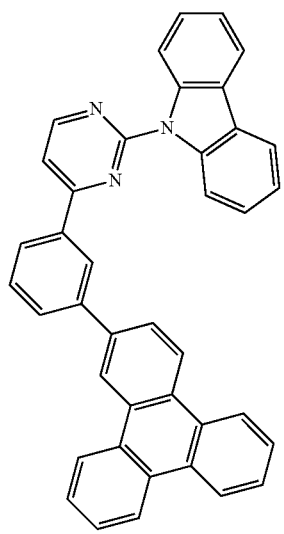
B-178
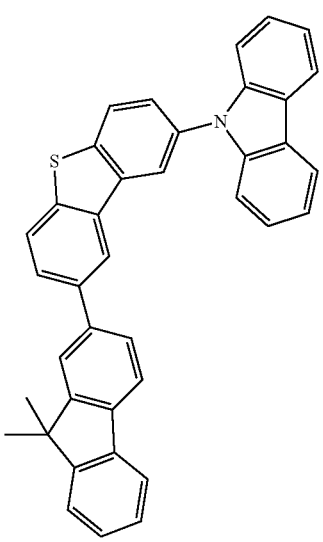
B-179
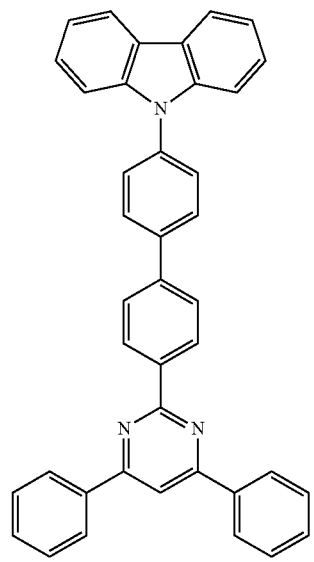

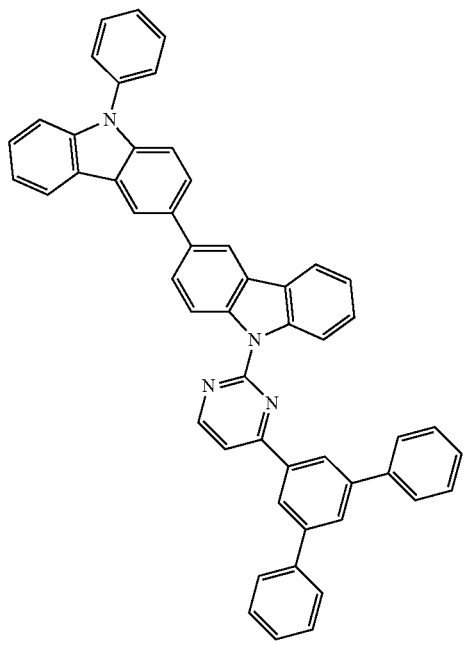
B-180
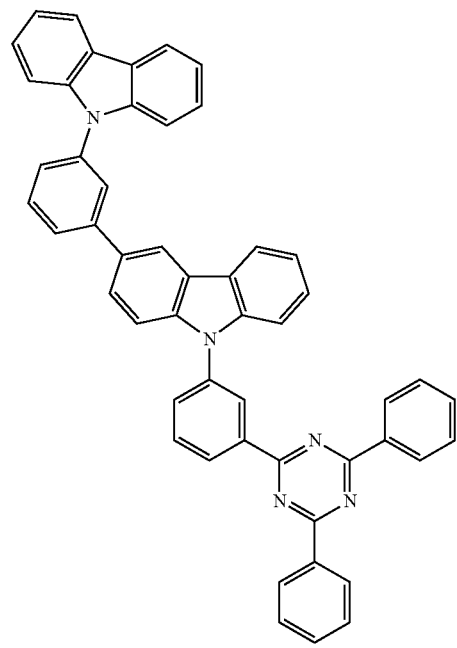
B-182
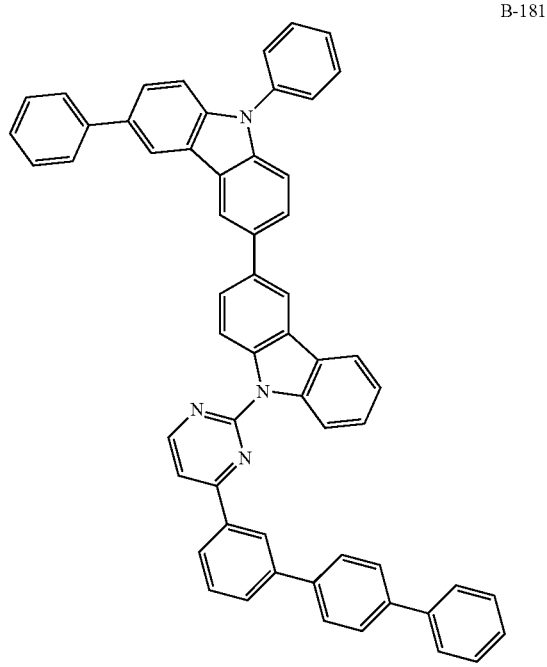
B-181
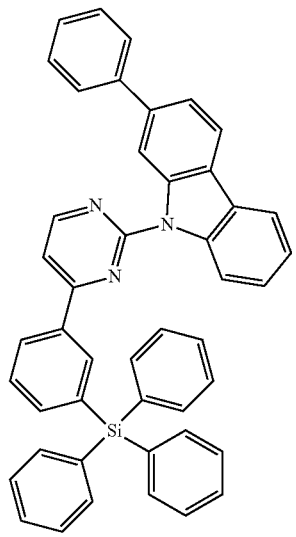
B-183

B-184
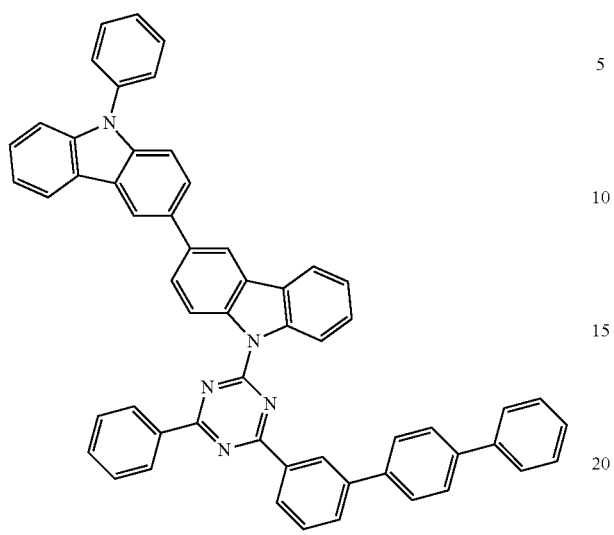
B-185
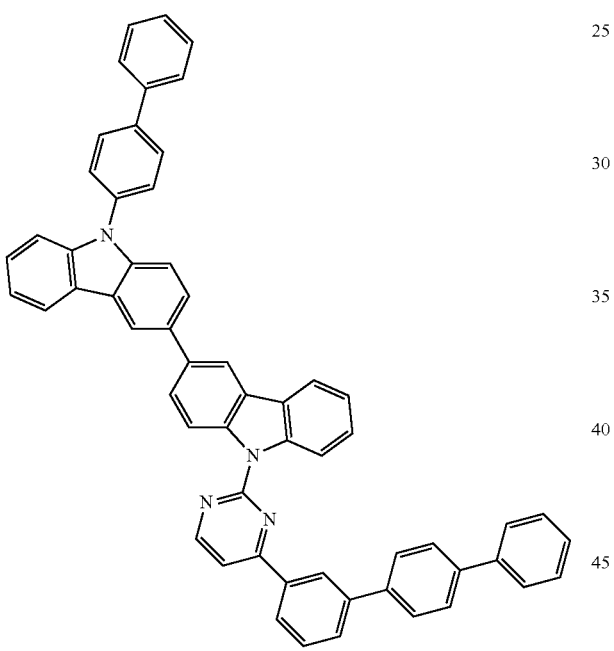
B-186
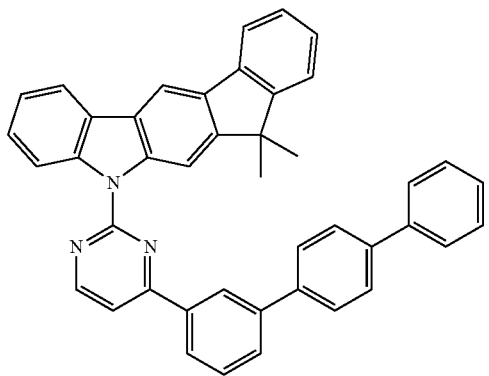
B-187
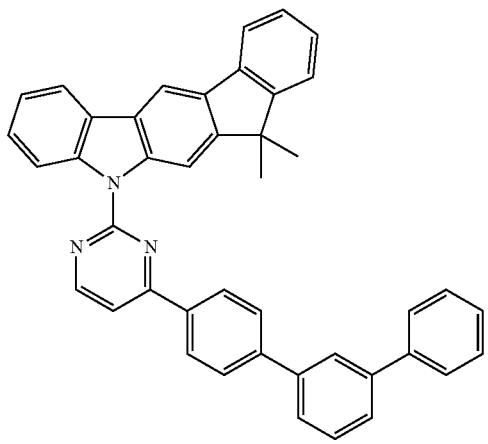
B-188
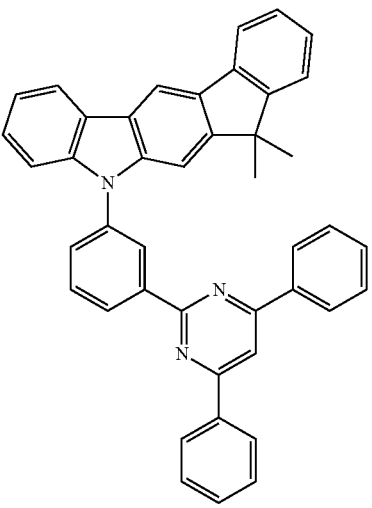
B-189
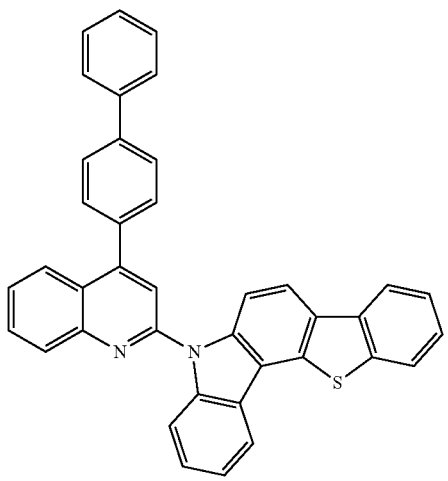

B-190
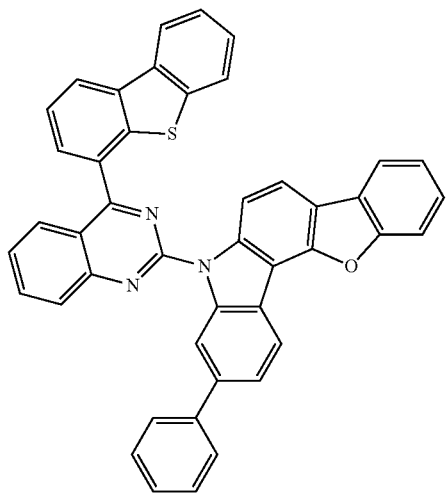
B-193
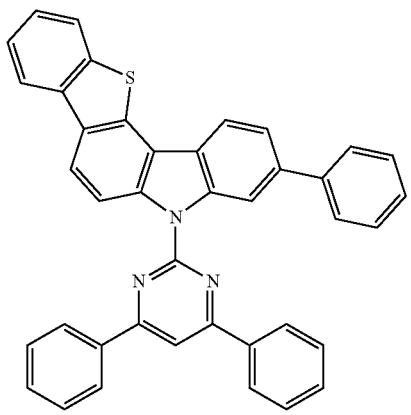
B-191
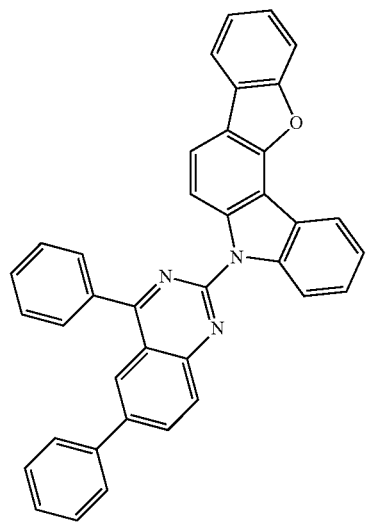
B-194
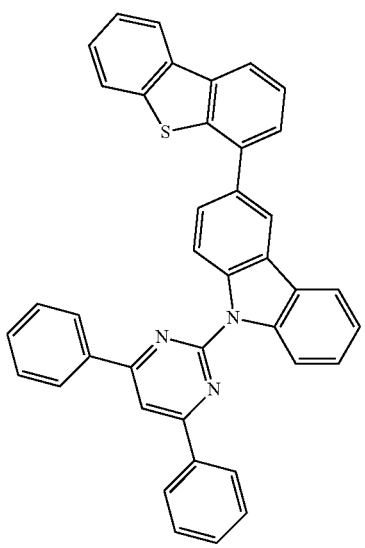
B-192
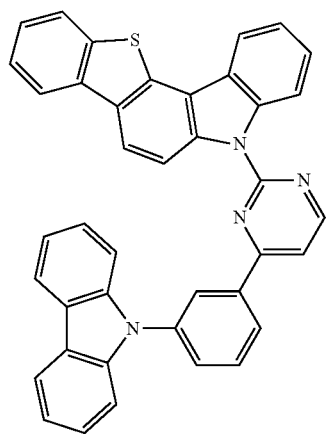
B-195
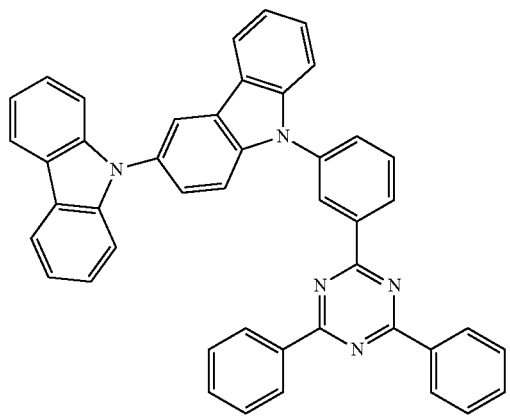

B-196

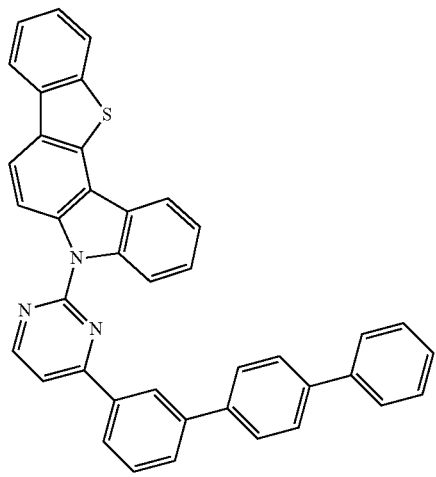

B-197

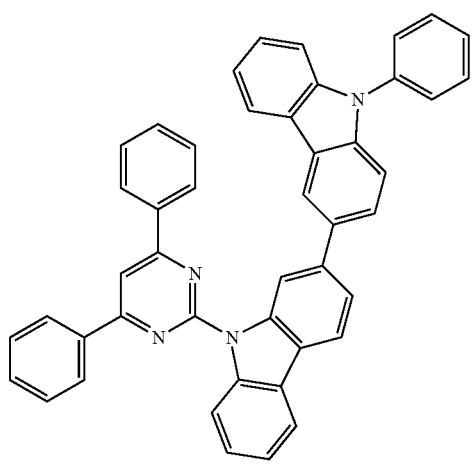

[wherein TPS represents a triphenylsilyl group]

The dopant comprised in the organic electroluminescent device according to the present disclosure may be preferably at least one phosphorescent dopant. The phosphorescent dopant materials applied to the organic electroluminescent device according to the present disclosure are not particularly limited, but may be preferably selected from metallated complex compounds of iridium (Ir), osmium (Os), copper (Cu), and platinum (Pt), may be more preferably selected from ortho-metallated complex compounds of iridium (Ir), osmium (Os), copper (Cu), and platinum (Pt), and may be even more preferably an ortho-metallated iridium complex compound.

The dopant comprised in the organic electroluminescent device of the present disclosure may be selected from the group consisting of the compounds represented by formulas 101 to 104 below, but is not limited thereto.

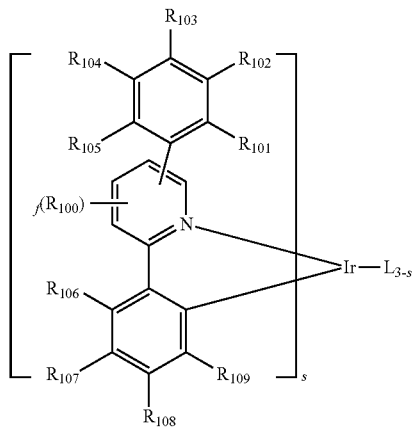

(101)

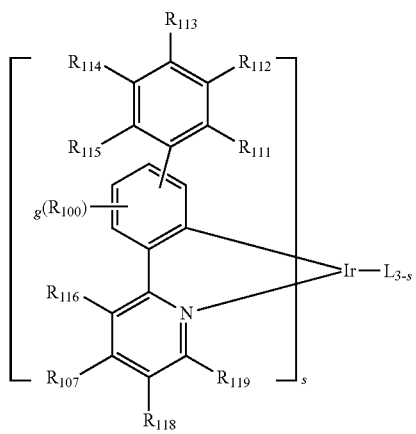

(102)

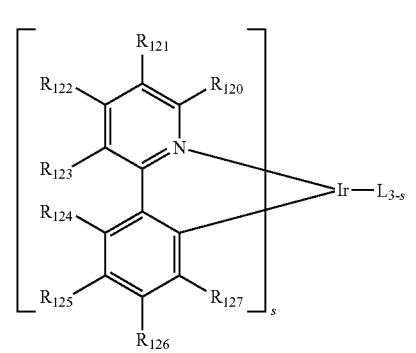

(103)

-continued (104)

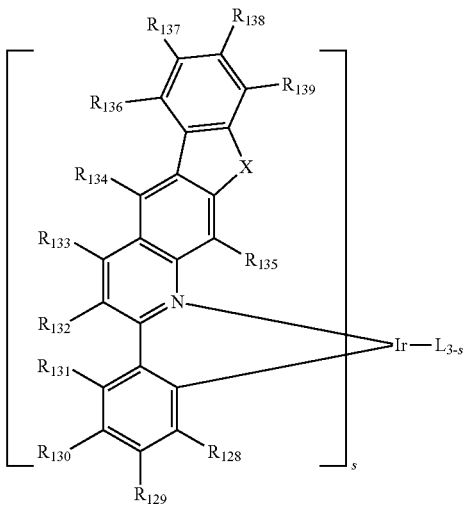

wherein L is selected from the following structures:

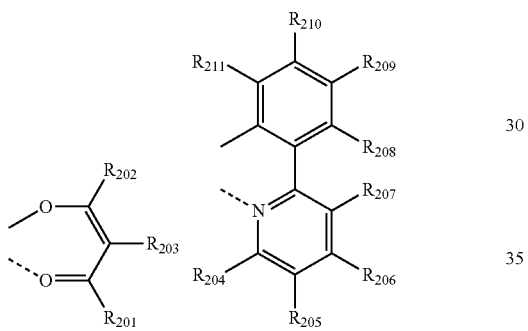

$R_{100}$, $R_{134}$, and $R_{135}$, each independently, represent hydrogen, deuterium, a substituted or unsubstituted (C1-C30)alkyl, or a substituted or unsubstituted (C3-C30)cycloalkyl;

$R_{101}$ to $R_{109}$ and $R_{111}$ to $R_{123}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a cyano, or a substituted or unsubstituted (C1-C30)alkoxy; an adjacent substituent of $R_{106}$ to $R_{109}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl; and adjacent substituents of $R_{120}$ to $R_{123}$ may be linked to each other to form a substituted or unsubstituted fused ring, e.g., a quinoline unsubstituted or substituted with at least one of an alkyl, an aryl, an aralkyl, and an alkylaryl;

$R_{124}$ to $R_{133}$ and $R_{136}$ to $R_{139}$, each independently, represent hydrogen, deuterium, a halogen, a substituted or unsubstituted (C1-C30)alkyl, or a substituted or unsubstituted (C6-C30)aryl; and adjacent substituents of $R_{124}$ to $R_{127}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

X represents $CR_{21}R_{22}$, O, or S;

$R_{21}$ and $R_{22}$, each independently, represent a substituted or unsubstituted (C1-C10)alkyl, or a substituted or unsubstituted (C6-C30)aryl;

$R_{201}$ to $R_{211}$, each independently, represent hydrogen, deuterium, a halogen, a (C1-C30)alkyl unsubstituted or substituted with deuterium or a halogen, a substituted or unsubstituted (C3-C30)cycloalkyl, or a (C6-C30)aryl unsubstituted or substituted with an alkyl or deuterium; and adjacent substituents of $R_{208}$ to $R_{211}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

f and g, each independently, represent an integer of 1 to 3; where f or g is an integer of 2 or more, each $R_{100}$ may be the same or different; and s represents an integer of 1 to 3.

The specific examples of the dopant compound are as follows:

D-1

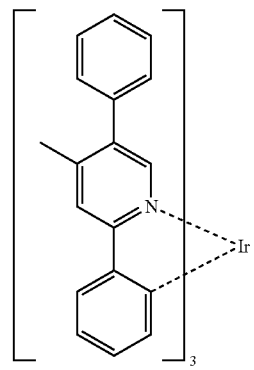

D-2

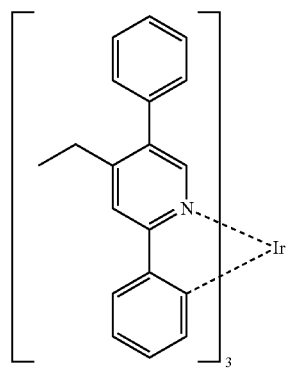

D-3

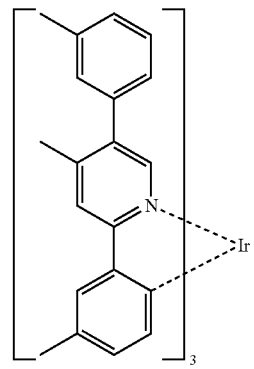

D-4
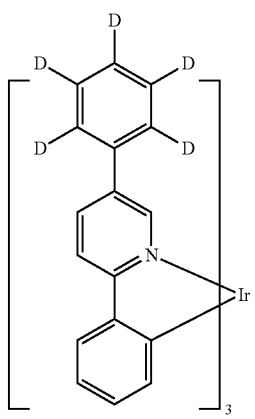
D-5
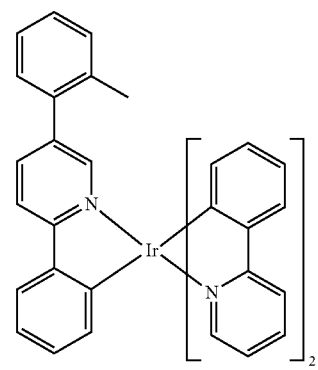
D-6
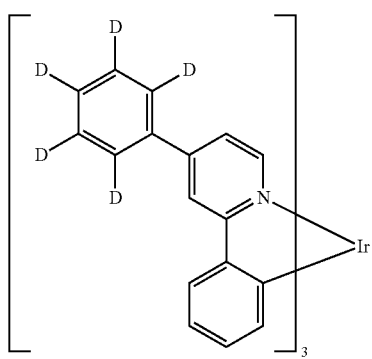
D-7
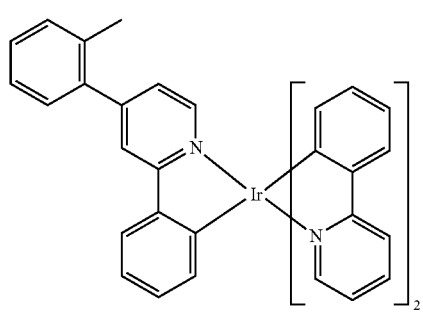
D-8
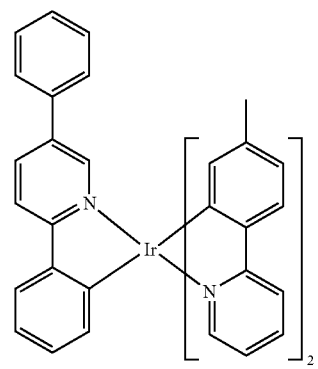
D-9
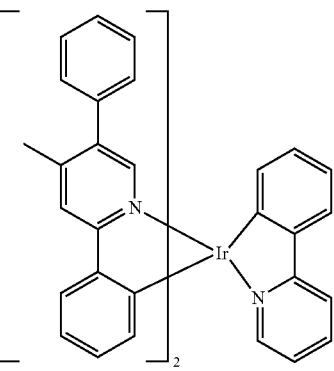
D-10
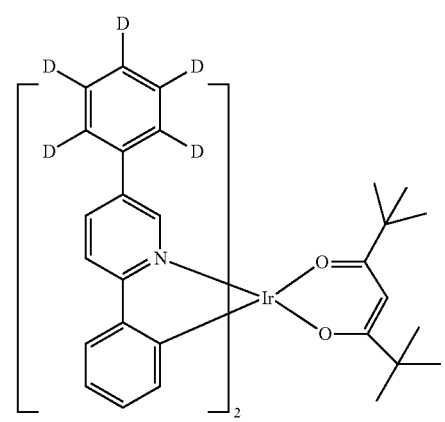
D-11
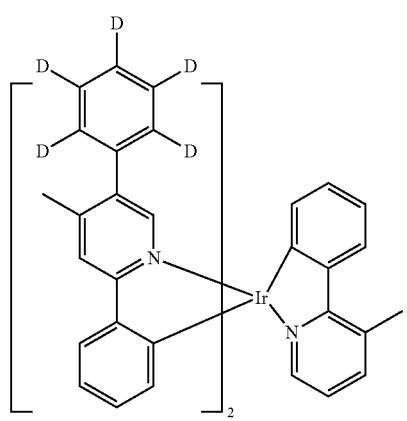

-continued
D-12
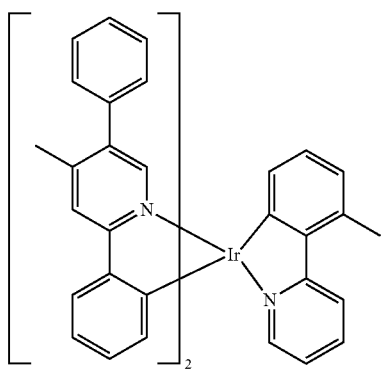
D-13
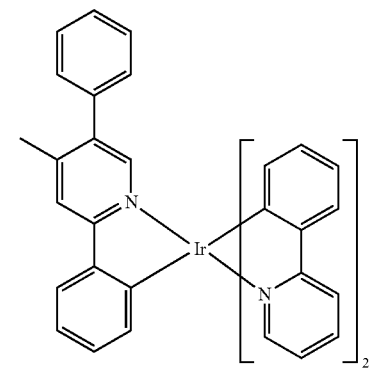
D-14
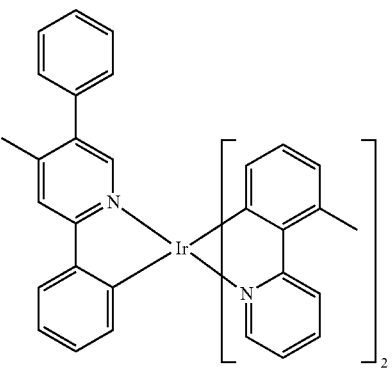
D-15
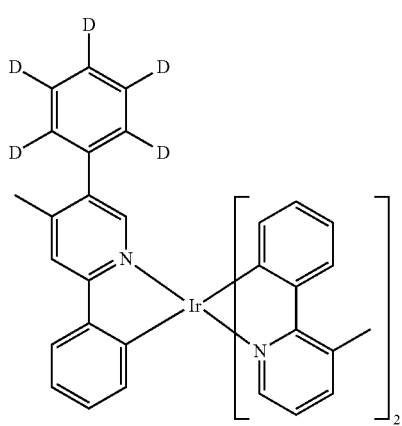
-continued
D-16
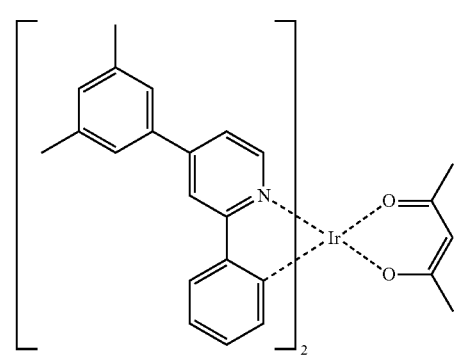
D-17
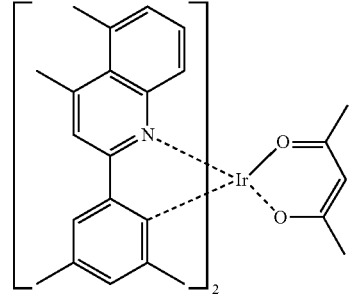
D-18
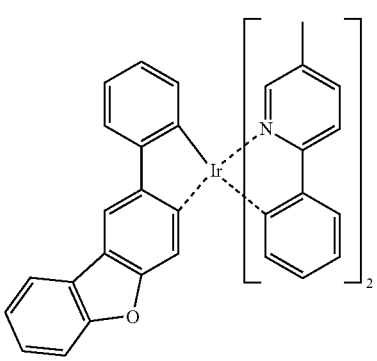
D-19
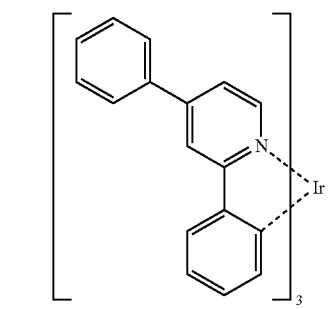
D-20
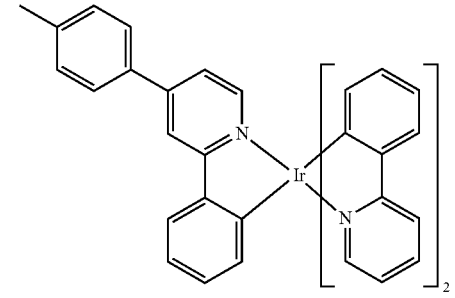

-continued
D-21
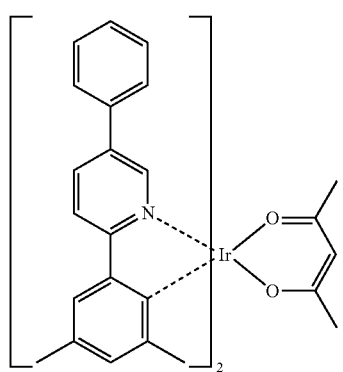
D-22
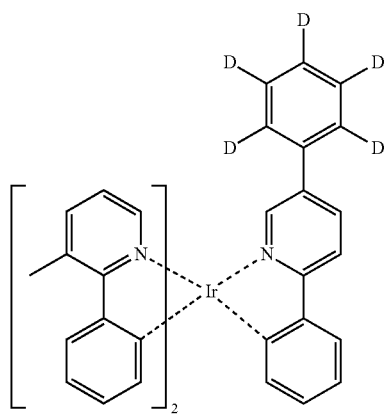
D-23
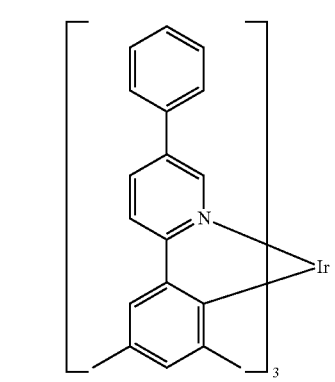
D-24
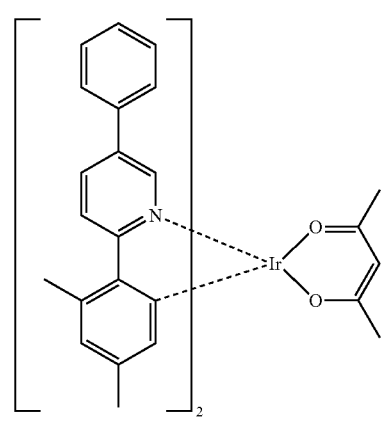
D-25
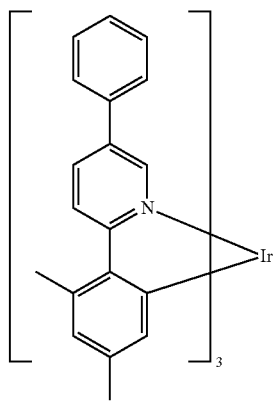
D-26
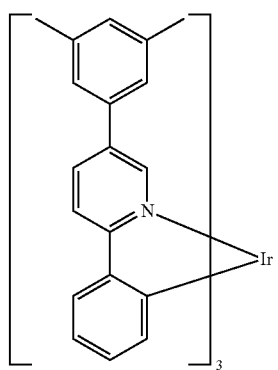
D-27
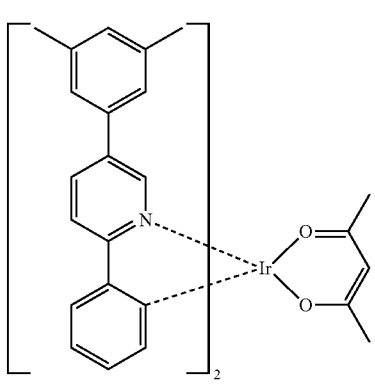
D-28
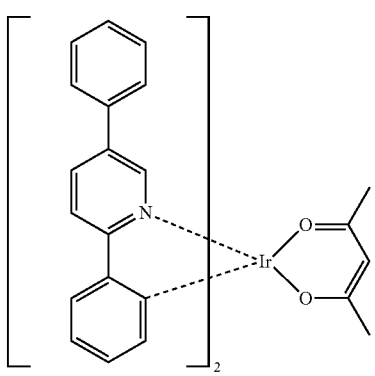

D-29 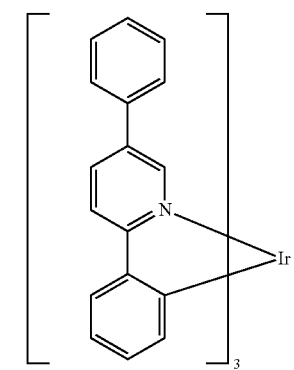
D-30 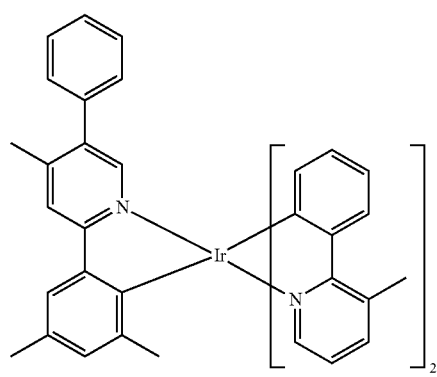
D-31 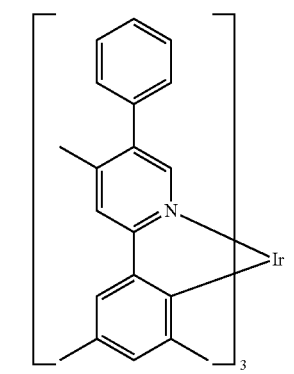
D-32 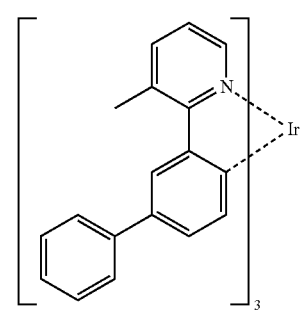
D-33 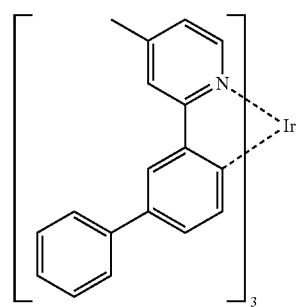
D-34 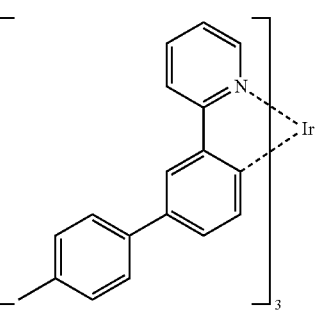
D-35 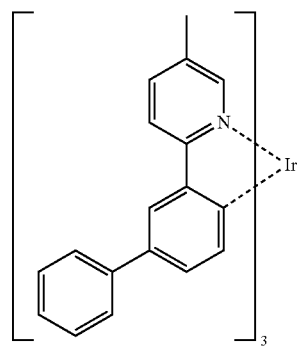
D-36 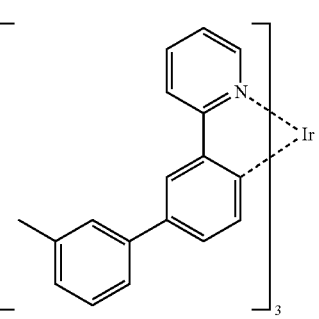
D-37 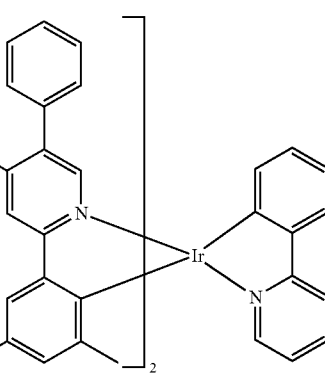

D-38 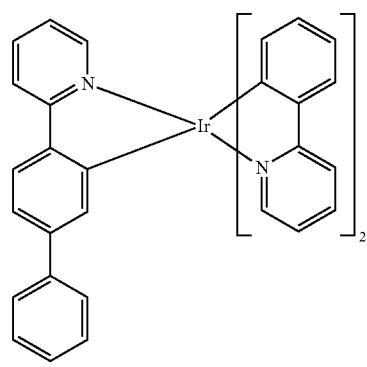
D-39 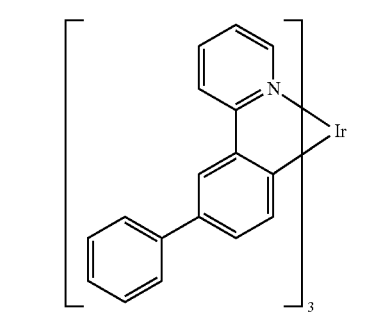
D-40 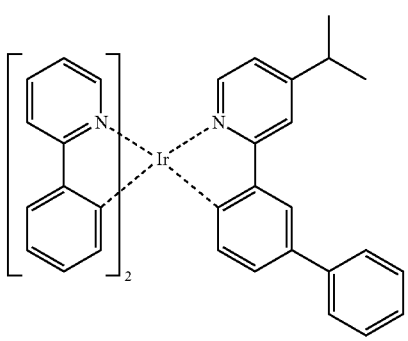
D-41 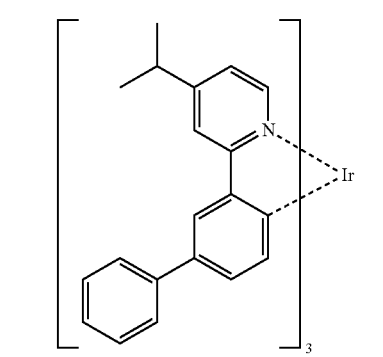
D-42 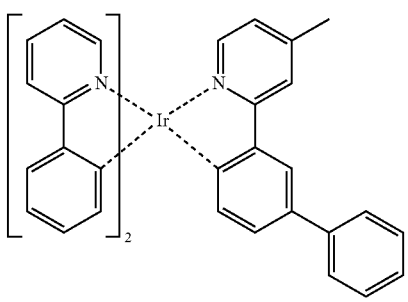
D-43 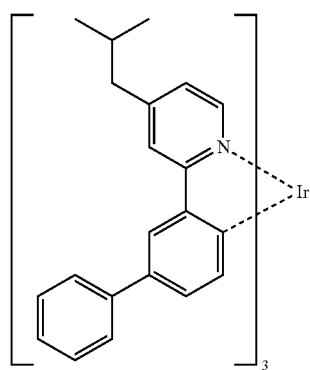
D-44 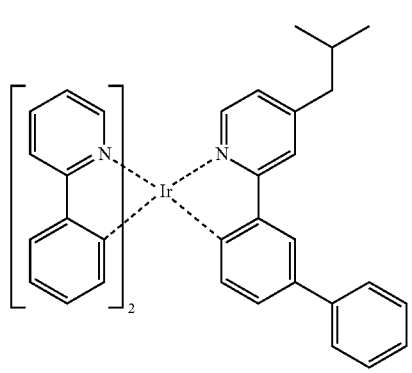
D-45 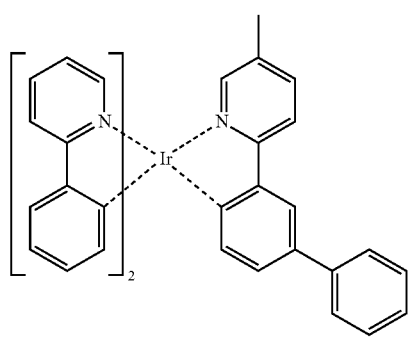
D-46 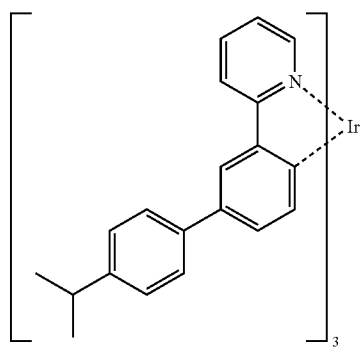

-continued
D-47
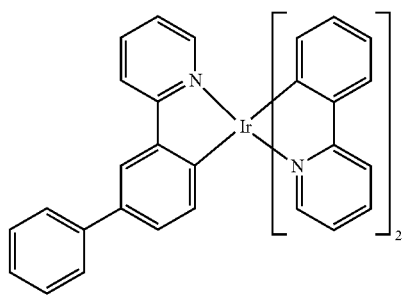
D-48
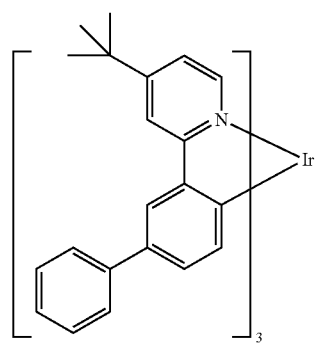
D-49
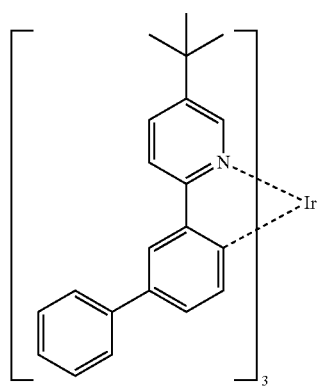
D-50
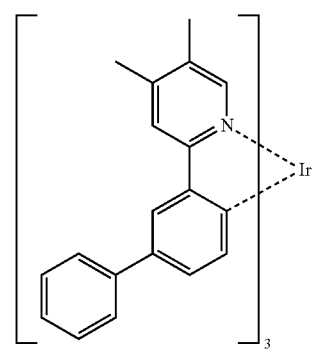
-continued
D-51
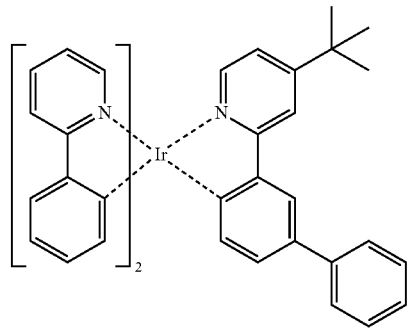
D-52
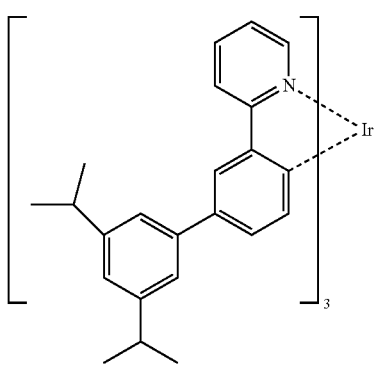
D-53
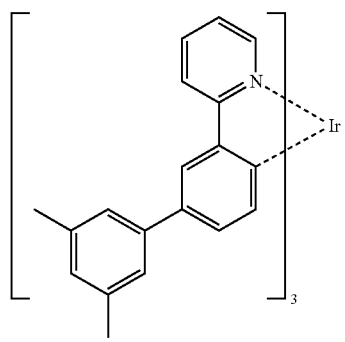
D-54
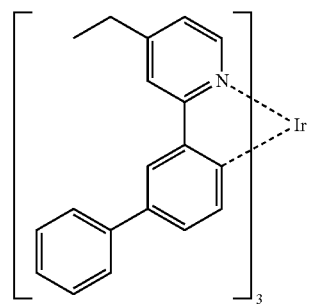

D-55 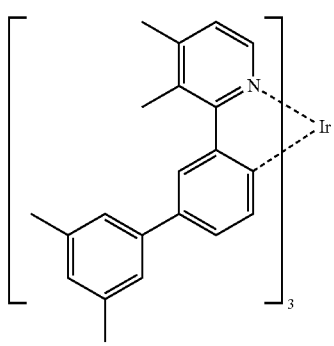
D-56 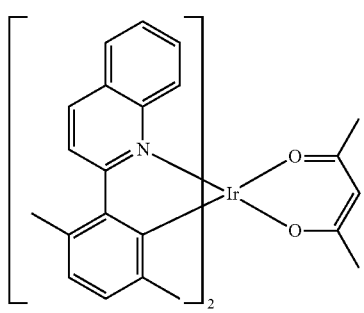
D-57 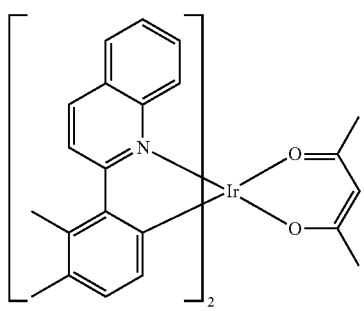
D-58 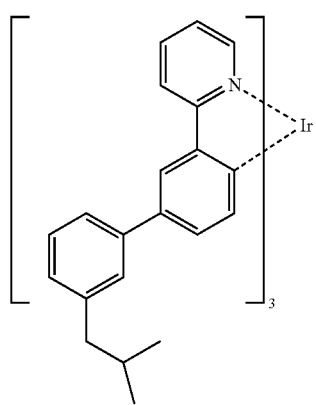
D-59 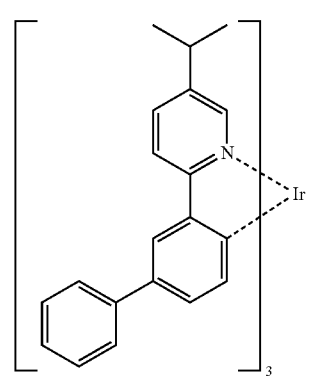
D-60 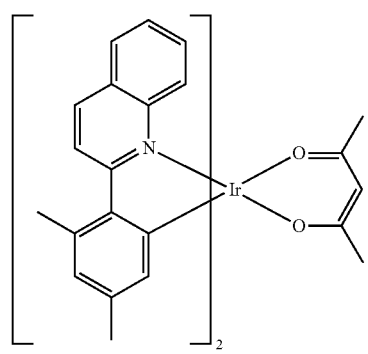
D-61 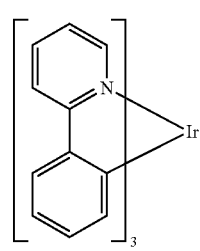
D-62 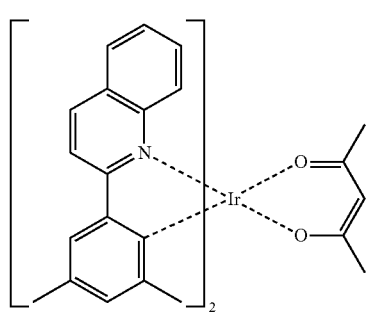

-continued
D-63
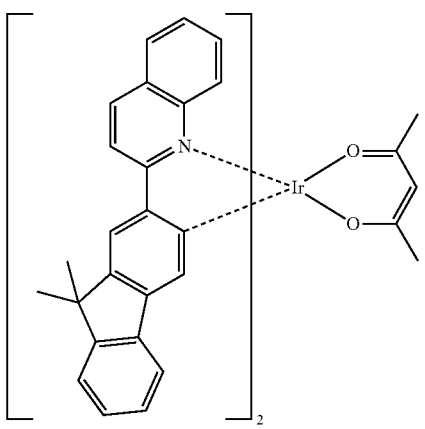
D-64
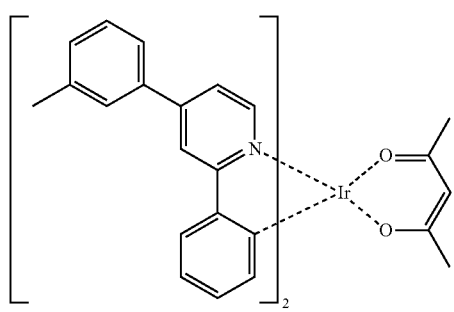
D-65
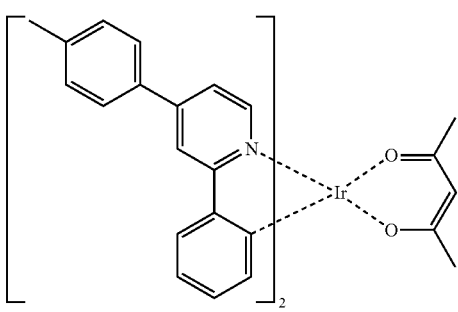
D-66
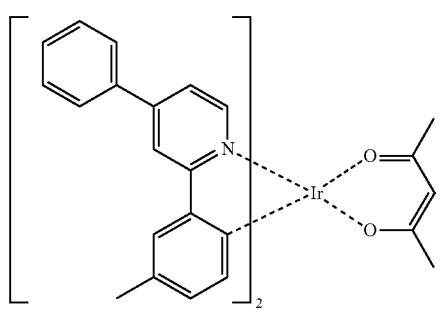
-continued
D-67
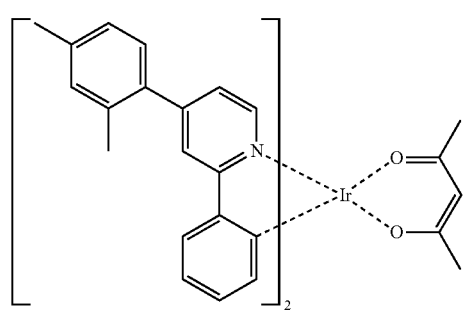
D-68
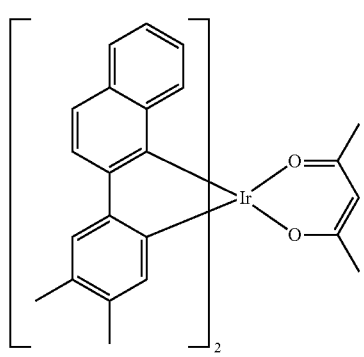
D-69
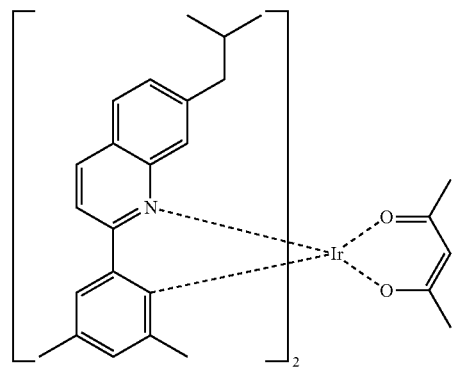
D-70
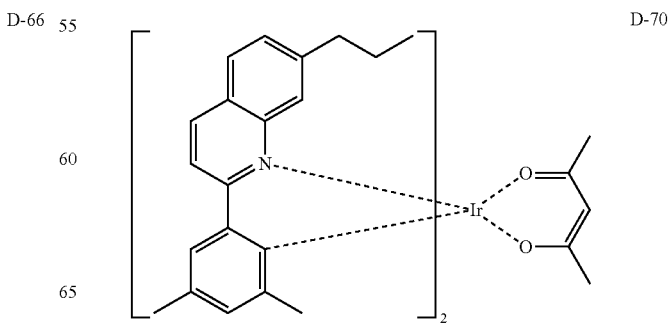

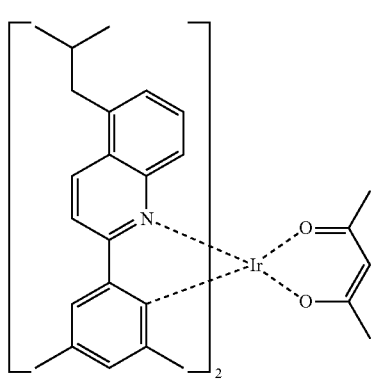
D-71
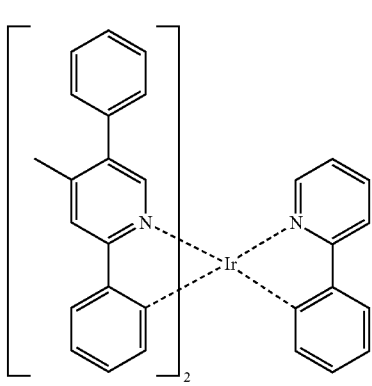
D-75
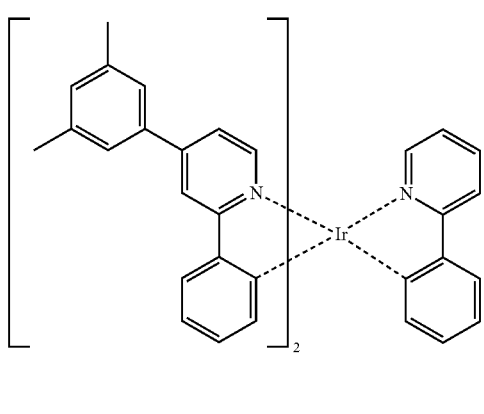
D-72
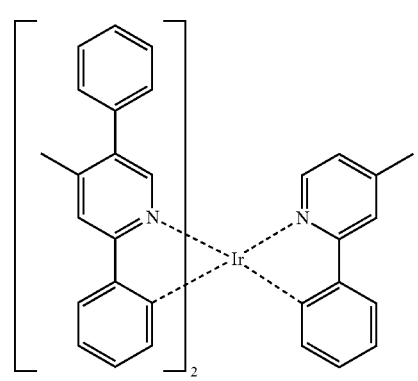
D-76
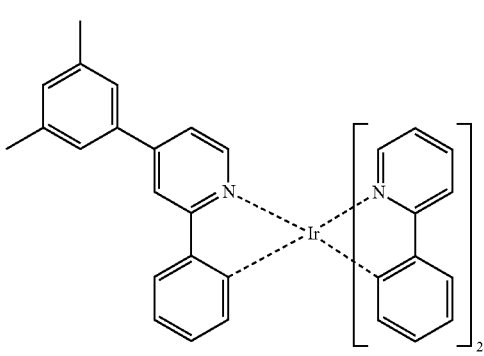
D-73
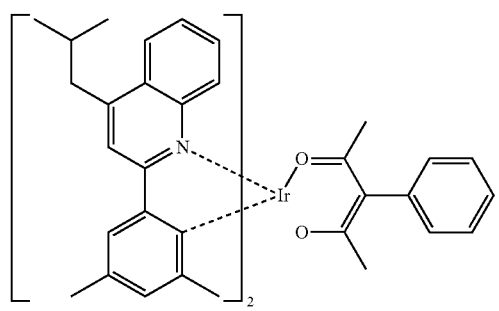
D-77
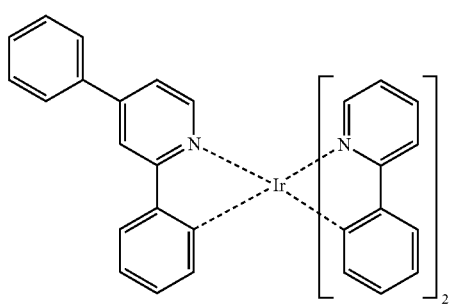
D-74
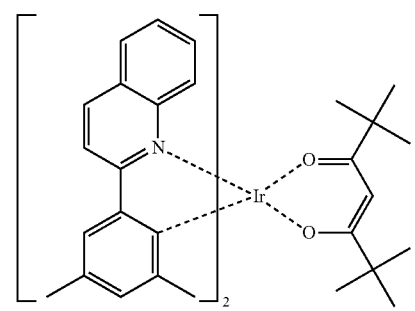
D-78

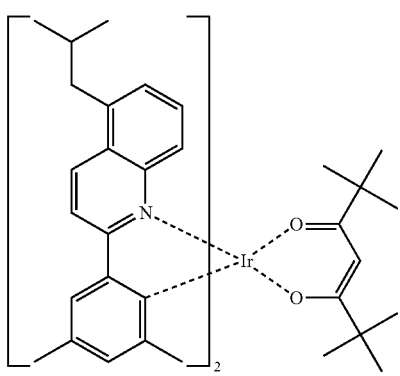
D-79
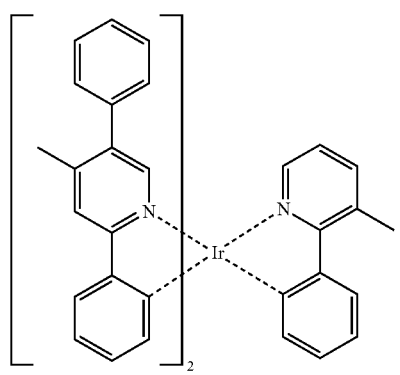
D-80
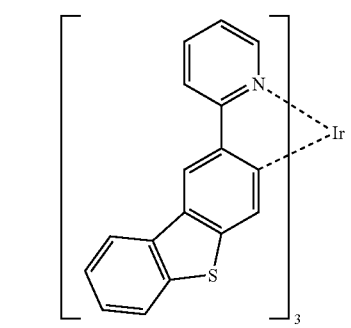
D-81
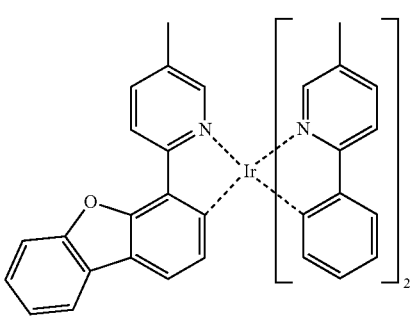
D-82
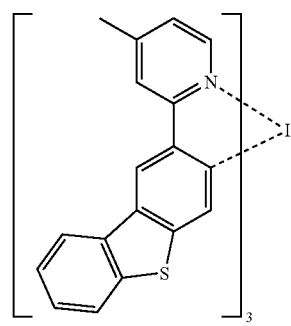
D-83
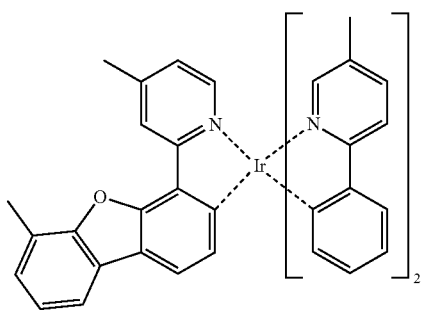
D-84
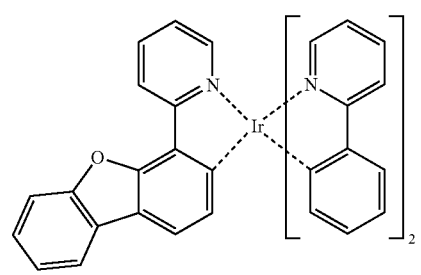
D-85
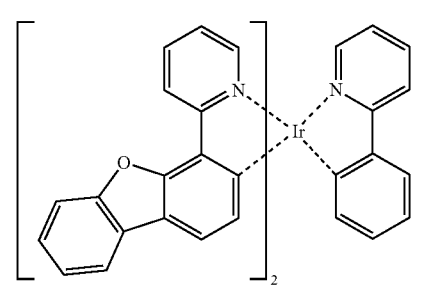
D-86
D-87

D-88
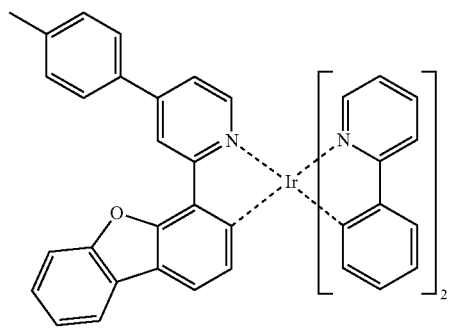
D-89
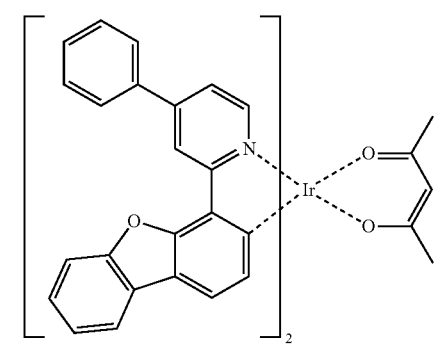
D-90
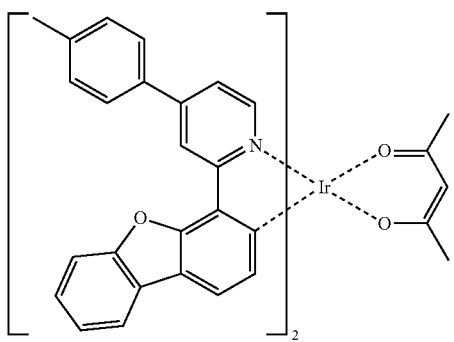
D-91
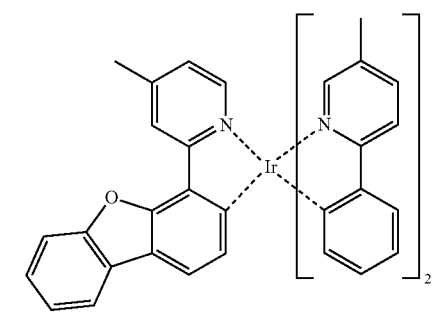
D-92
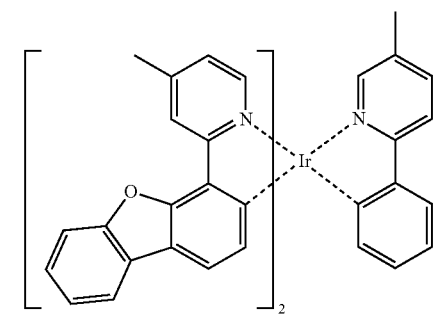
D-93
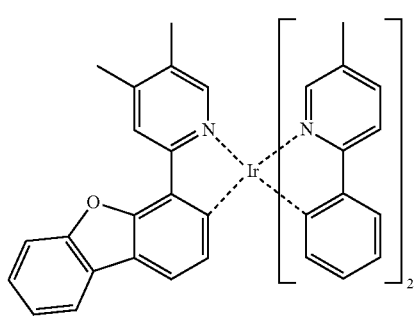
D-94
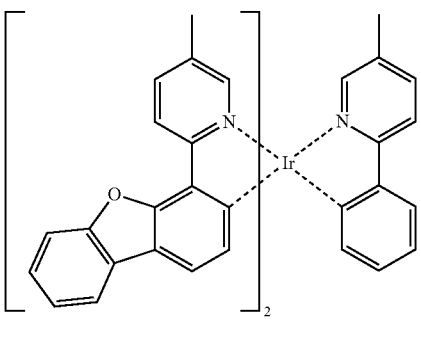
D-95
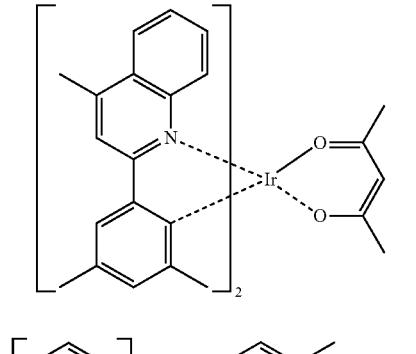
D-96
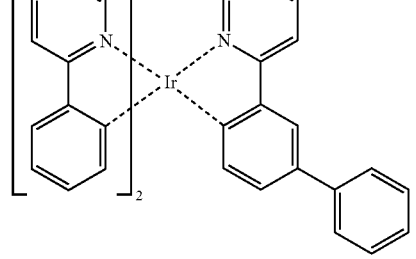
D-97
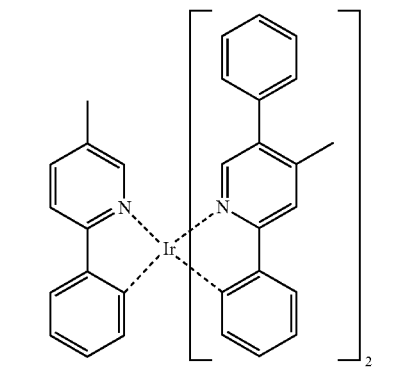

-continued
D-98
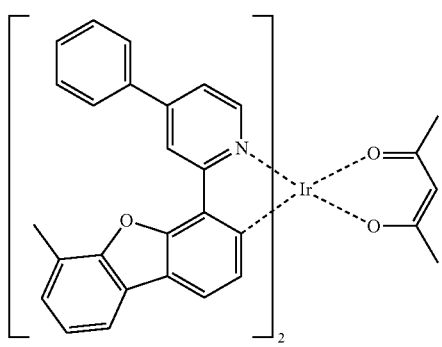
D-99
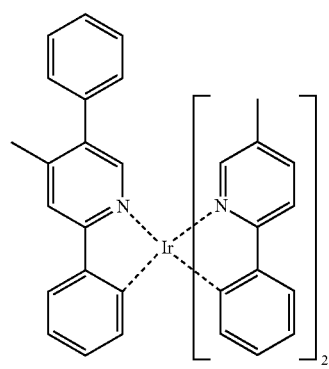
D-100
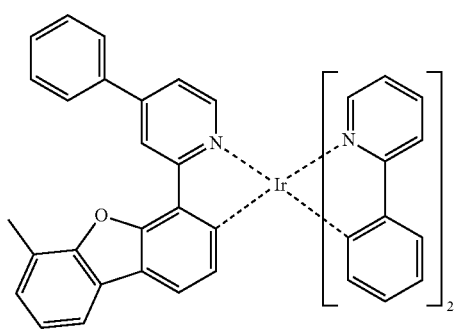
D-101
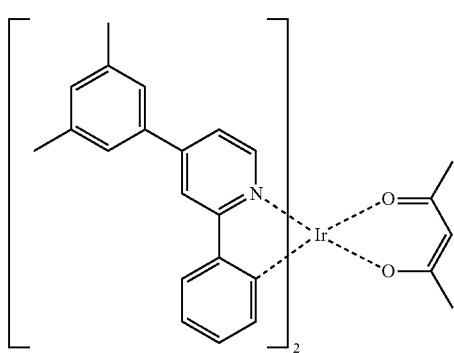
-continued
D-102
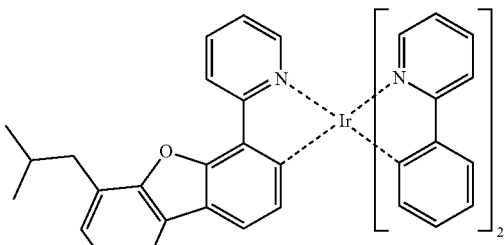
D-103
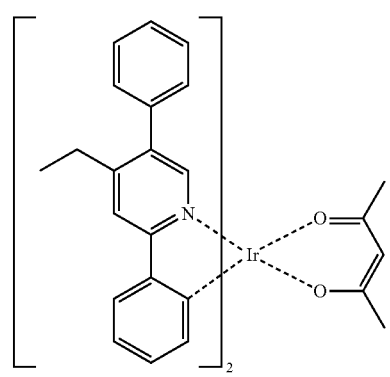
D-104
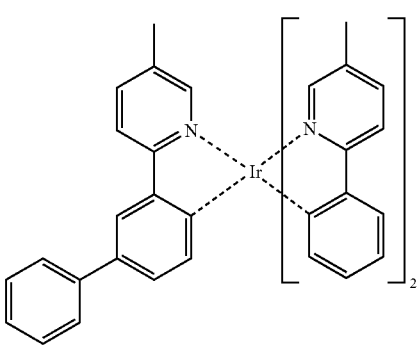
D-105
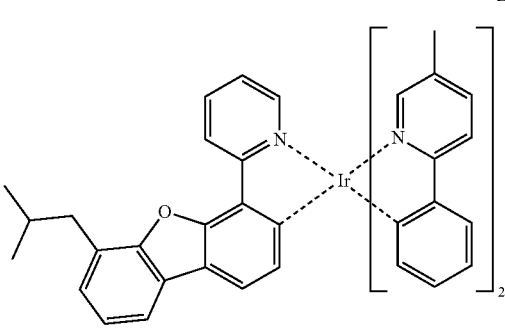

-continued
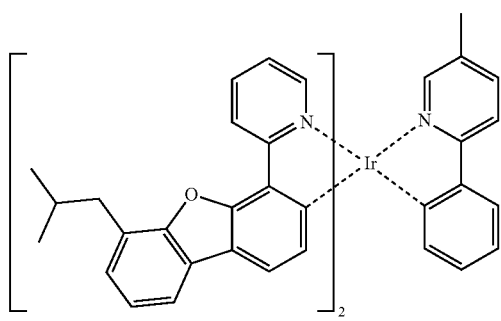
D-106
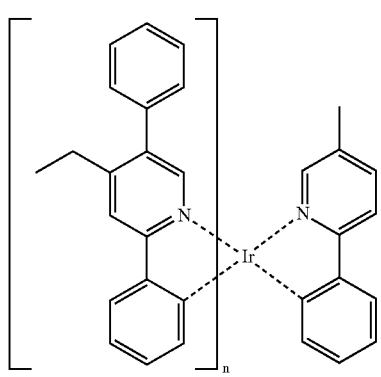
D-107
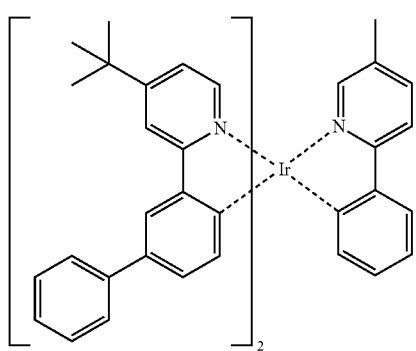
D-108
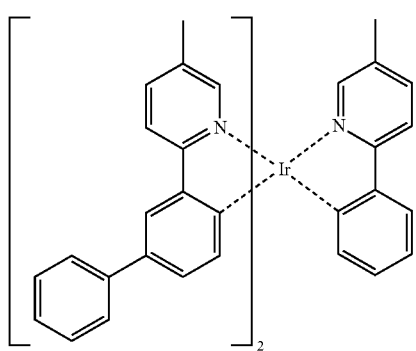
D-109
-continued
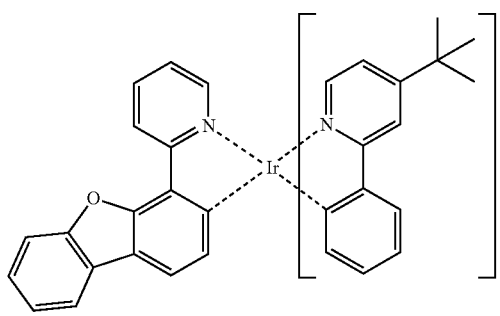
D-110
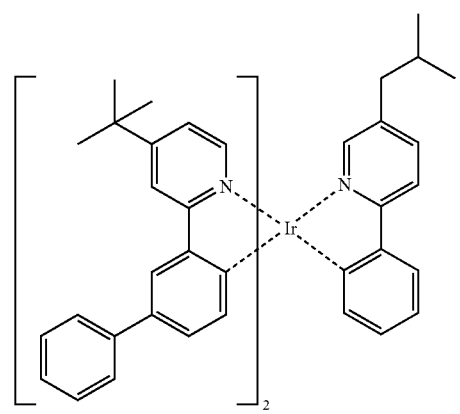
D-111
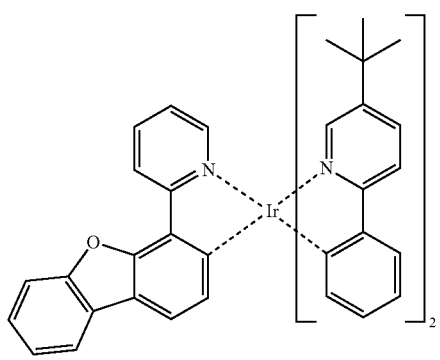
D-112
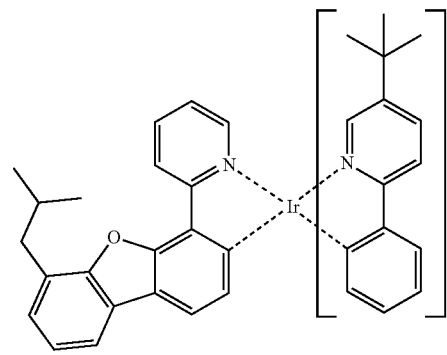
D-113

D-114
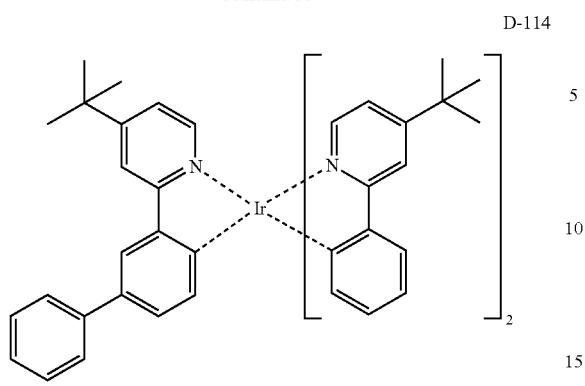
D-115
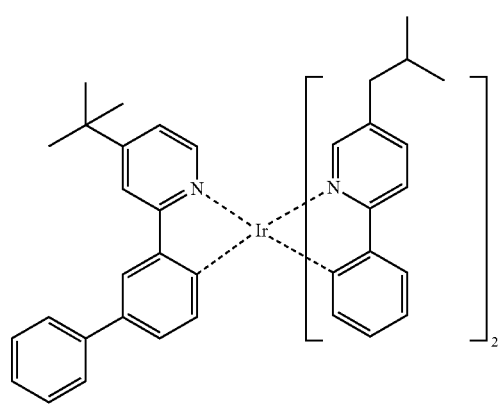
D-116
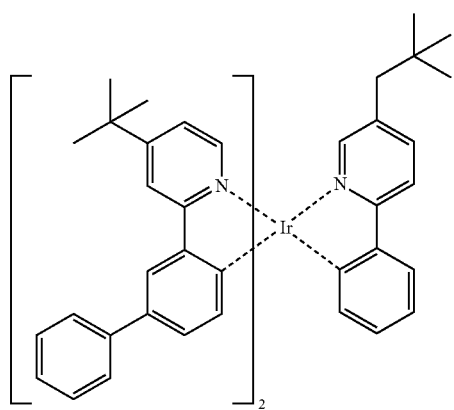
D-117
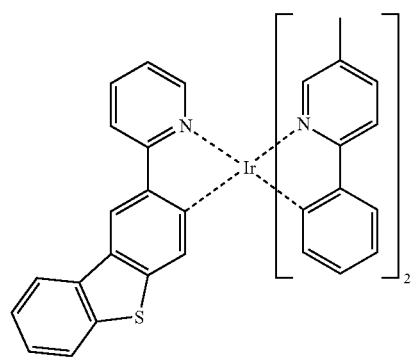
D-118
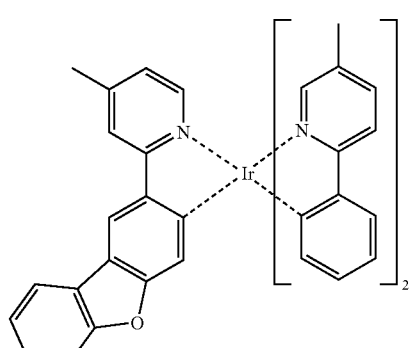
D-119
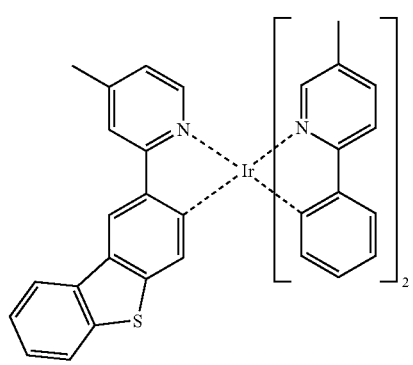
D-120
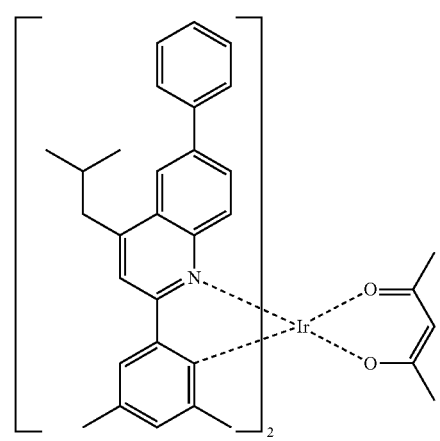
D-121
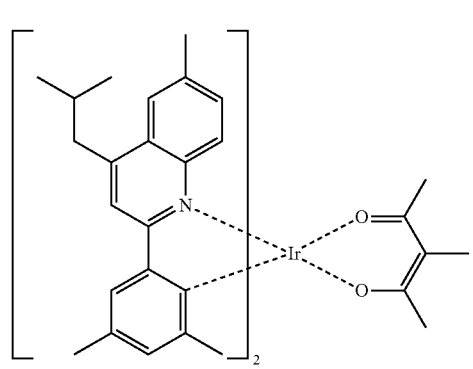

D-122
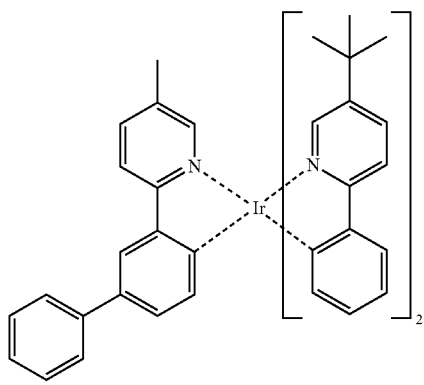
D-123
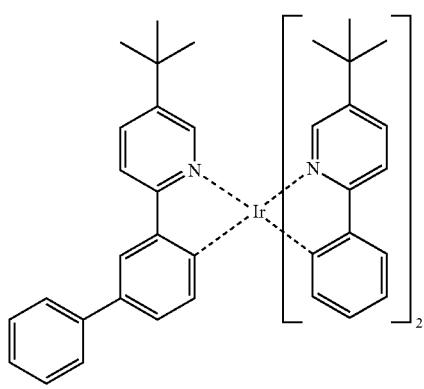
D-124
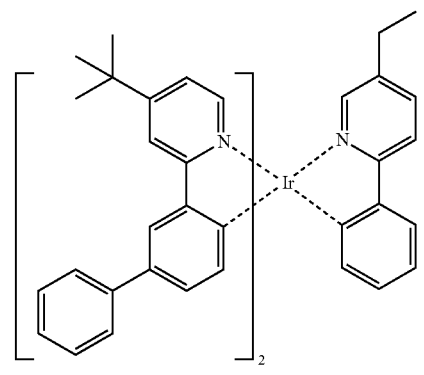
D-125
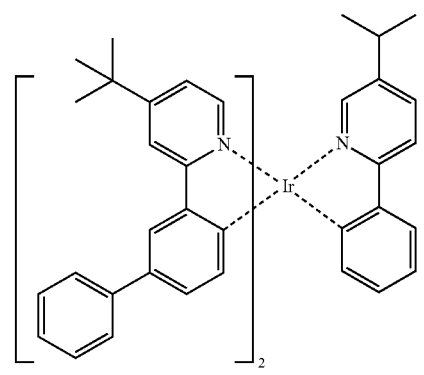
D-126
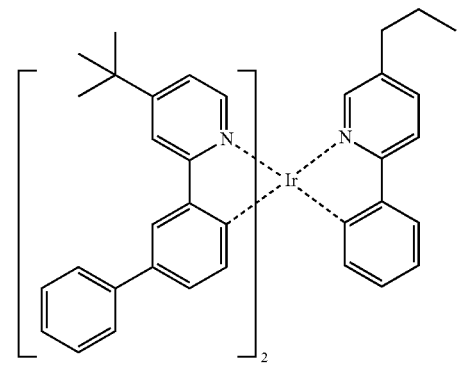
D-127
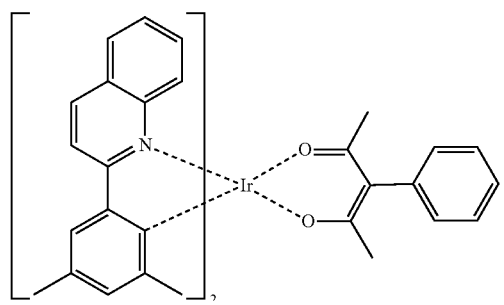
D-128
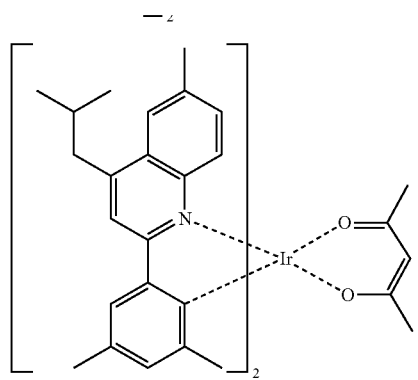
D-129
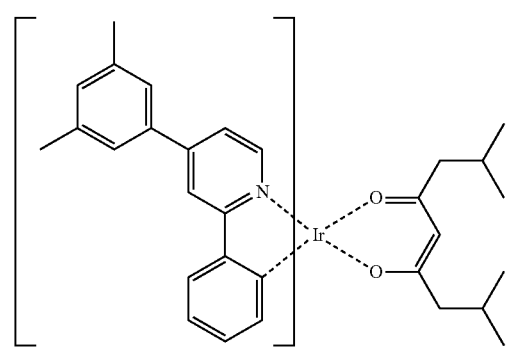

D-130
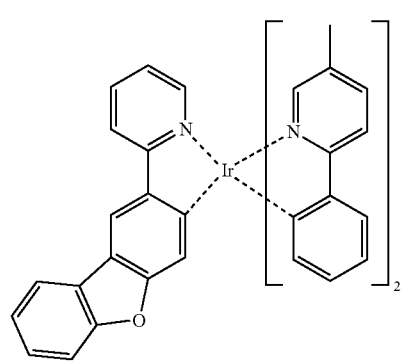
D-131
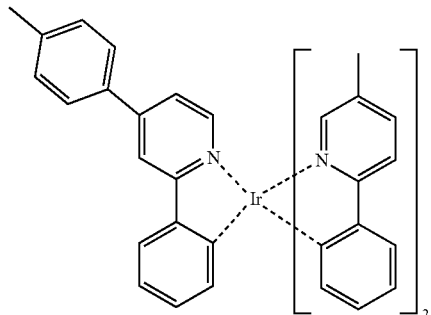
D-132
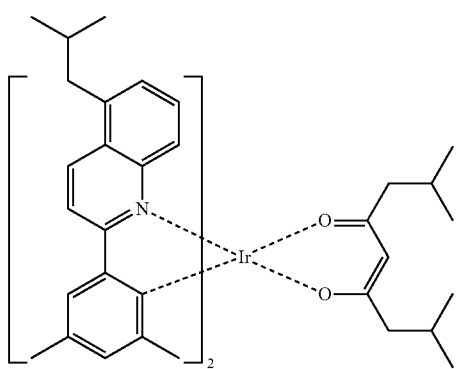
D-133
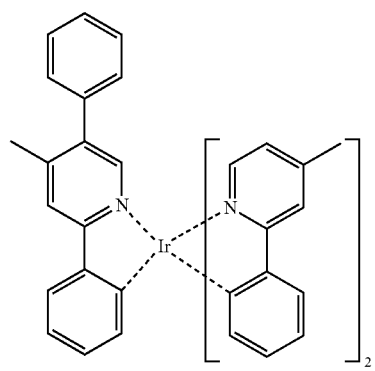
D-134
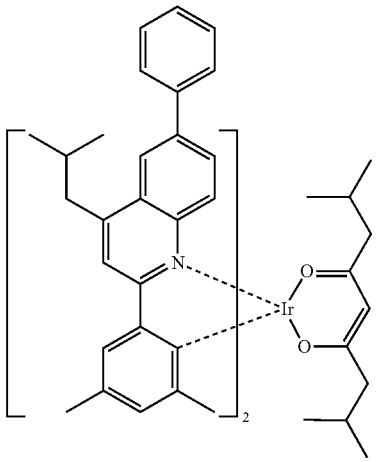
D-135
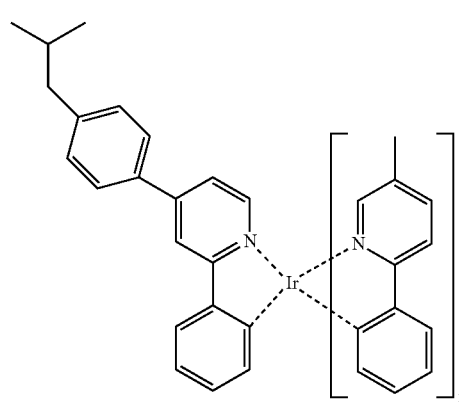
D-136
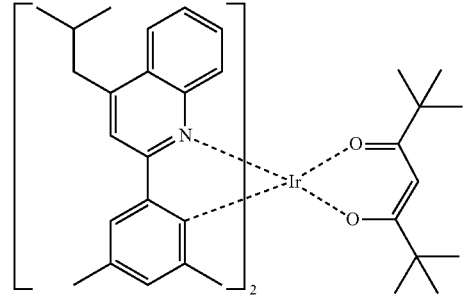
D-137
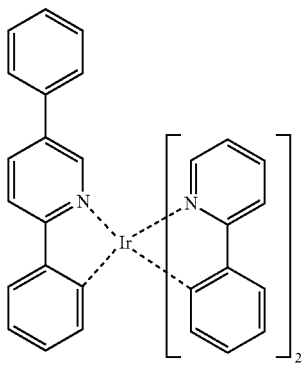

D-138
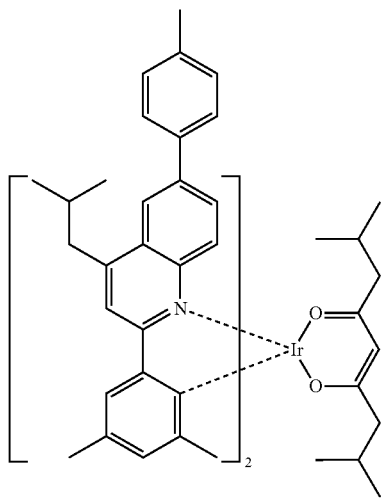
D-139
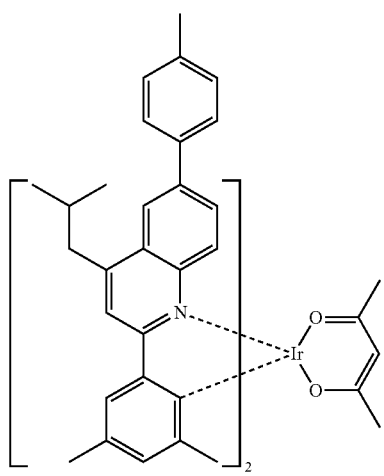
D-140
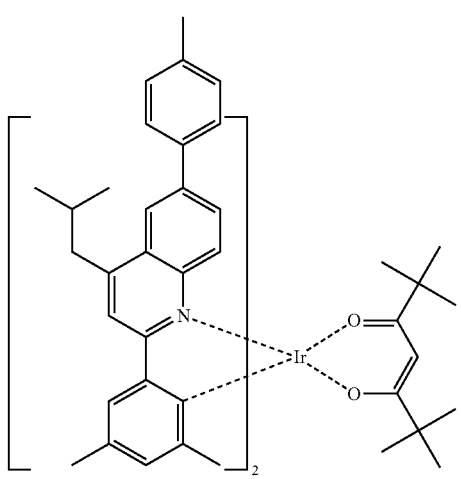
D-141
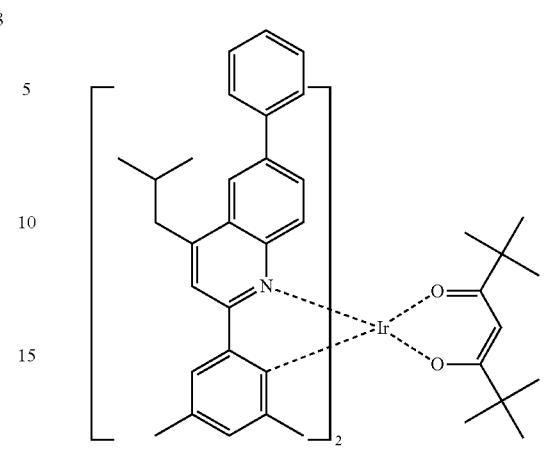
D-142
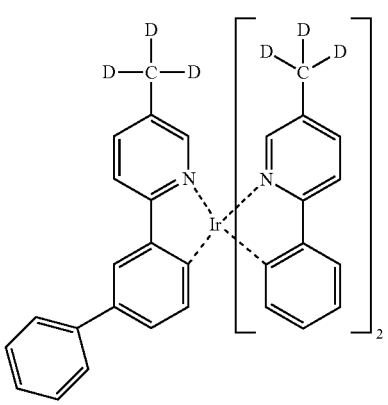
D-143
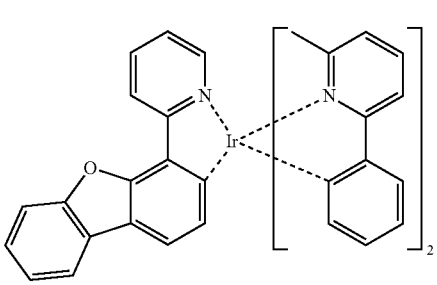
D-144
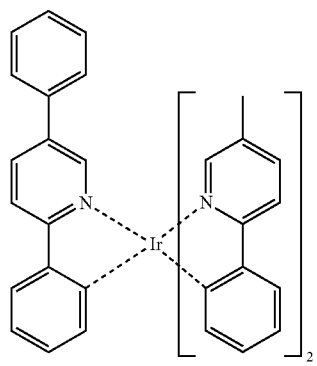

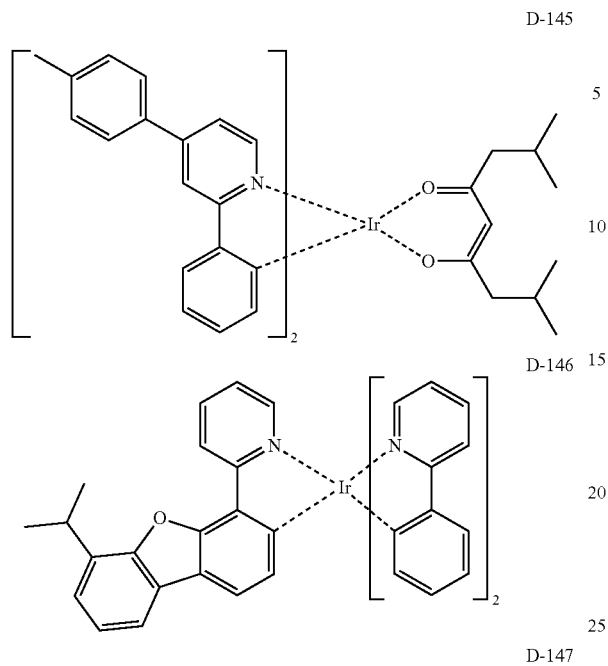
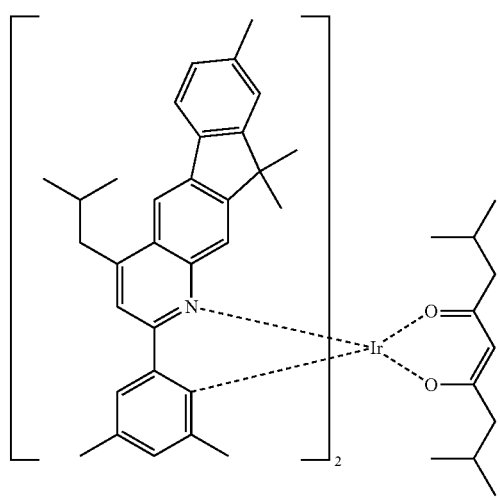

D-153

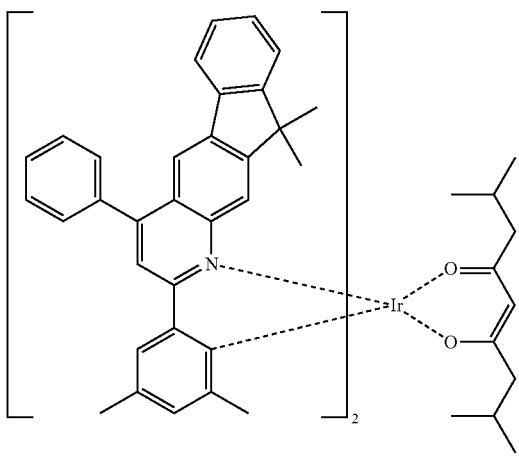

D-156

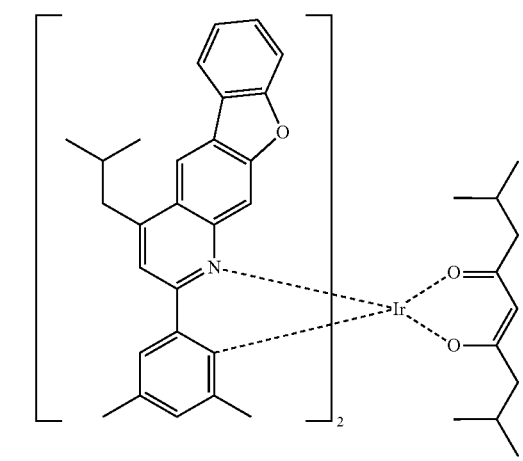

D-154

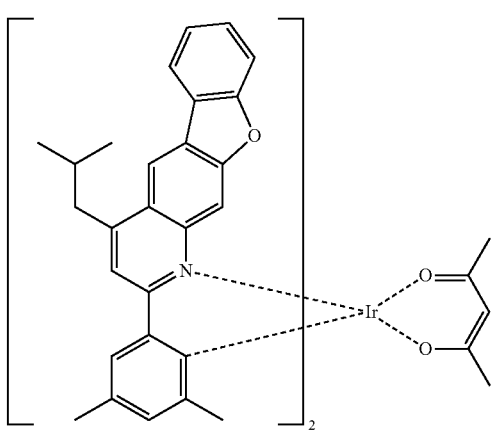

D-157

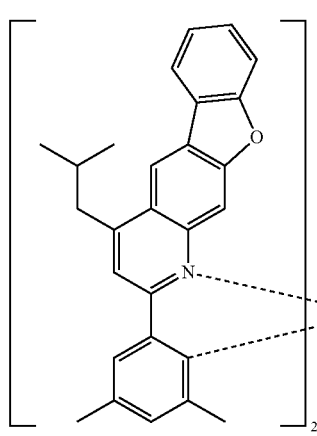

D-155

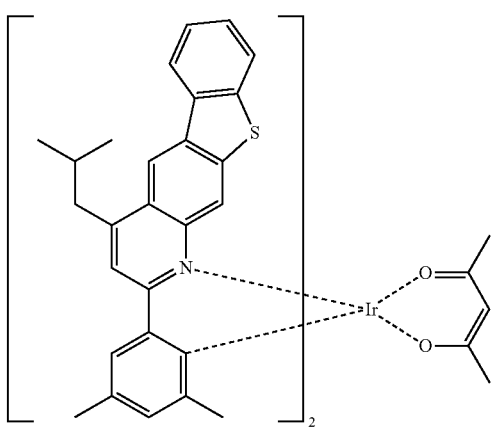

In another embodiment of the present disclosure, a composition for preparing an organic electroluminescent device is provided. The composition comprises the compound according to the present disclosure as a host material, a hole transport layer material, a hole auxiliary layer material, a light-emitting auxiliary layer material, an electron buffer layer material, or an electron transport layer material.

In addition, the organic electroluminescent device according to the present disclosure comprises a first electrode; a second electrode; and at least one organic layer between the first and second electrodes. The organic layer comprises a light-emitting layer, and the light-emitting layer may comprise the composition for preparing the organic electroluminescent device according to the present disclosure.

The organic electroluminescent device according to the present disclosure may further comprise, in addition to the organic electroluminescent compound of formula 1, at least one compound selected from the group consisting of arylamine-based compounds and styrylarylamine-based compounds.

In the organic electroluminescent device according to the present disclosure, the organic layer may further comprise, in addition to the organic electroluminescent compound of formula 1, at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal. The organic layer may further comprise a light-emitting layer and a charge generating layer.

In addition, the organic electroluminescent device according to the present disclosure may emit white light by further comprising at least one light-emitting layer which comprises a blue electroluminescent compound, a red electroluminescent compound or a green electroluminescent compound known in the field, besides the compound according to the present disclosure. Also, if necessary, a yellow or orange light-emitting layer can be further comprised in the device.

In the organic electroluminescent device according to the present disclosure, at least one layer (hereinafter, "a surface layer") is preferably placed on an inner surface(s) of one or both electrode(s); selected from a chalcogenide layer, a metal halide layer, and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_X$ ($1 \leq X \leq 2$), $AlO_X$ ($1 \leq X \leq 1.5$), SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each of the multi-layers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic EL device having two or more light-emitting layers which emits white light.

In order to form each layer constituting the organic electroluminescent device of the present disclosure, dry film-forming methods such as vacuum deposition, sputtering, plasma, ion plating methods, etc., or wet film-forming methods such as spin coating, dip coating, flow coating methods, etc., can be used. When forming the film of the first and second host compounds of the present disclosure, a co-evaporation or a mixed evaporation method is used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a film.

By using the organic electroluminescent device of the present disclosure, a display device, for example, for smartphones, tablets, notebooks, PCs, TVs, or vehicles, or a lighting device, for example, an indoor or outdoor lighting device, can be produced.

Hereinafter, the preparation method of the organic electroluminescent compounds of the present disclosure, the physical properties of the compounds, and the luminous properties of the organic electroluminescent device comprising the compounds will be explained in detail with reference to the representative compounds of the present disclosure.

EXAMPLE 1

Preparation of Compound C-50

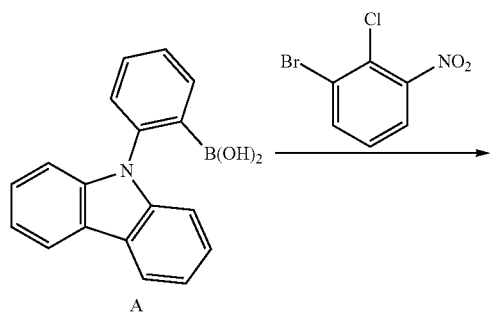

A

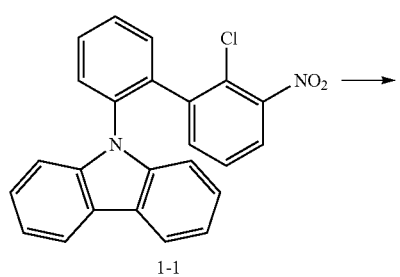

1-1

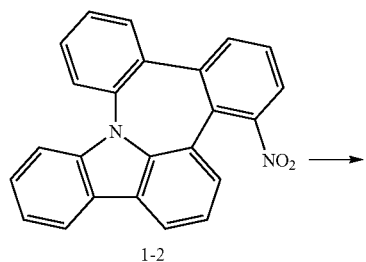

1-2

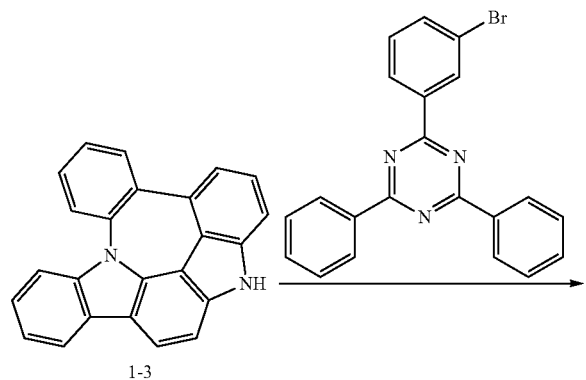

1-3

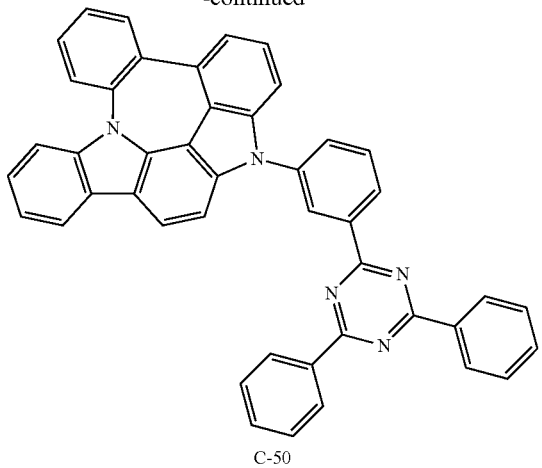

C-50

Preparation of Compound 1-1

36 g of compound A (125.38 mmol), 27 g of 3-bromo-2-chloro-nitrobenzene (113.98 mmol), 4 g of tetrakis(triphenylphosphine)palladium (3.42 mmol), 30 g of sodium carbonate (284.95 mmol), 570 mL of toluene, 140 mL of ethanol, and 140 mL of distilled water were introduced into a reaction vessel, and the mixture was stirred at 120° C. for 3 hours. After completion of the reaction, the mixture was cooled to room temperature and extracted with ethyl acetate. The extracted organic layer was then dried with magnesium sulfate, and the solvent was removed with a rotary evaporator. Thereafter, the resulting product was purified by column chromatography to obtain 30 g of compound 1-1 (yield: 66%).

Preparation of Compound 1-2

27 g of compound 1-1 (68.20 mmol), 1.5 g of palladium (II) acetate (6.82 mmol), 5.0 g of tricyclohexylphosphoniumtetrafluoroborate (13.64 mmol), 66 g of cesium carbonate (204.60 mmol), and 340 mL of o-xylene were introduced into a reaction vessel, and the mixture was stirred under reflux for 2 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 26 g of compound 1-2.

Preparation of Compound 1-3

Compound 1-2 (68.20 mmol) and 176 mL of triethylphosphite (0.4 M) were introduced into a reaction vessel, and the mixture was stirred at 150° C. for 4 hours. After completion of the reaction, triethylphosphite was removed by distillation under reduced pressure. The mixture was then washed with distilled water, extracted with ethyl acetate, and the extracted organic layer was dried with magnesium sulfate. The solvent was removed with a rotary evaporator, and the resulting product was purified by column chromatography to obtain 16.4 g of compound 1-3 (yield: 70%).

Preparation of Compound C-50

7 g of compound 1-3 (21.19 mmol), 9.9 g of 2-(3-bromophenyl)-4,6-diphenyl-1,3,5-triazine (25.43 mmol), 0.5 g of palladium (II) acetate (2.12 mmol), 1.8 g of 2-dicyclohexylphosphino-2',6'-dimethoxybiphenyl (s-phos) (4.24 mmol), 3.1 g of sodium tert-butoxide (31.79 mmol), and 110 mL of o-xylene were introduced into a reaction vessel, and the mixture was stirred under reflux for 3 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 5 g of compound C-50 (yield: 37%).

|  | MW | UV | PL | M.P. |
|---|---|---|---|---|
| C-50 | 637.73 | 324 nm | 499 nm | 291° C. |

EXAMPLE 2

Preparation of Compound C-51

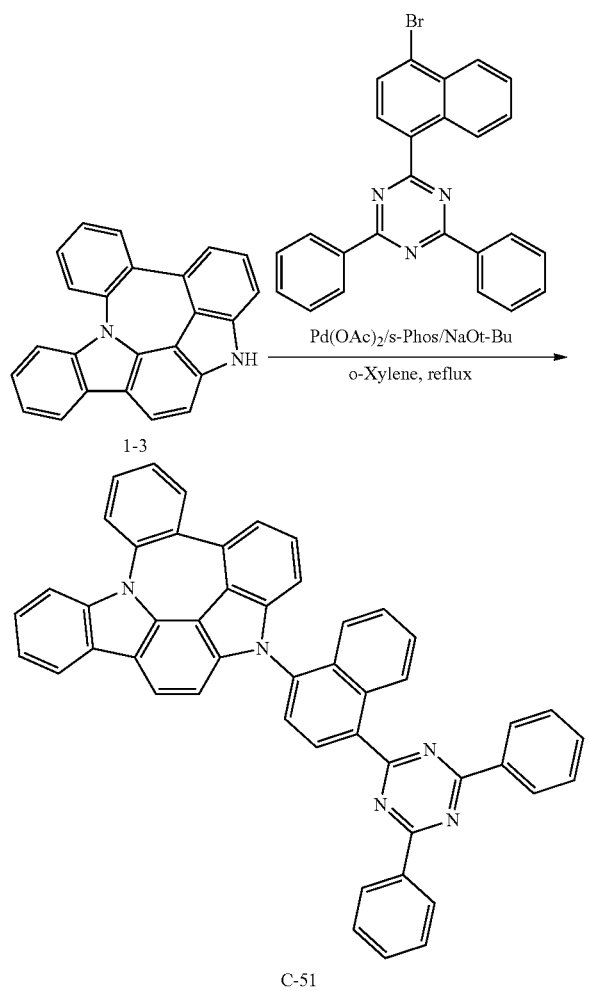

C-51

5 g of compound 1-3 (15 mmol), 8.6 g of 2-(4-bromonaphthylen-1-yl)-4,6-diphenyl-1,3,5-triazine (20 mmol), 0.4 g of palladium (II) acetate (2 mmol), 1.2 g of s-phos (3 mmol), 2.2 g of sodium tert-butoxide (23 mmol), and 76 mL of o-xylene were introduced into a reaction vessel, and the mixture was stirred under reflux for 3 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 3.3 g of compound C-51 (yield: 32%).

|  | MW | UV | PL | M.P. |
|---|---|---|---|---|
| C-51 | 687.79 | 424 nm | 497 nm | 303° C. |

EXAMPLE 3

Preparation of Compound C-49

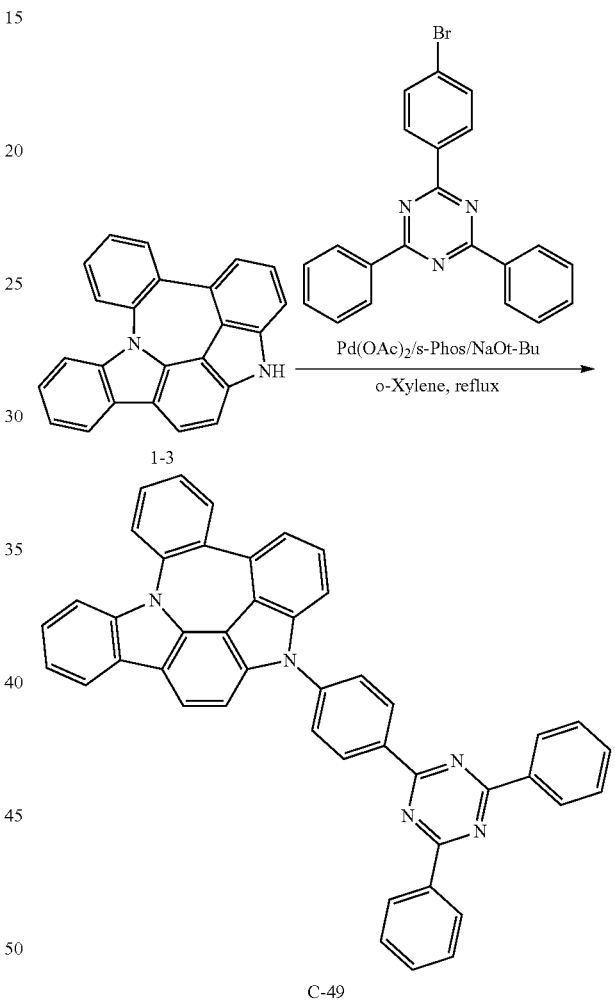

C-49

6 g of compound 1-3 (18 mmol), 8.5 g of 2-(4-bromophenyl)-4,6-diphenyl-1,3,5-triazine (22 mmol), 0.4 g of palladium (II) acetate (2 mmol), 1.5 g of s-phos (4 mmol), 2.6 g of sodium tert-butoxide (27 mmol), and 91 mL of o-xylene were introduced into a reaction vessel, and the mixture was stirred under reflux for 2 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 10 g of compound C-49 (yield: 86%).

| | MW | M.P. |
|---|---|---|
| C-49 | 637.75 | 274° C. |

| | MW | UV | PL | M.P. |
|---|---|---|---|---|
| C-17 | 637.73 | 392 nm | 497 nm | 240° C. |

EXAMPLE 4

Preparation of Compound C-17

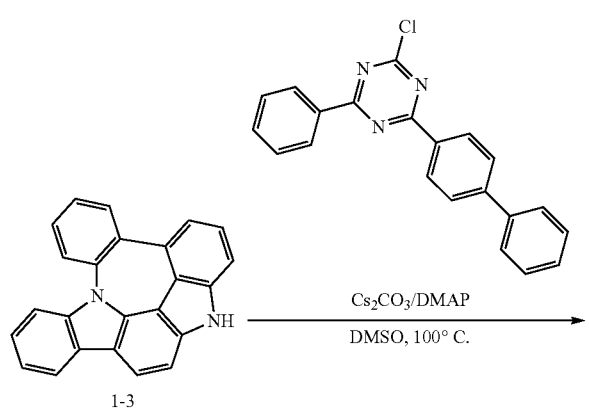

EXAMPLE 5

Preparation of Compound C-21

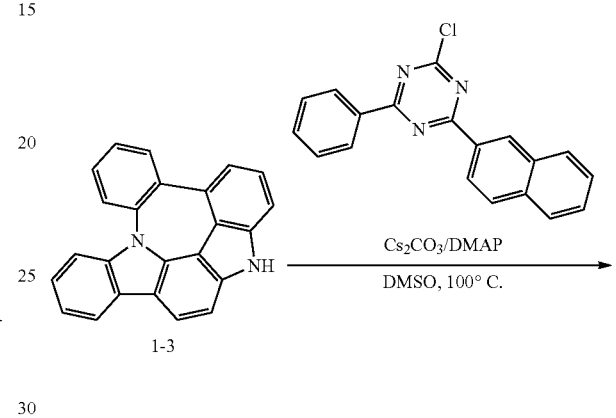

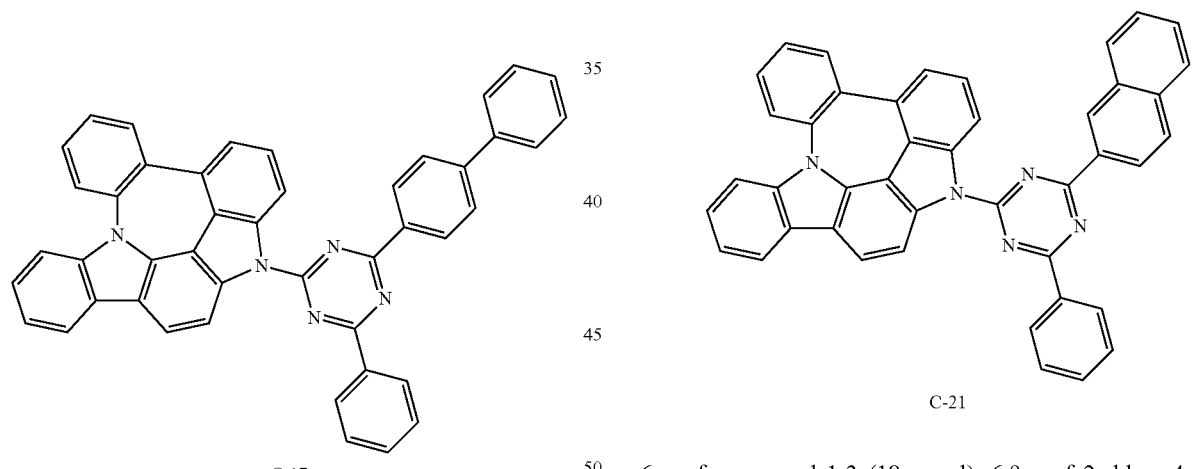

6 g of compound 1-3 (18 mmol), 7.5 g of 2-([1,1'-biphenyl]-4-yl)-4-chloro-6-phenyl-1,3,5-triazine (21 mmol), 5.9 g of cesium carbonate (18 mmol), 1.1 g of 4-dimethylaminopyridine (DMAP) (9 mmol), and 90 mL of dimethylsulfoxide (DMSO) were introduced into a reaction vessel, and the mixture was stirred at 100° C. for 3 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 10.5 g of compound C-17 (yield: 91%).

6 g of compound 1-3 (18 mmol), 6.9 g of 2-chloro-4-(naphthylen-2-yl)-6-phenyl-1,3,5-triazine (21 mmol), 5.9 g of cesium carbonate (18 mmol), 1.1 g of DMAP (9 mmol), and 90 mL of DMSO were introduced into a reaction vessel, and the mixture was stirred at 100° C. for 3 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 10 g of compound C-21 (yield: 90%).

| | MW | UV | PL | M.P. |
|---|---|---|---|---|
| C-21 | 611.69 | 392 nm | 499 nm | 274° C. |

EXAMPLE 6

Preparation of Compound C-11

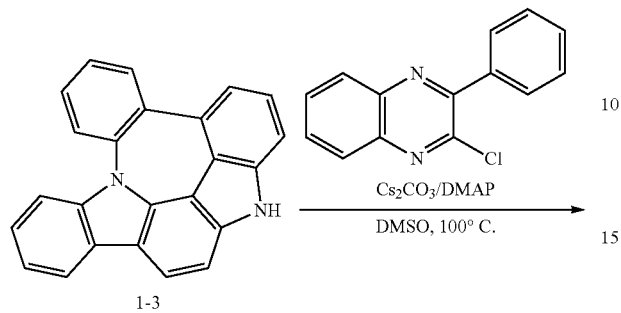

5 g of compound 1-3 (15 mmol), 4.4 g of 2-chloro-3-phenylquinoxaline (18 mmol), 4.9 g of cesium carbonate (15 mmol), 0.9 g of DMAP (8 mmol), and 76 mL of DMSO were introduced into a reaction vessel, and the mixture was stirred at 100° C. for 3 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 1.8 g of compound C-11 (yield: 22%).

|      | MW     | UV     | PL     | M.P.    |
|------|--------|--------|--------|---------|
| C-11 | 534.62 | 332 nm | 529 nm | 180° C. |

EXAMPLE 7

Preparation of Compound C-12

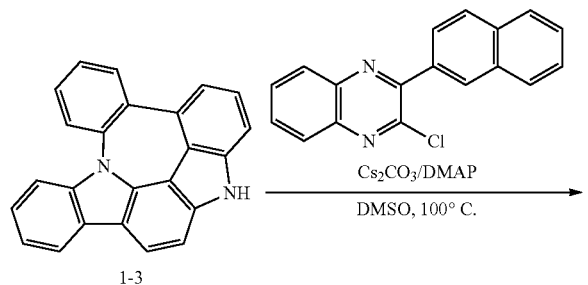

5 g of compound 1-3 (15 mmol), 5.2 g of 2-chloro-3-naphthylquinoxaline (18 mmol), 4.9 g of cesium carbonate (15 mmol), 0.9 g of DMAP (8 mmol), and 76 mL of DMSO were introduced into a reaction vessel, and the mixture was stirred at 100° C. for 3 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 4.2 g of compound C-12 (yield: 48%).

|      | MW     | UV     | PL     | M.P.    |
|------|--------|--------|--------|---------|
| C-12 | 584.68 | 324 nm | 525 nm | 170° C. |

EXAMPLE 8

Preparation of Compound C-67

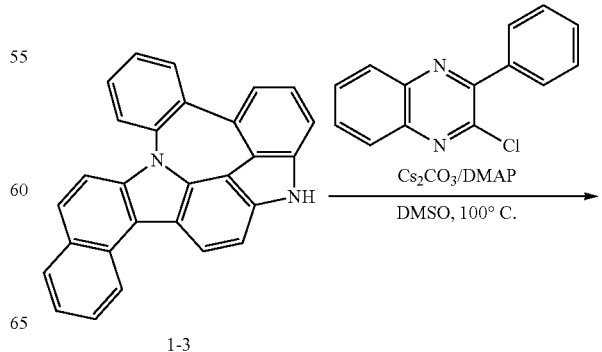

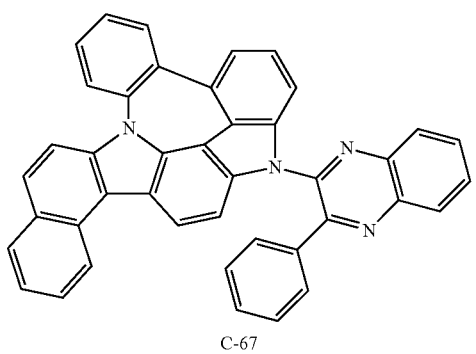

C-67

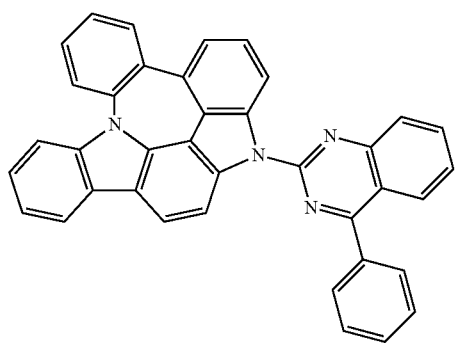

C-1

2.7 g of compound 1-3 (7 mmol), 1.0 g of 2-chloro-3-phenylquinoxaline (4 mmol), 2.3 g of cesium carbonate (7 mmol), 0.5 g of DMAP (4 mmol), and 36 mL of DMSO were introduced into a reaction vessel, and the mixture was stirred at 100° C. for 5 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 1 g of compound C-67 (yield: 40%).

|  | MW | M.P. |
|---|---|---|
| C-67 | 584.67 | 285° C. |

EXAMPLE 9

Preparation of Compound C-1

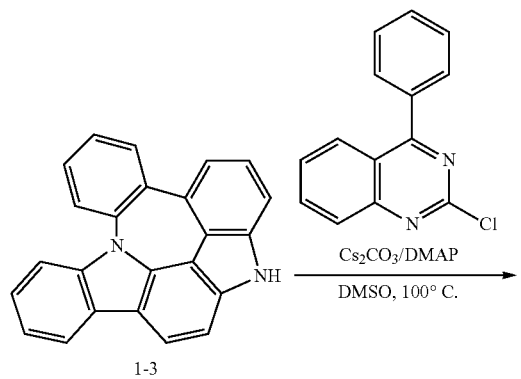

1-3

4 g of compound 1-3 (12 mmol), 3.8 g of 2-chloro-4-phenylquinazoline (16 mmol), 3.9 g of cesium carbonate (12 mmol), 0.7 g of DMAP (6 mmol), and 60 mL of DMSO were introduced into a reaction vessel, and the mixture was stirred at 100° C. for 3 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 5.4 g of compound C-1 (yield: 83%).

|  | MW | UV | PL | M.P. |
|---|---|---|---|---|
| C-1 | 534.62 | 324 nm | 519 nm | 300° C. |

EXAMPLE 10

Preparation of Compound C-101

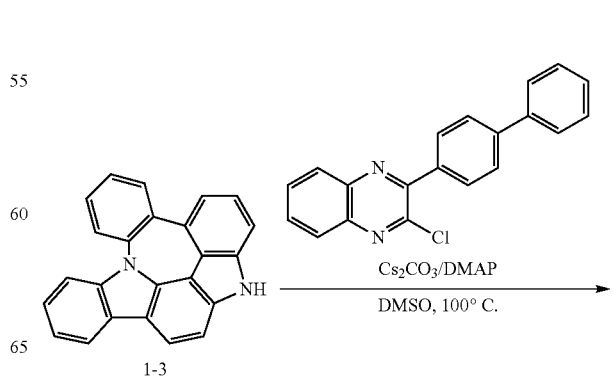

1-3

-continued

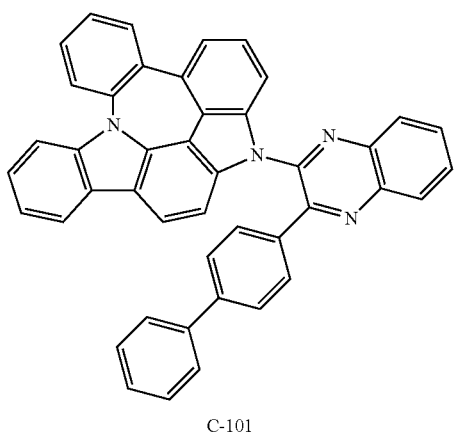

C-101

-continued

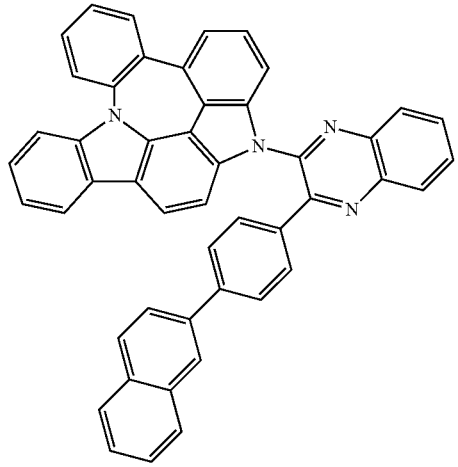

C-102

5 g of compound 1-3 (15 mmol), 5.7 g of 2-([1,1'-biphenyl]-4-yl)-3-chloroquinoxaline (18 mmol), 4.9 g of cesium carbonate (15 mmol), 0.9 g of DMAP (8 mmol), and 76 mL of DMSO were introduced into a reaction vessel, and the mixture was stirred at 100° C. for 3 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 5.0 g of compound C-101 (yield: 55%).

|  | MW | M.P. |
|---|---|---|
| C-101 | 610.72 | 182° C. |

EXAMPLE 11

Preparation of Compound C-102

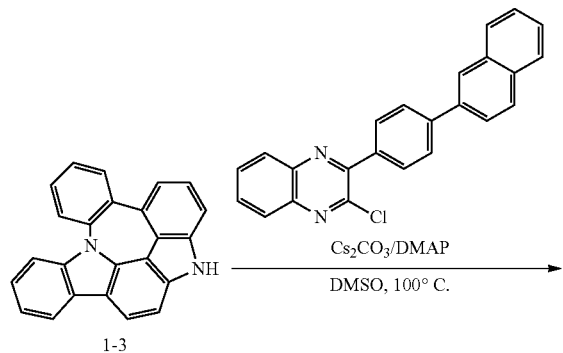

3 g of compound 1-3 (9 mmol), 4.0 g of 2-chloro-3-(4-(naphthalen-2-yl)phenyl)quinoxaline (11 mmol), 2.9 g of cesium carbonate (9 mmol), 0.4 g of DMAP (4 mmol), and 45 mL of DMSO were introduced into a reaction vessel, and the mixture was stirred at 100° C. for 5 hours. After completion of the reaction, the mixture was washed with distilled water, extracted with ethyl acetate, and the extracted organic layer was dried with magnesium sulfate. The solvent was removed with a rotary evaporator, and the resulting product was purified by column chromatography to obtain 1.8 g of compound C-102 (yield: 31%).

|  | MW | M.P. |
|---|---|---|
| C-102 | 660.78 | 186° C. |

DEVICE EXAMPLE 1

Production of an OLED Device Using the Organic Electroluminescent Compound According to the Present Disclosure An OLED device was produced using the organic electroluminescent compound of the present disclosure. A transparent electrode indium tin oxide (ITO) thin film (10 Ω/sq) on a glass substrate for an organic light-emitting diode (OLED) device (Geomatec, Japan) was subjected to an ultrasonic washing with acetone, ethanol, and distilled water, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. Compound HT-3 was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. Compound C-50 was introduced into one cell of the vacuum vapor depositing apparatus as a host, and compound D-71 was introduced into another cell as a dopant. The two materials were evaporated and were deposited in a doping amount of 3 wt % based on the total amount of the host and dopant to form a light-emitting layer having a thickness of 40 nm on the second hole transport layer. Compound ET-1 and compound EI-1 were then introduced into other two cells, evaporated at the rate of 1:1, and deposited to form an electron transport layer having a thickness of 30 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced.

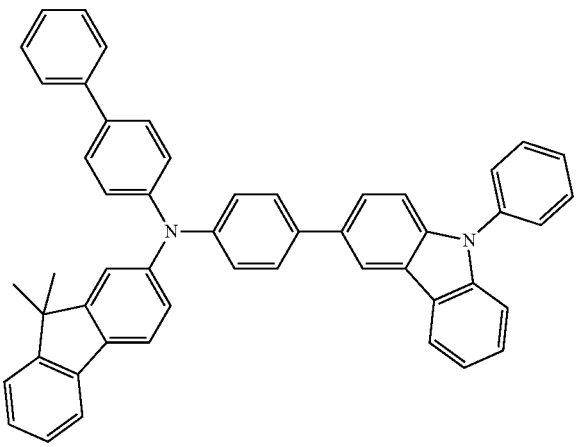

HT-1

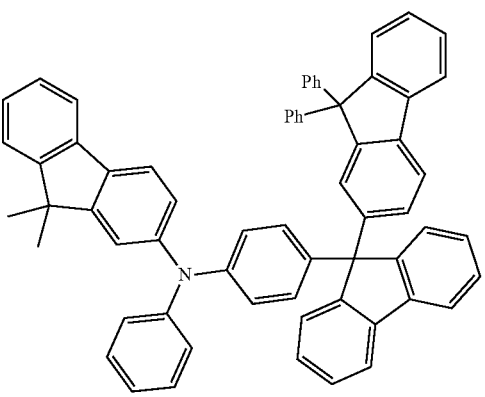

HT-3

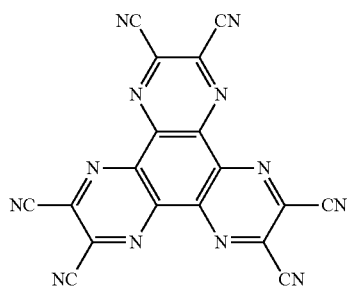

HI-1

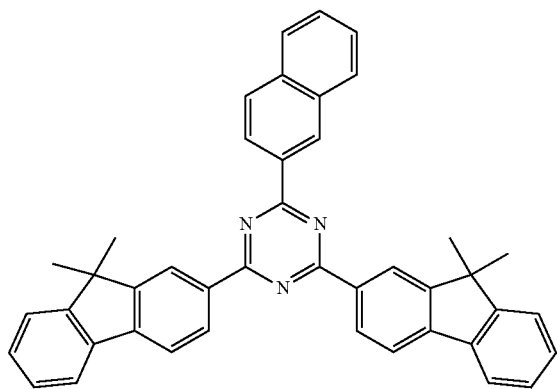

ET-1

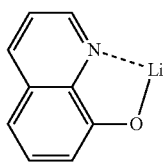

EI-1

HI-2

As a result, an efficiency of 28.6 cd/A at 3.5 V was shown, red light of 1000 cd/m² was emitted, and the least time taken to be reduced from 100% to 95% of the luminance at 5,000 nits was 95 hours.

COMPARATIVE EXAMPLE 1

Production of an OLED Device Using a Conventional Organic Electroluminescent Compound An OLED device was produced in the same manner as in Device Example 1, except that compound B was used instead of compound C-50.

As a result, an efficiency of 14.3 cd/A at 10 V was shown, red light of 1000 cd/m² was emitted, and the least time taken to be reduced from 100% to 95% of the luminance at 5,000 nits was 0.1 hour.

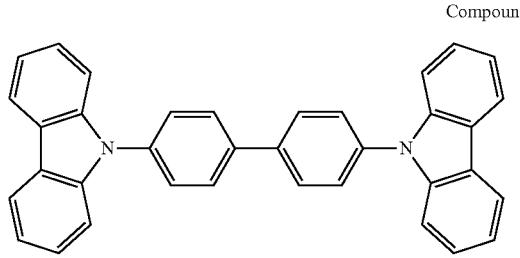

Compound B

COMPARATIVE EXAMPLE 2

Production of an OLED Device Using a Conventional Organic Electroluminescent Compound An OLED device was produced in the same manner as in Device Example 1, except that compound Y was used instead of compound C-50.

As a result, an efficiency of 26.2 cd/A at 4.0 V was shown, red light of 1000 cd/m² was emitted, and the least time taken to be reduced from 100% to 95% of the luminance at 5,000 nits was 34 hours.

Compound Y

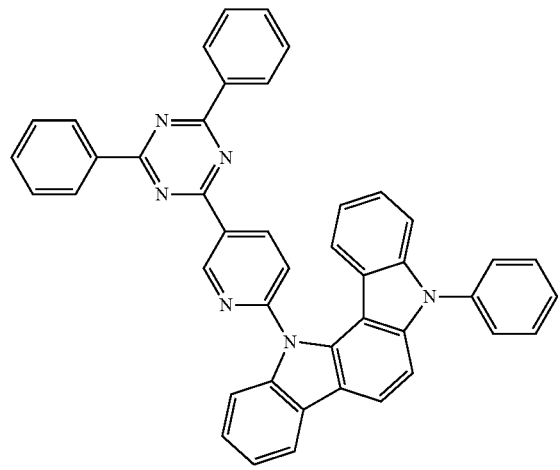

COMPARATIVE EXAMPLE 3

Production of an OLED Device not According to the Present Disclosure and Emitting Red Light An OLED device was produced in the same manner as in Device Example 1, except that 4,4'-N,N'-dicarbazol-biphenyl (CBP) was used as a host material instead of compound C-50, compound HT-4 was used as a second hole transport layer material instead of compound HT-3, and the thickness of the electron transport layer was changed to 35 nm.

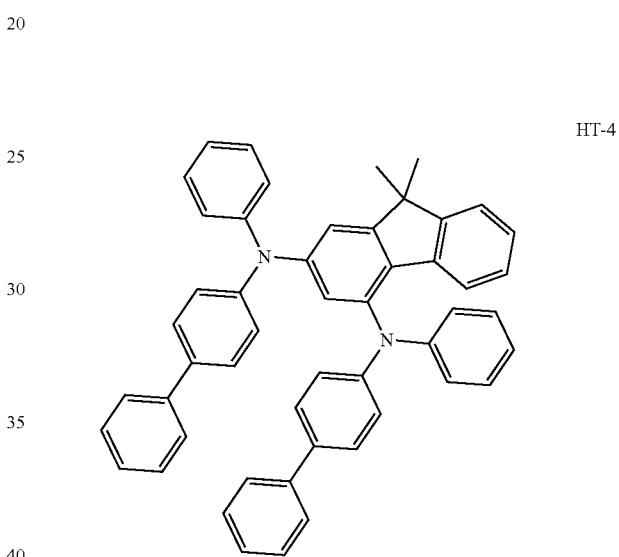

HT-4

DEVICE EXAMPLES 2 to 11

Production of OLED Devices According to the Present Disclosure and Emitting Red Light OLED devices were produced in the same manner as in Comparative Example 3, except that the host was changed to the compounds shown in Table 1 below.

The driving voltage, luminous efficiency, and CIE color coordinates at 1,000 nits, and the lifespan (T95) measured as the time taken to be reduced from 100% to 95% of the luminance at 5,000 nits of the OLED devices produced in Comparative Example 3 and Device Examples 2 to 11 are provided in Table 1 below.

TABLE 1

| Host | Driving voltage [V] | Luminous efficiency (cd/A) | Color coordinate (x) | Color coordinate (y) | Lifespan (T95, hr) |
|---|---|---|---|---|---|
| Comparative Example 3 | CBP | 9.2 | 9.2 | 0.663 | 0.334 | 0.24 |
| Device Example 2 | C-51 | 3.1 | 25.7 | 0.673 | 0.326 | 196.7 |
| Device Example 3 | C-49 | 3.4 | 27.5 | 0.672 | 0.328 | 167.5 |
| Device Example 4 | C-17 | 3.5 | 26.5 | 0.673 | 0.327 | 261.6 |
| Device Example 5 | C-21 | 3.6 | 25.4 | 0.674 | 0.330 | 189.3 |
| Device Example 6 | C-11 | 3.4 | 29.7 | 0.671 | 0.329 | 163.3 |
| Device Example 7 | C-12 | 3.2 | 28.0 | 0.674 | 0.326 | 50.7 |
| Device Example 8 | C-67 | 3.2 | 26.6 | 0.671 | 0.329 | 204.3 |
| Device Example 9 | C-1 | 3.3 | 25.0 | 0.668 | 0.332 | 350.0 |
| Device Example 10 | C-101 | 3.2 | 26.4 | 0.671 | 0.328 | 173.4 |
| Device Example 11 | C-102 | 3.2 | 25.5 | 0.672 | 0.328 | 162.0 |

When producing organic electroluminescent devices, the organic electroluminescent compounds according to the present disclosure provide lower driving voltage, higher luminous efficiency such as current efficiency, and longer operational lifespan of the devices compared to the conventional organic electroluminescent compounds.

The compound of formula 1 of the present disclosure has an azepine ring formed by a link of a benzene ring, which is substituted on N in an indolocarbazole backbone, and a benzene ring of a carbazole. Such effects of the compound of the present disclosure may be interpreted by the following theory.

The figure shows that the compound of the present disclosure has a reduced steric hindrance compared to the conventional compound. The steric hindrance increases the intermolecular distance, and thus the electron mobility is lowered in electron hopping. Therefore, a hopping distance should be reduced by increasing the current enabling electron hopping. As a result, the driving voltage of the organic electroluminescent device increases. In the figure, since an H—H distance in compound A is too short, N-phenyls are not located on the same plane and are vertically located. Thus, the aforementioned steric hindrance is expected. In order to prevent such phenomenon, compound B of the present disclosure was invented to have a planar structure compared to compound A. Accordingly, the compound of the present disclosure can reduce driving voltage upon applying it to a device.

The invention claimed is:

1. An organic electroluminescent compound represented by the following formula 1:

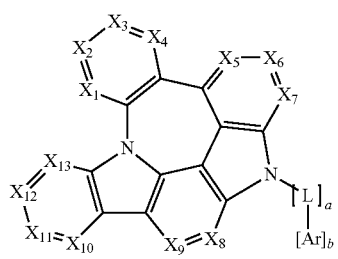

(1)

wherein $X_1$, $X_2$, $X_3$, $X_4$, $X_5$, $X_6$, $X_7$, $X_8$, $X_9$, $X_{10}$, $X_{11}$, $X_{12}$ and $X_{13}$ each independently represent N or $CR_1$;

L represents a single bond, a substituted or unsubstituted (C1-C30)alkylene, a substituted or unsubstituted (C6-C30)arylene, a substituted or unsubstituted 3- to 30-membered heteroarylene, or a substituted or unsubstituted (C3-C30)cycloalkylene;

Ar represents hydrogen, deuterium, a halogen, a cyano, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di- (C6-C30)arylamino, or a substituted or unsubstituted (C1-C30)alkyl(C6-C30)arylamino;

$R_1$ represents hydrogen, deuterium, a halogen, a cyano, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di- (C6-C30)arylamino, or a substituted or unsubstituted (C1-C30)alkyl(C6-C30)arylamino, or are linked to an adjacent substituent to form a substituted or unsubstituted, mono- or polycyclic, (C3-C30) alicyclic or aromatic ring, whose carbon atom(s) may be replaced with at least one heteroatom selected from nitrogen, oxygen, and sulfur;

the heteroaryl(ene) contains at least one heteroatom selected from B, N, O, S, Si, and P; and a and b each independently represent an integer of 1 to 2.

2. The organic electroluminescent compound according to claim 1, wherein the substituents of the substituted (C1-C30)alkyl(ene), the substituted (C6-C30)aryl(ene), the substituted 3- to 30-membered heteroaryl(ene), the substituted (C3-C30)cycloalkyl(ene), the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di- (C1-C30)alkylamino, the substituted mono- or di- (C6-C30)arylamino, and the substituted (C1-C30)alkyl(C6-C30)arylamino in Ar, L, and $R_1$, and the substituted mono- or polycyclic, (C3-C30) alicyclic or aromatic ring in $R_1$ each independently are at least one selected from the group consisting of deuterium, a halogen, a cyano, a carboxyl, a nitro, a hydroxyl, a (C1-30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl unsubstituted or substituted with a (C6-C30)aryl, a (C6-C30)aryl unsubstituted or substituted with a 5- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di- (C6-C30) arylamino unsubstituted or substituted with a (C1-C30) alkyl, a (C1-C30)alkyl(C6-C30)arylamino, a (C1-C30)alkylcarbonyl, a (C1-C30)alkoxycarbonyl, a (C6-C30) arylcarbonyl, a di(C6-C30)arylboronyl, a di(C1-C30) alkylboronyl, a (C1-C30)alkyl(C6-C30)arylboronyl, a (C6-C30)aryl(C1-C30)alkyl, and a (C1-C30)alkyl(C6-C30)aryl.

3. The organic electroluminescent compound according to claim 1, wherein formula 1 is represented by any one of the following formulas 2, 3, 4, 5, 6 and 7:

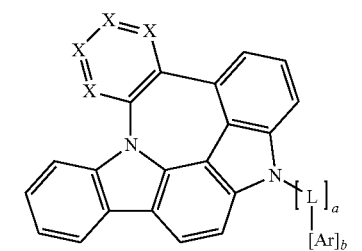
(2)

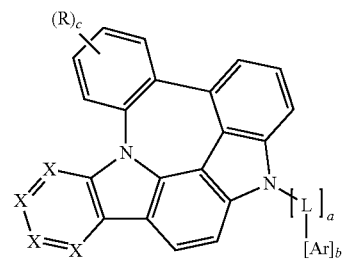
(3)

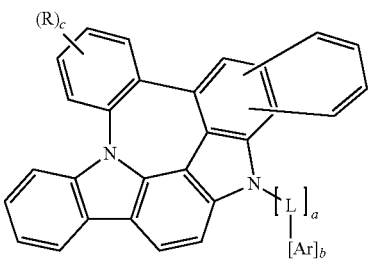
(4)

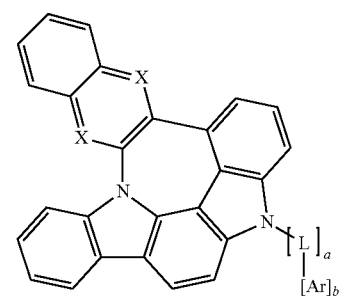
(5)

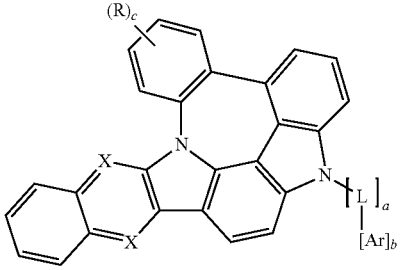
(6)

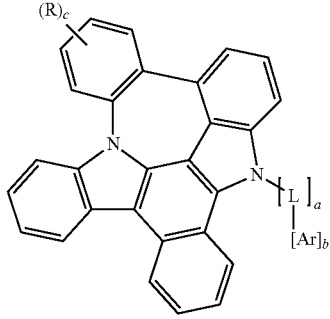
(7)

wherein

X represents N or $CR_1$;

R represents a substituted or unsubstituted mono- or di-(C6-C30)arylamino;

c represents an integer of 1 to 2; and

L, Ar, $R_1$, a, and b are as defined in claim 1.

4. The organic electroluminescent compound according to claim 1, wherein $X_1, X_2, X_3, X_4, X_5, X_6, X_7, X_8, X_9, X_{10}, X_{11}, X_{12}$ and $X_{13}$ each independently represent N or $CR_1$;

L represents a single bond, a substituted or unsubstituted (C6-C15)arylene, or a substituted or unsubstituted 5- to 15-membered heteroarylene;

Ar represents hydrogen, a substituted or unsubstituted (C6-C20)aryl, a substituted or unsubstituted 5- to 20-membered heteroaryl, or a substituted or unsubstituted di(C6-C15)arylamino, and $R_1$ represents hydrogen, or a substituted or unsubstituted di(C6-C15)arylamino; or is linked to an adjacent substituent to form a substituted or unsubstituted, mono- or polycyclic, (C3-C15) alicyclic or aromatic ring, whose carbon atom(s) may be replaced with at least one heteroatom selected from nitrogen, oxygen, and sulfur.

5. The organic electroluminescent compound according to claim 1, wherein $X_1, X_2, X_3, X_4, X_5, X_6, X_7, X_8, X_9, X_{10}, X_{11}, X_{12}$ and $X_{13}$ each independently represent N or $CR_1$;

L represents a single bond, an unsubstituted (C6-C15) arylene, or an unsubstituted 5- to 15-membered heteroarylene;

Ar represents hydrogen; an unsubstituted (C6-C20)aryl; a 5- to 20-membered heteroaryl unsubstituted or substituted with a (C1-C6)alkyl, a (C6-C25)aryl, a 5- to 20-membered heteroaryl, or a (C1-C6)alkyl(C6-C15) aryl; or an unsubstituted di(C6-C15)arylamino; and $R_1$ represents hydrogen, or a di(C6-C15)arylamino unsubstituted or substituted with a (C1-C6)alkyl; or is linked to an adjacent substituent to form an unsubstituted monocyclic (C3-C15) aromatic ring.

6. The organic electroluminescent compound according to claim 1, wherein Ar is a substituted or unsubstituted phenyl, a substituted or unsubstituted naphthyl, a substituted or unsubstituted biphenyl, a substituted or unsubstituted terphenyl, a substituted or unsubstituted triazinyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted dibenzothiophenyl, a substituted or unsubstituted benzothiophenyl, a substituted or unsubstituted dibenzofuranyl, or a substituted or unsubstituted benzofuranyl.

7. The organic electroluminescent compound according to claim 1, wherein the compound represented by formula 1 is selected from the group consisting of:

C-1
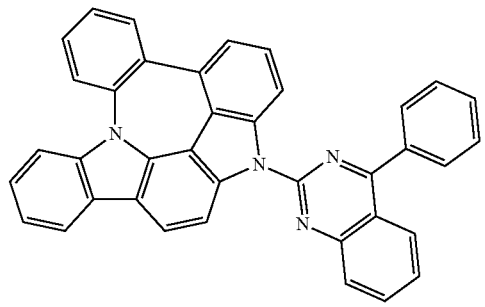

C-2
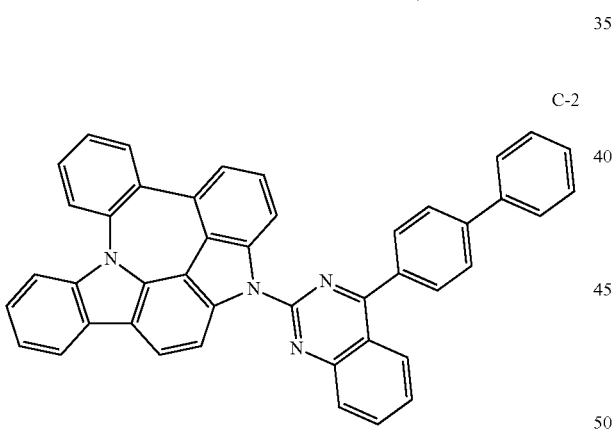

C-3
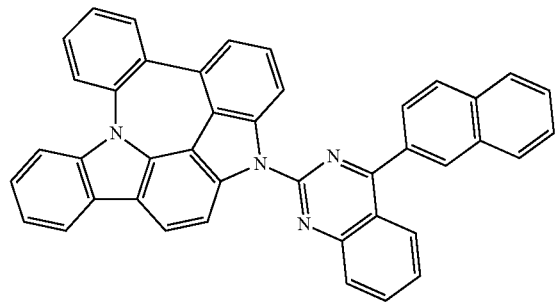

C-4
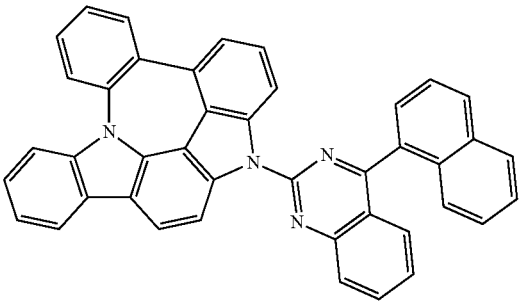

C-5
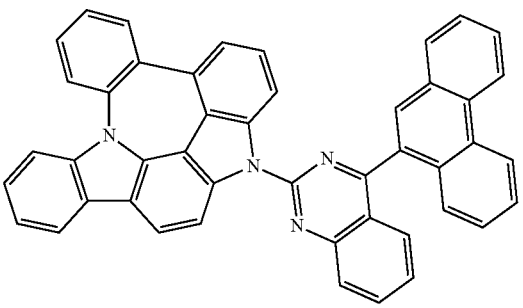

C-6
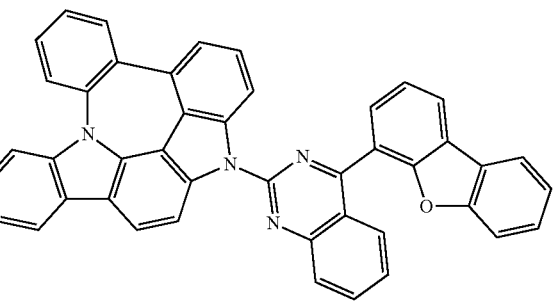

C-7
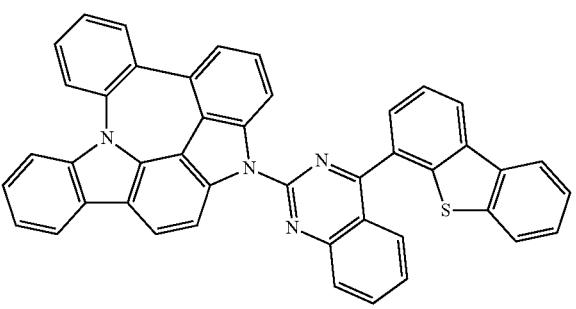

-continued
C-8
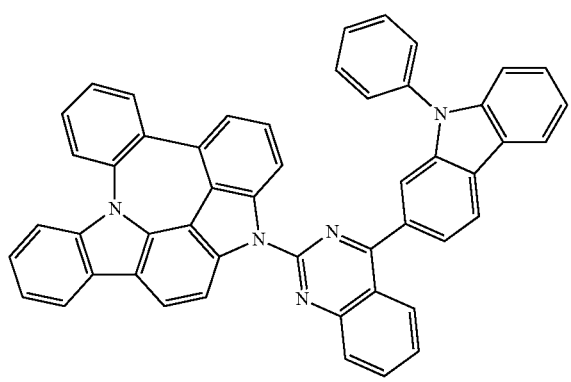
C-9
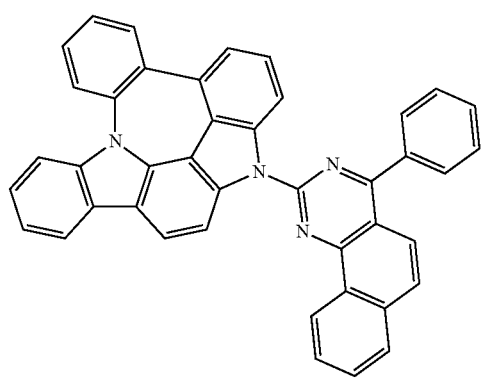
C-10
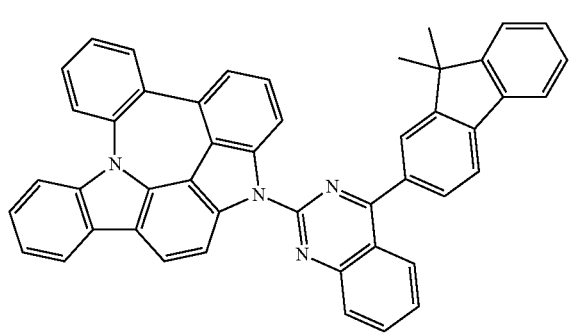
C-11
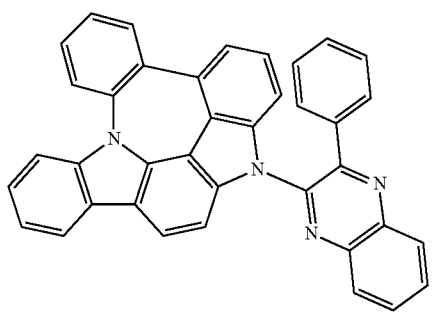
-continued
C-12
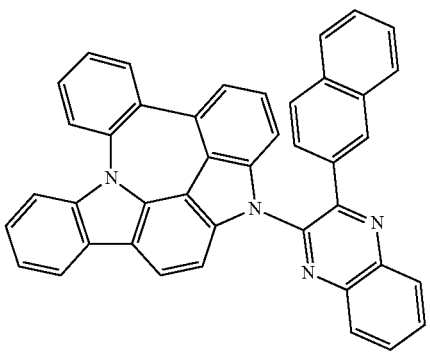
C-13
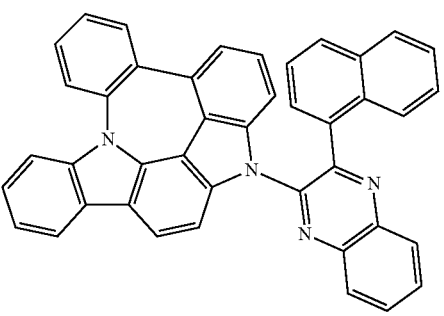
C-14
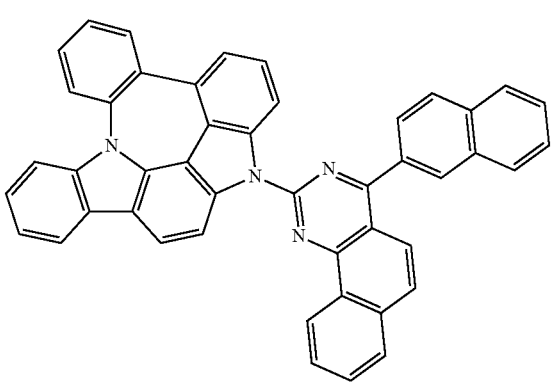
C-15
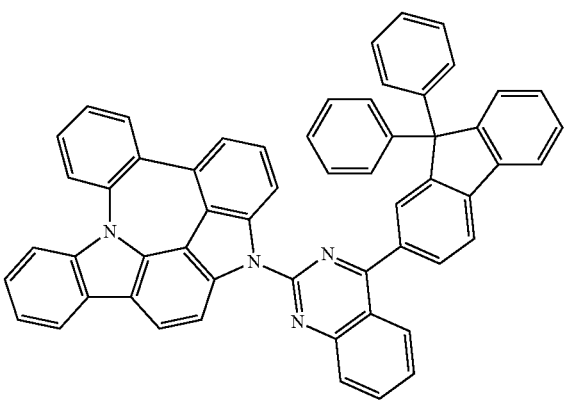

C-16 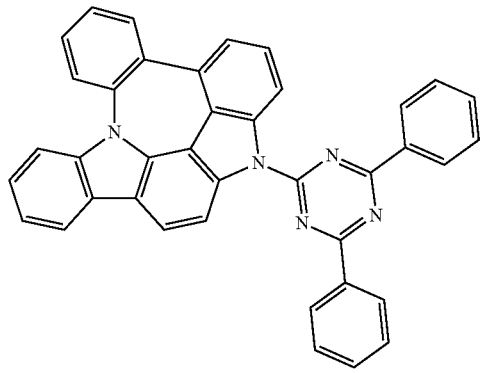
C-20 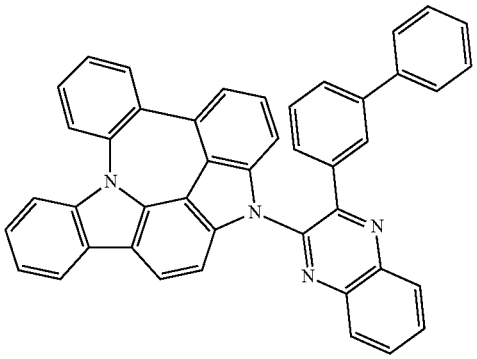
C-17 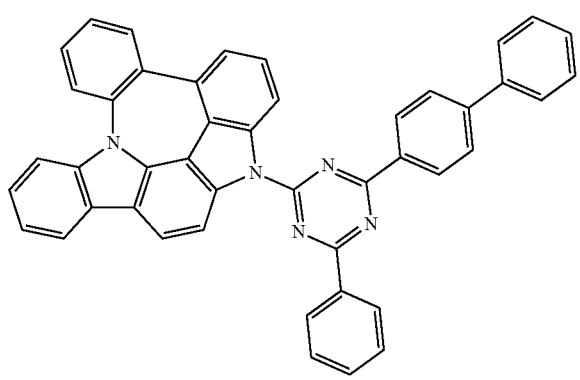
C-21 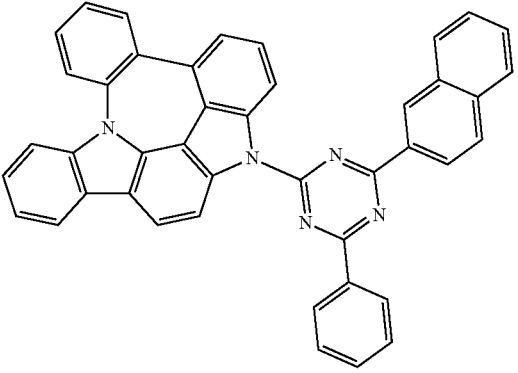
C-18 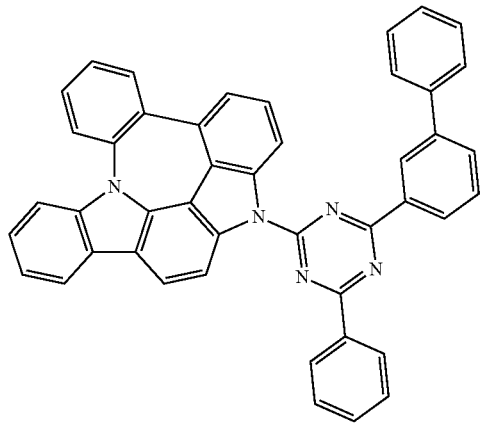
C-22 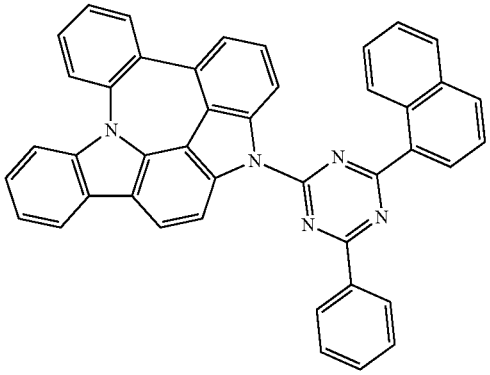
C-19 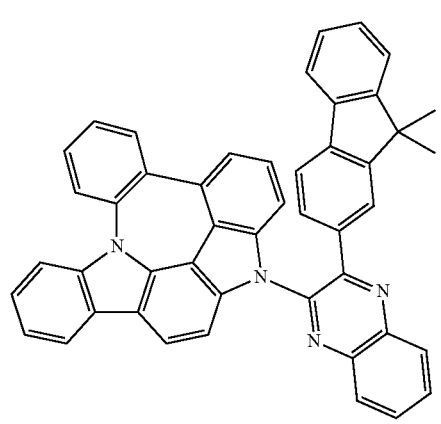
C-23 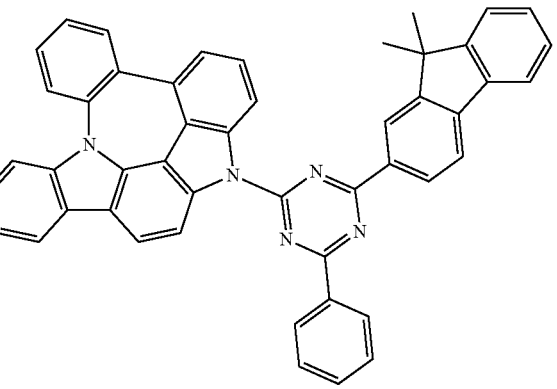

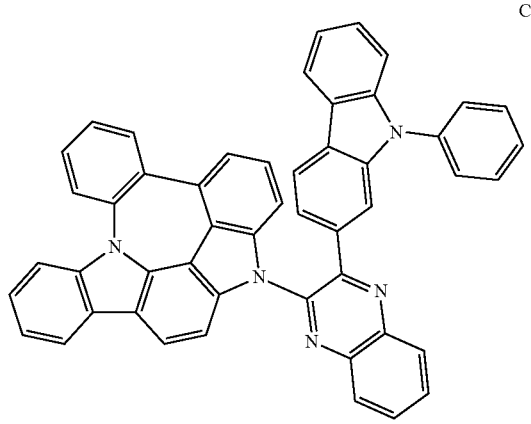 C-24
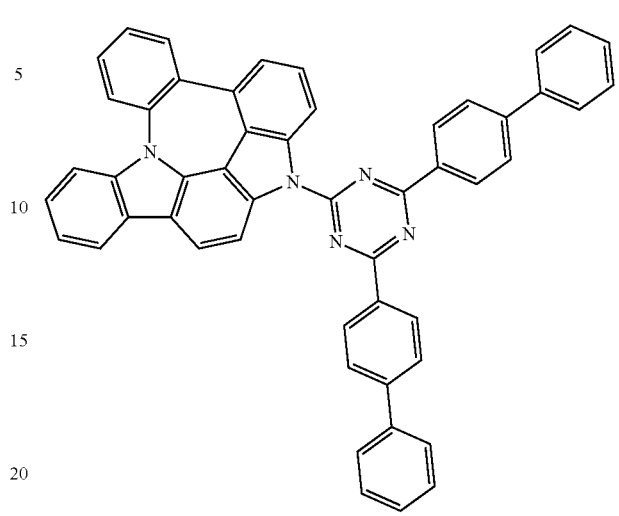 C-27
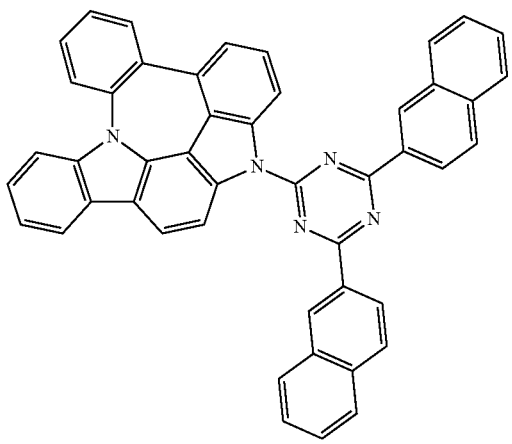 C-25
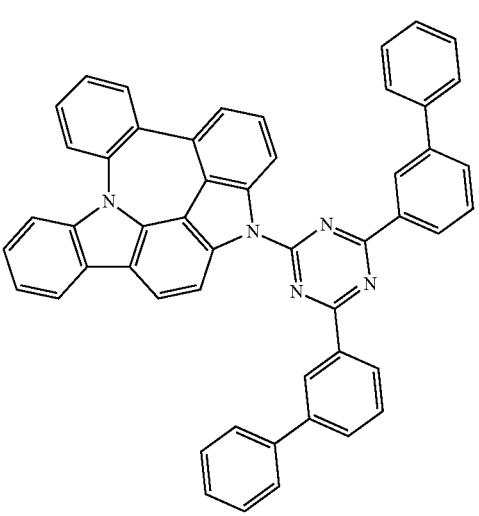 C-28
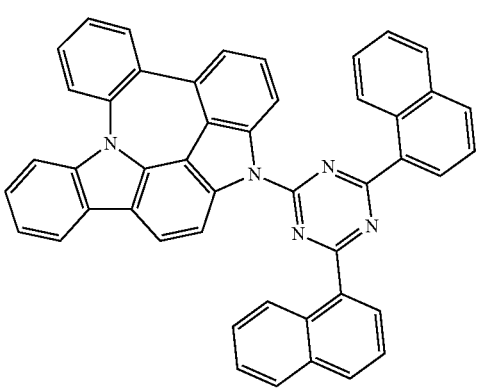 C-26
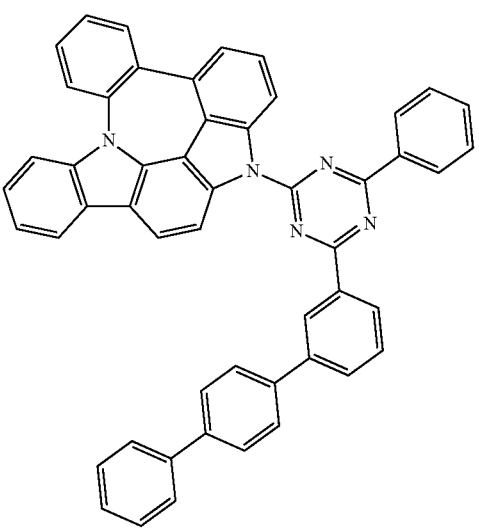 C-29

-continued
C-30
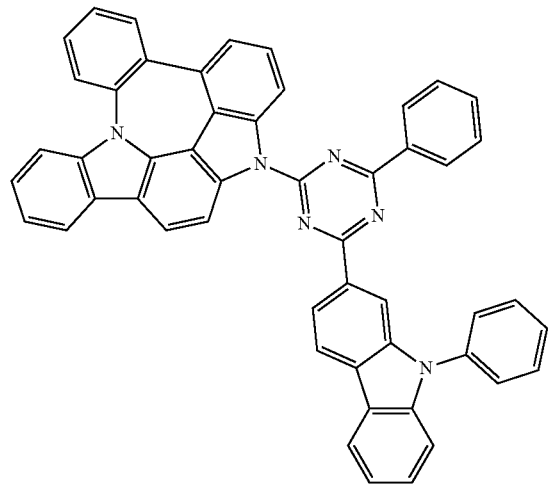
C-31
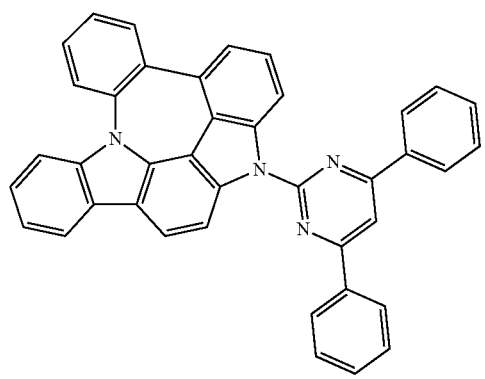
C-32
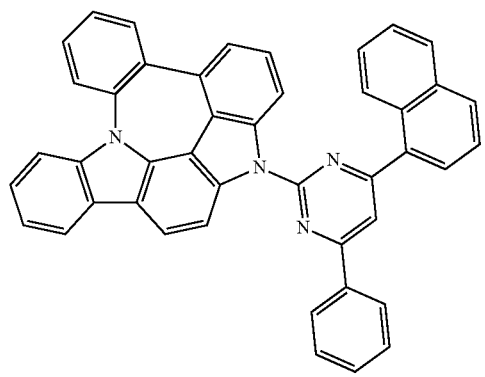
C-33
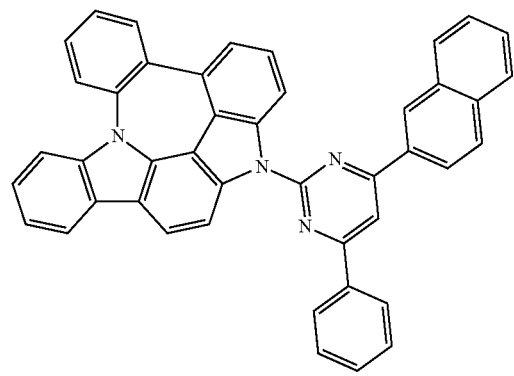
-continued
C-34
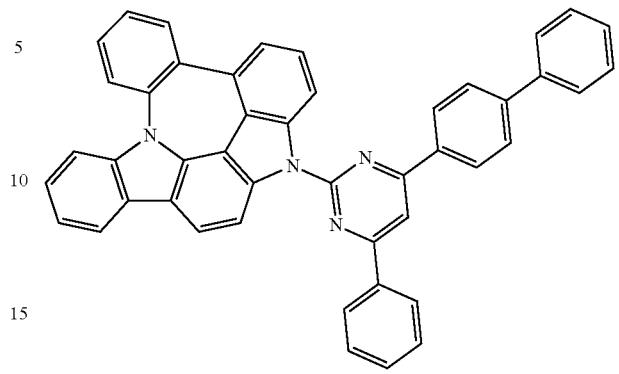
C-35
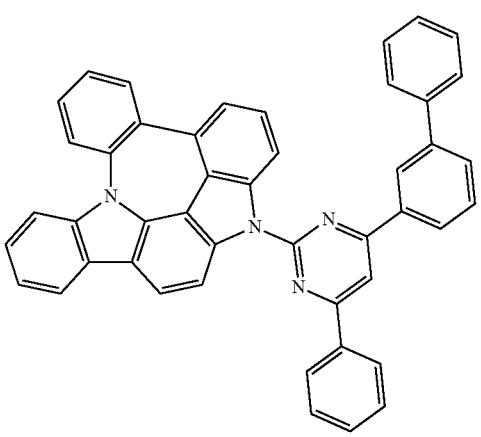
C-36
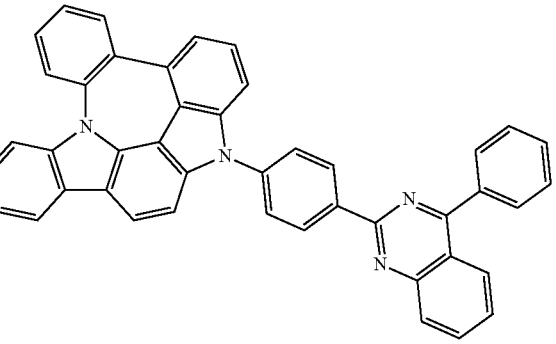
C-37
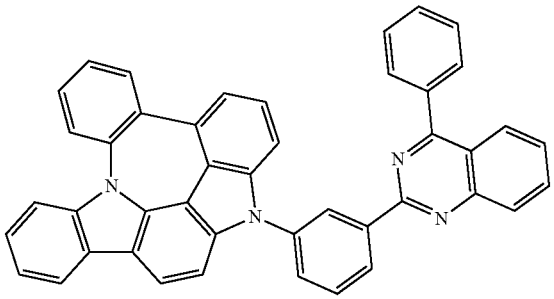

C-38
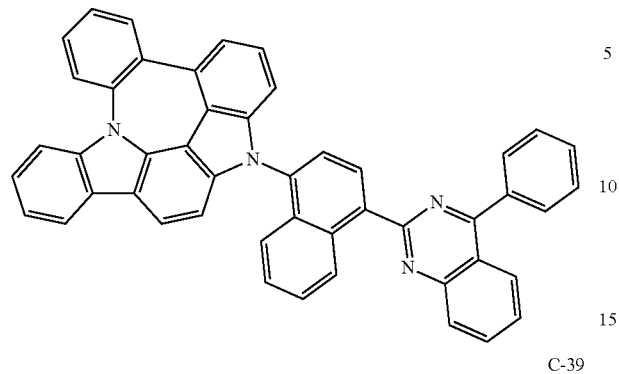
C-42
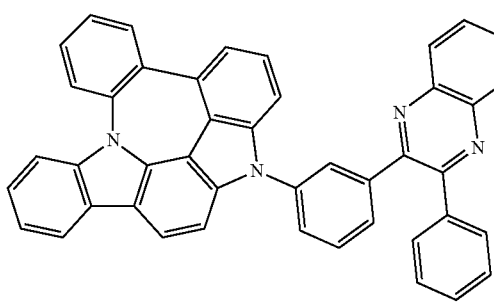
C-39
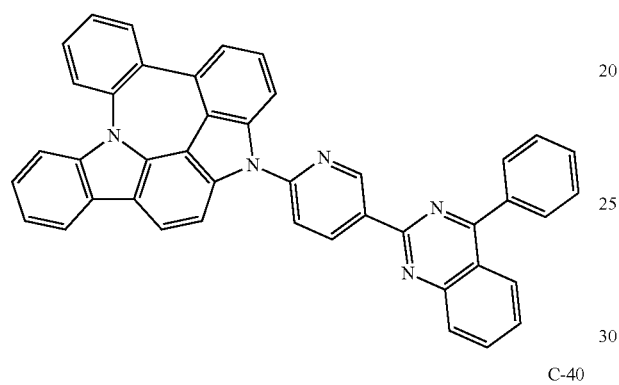
C-43
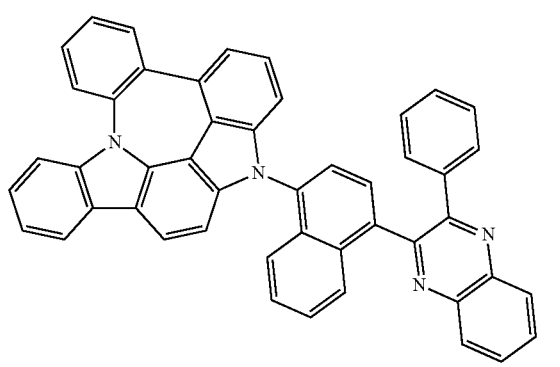
C-40
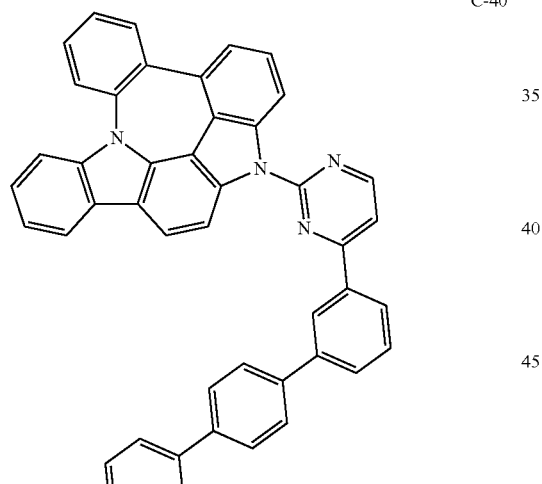
C-44
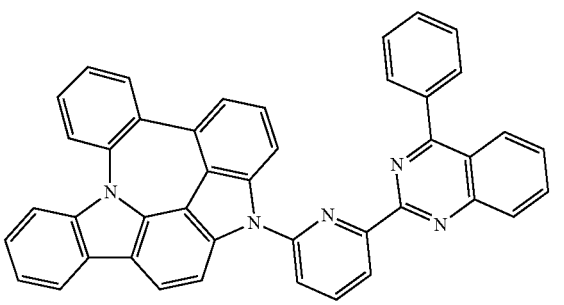
C-41
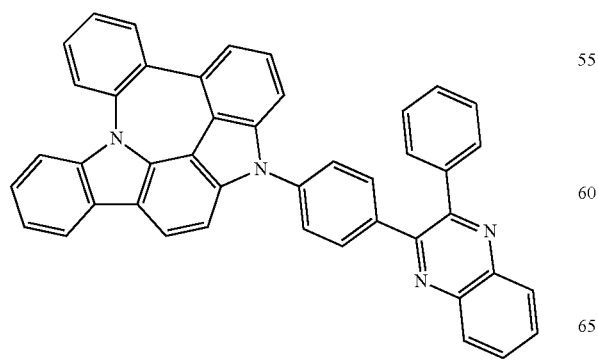
C-45

C-46
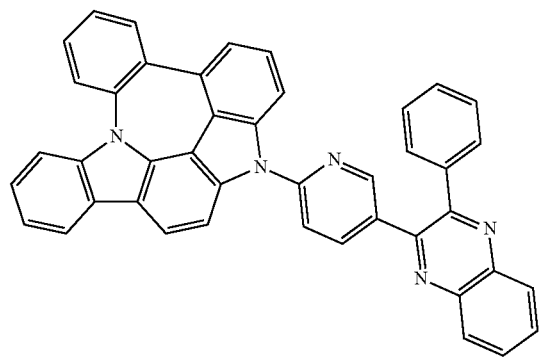
C-47
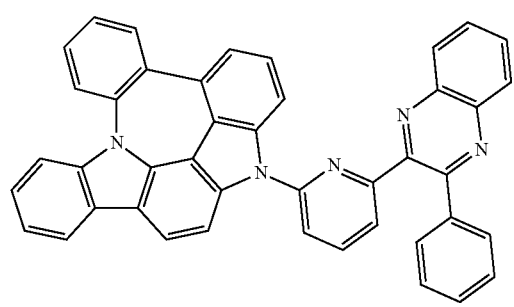
C-48
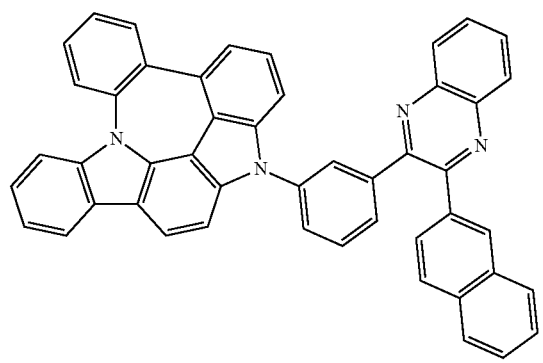
C-49
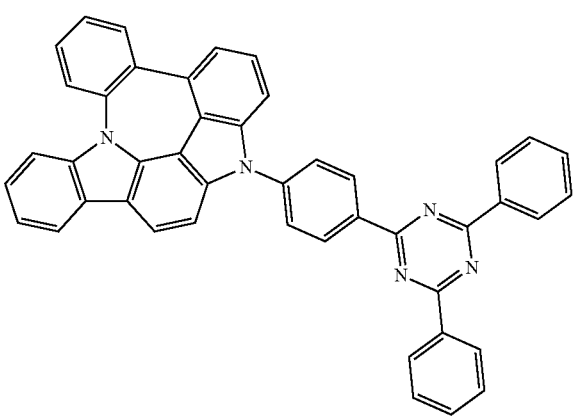
C-50
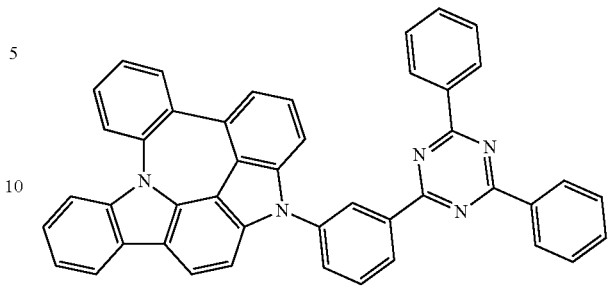
C-51
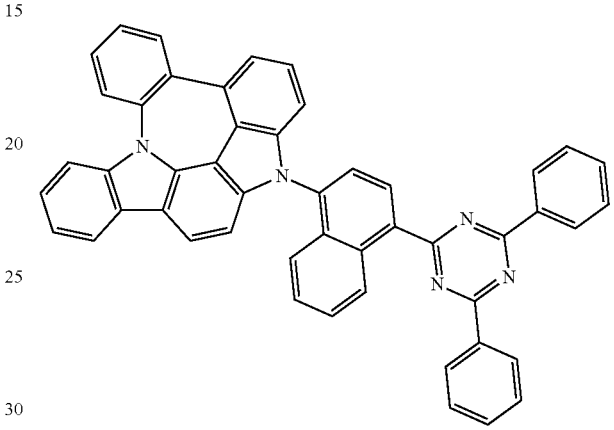
C-52
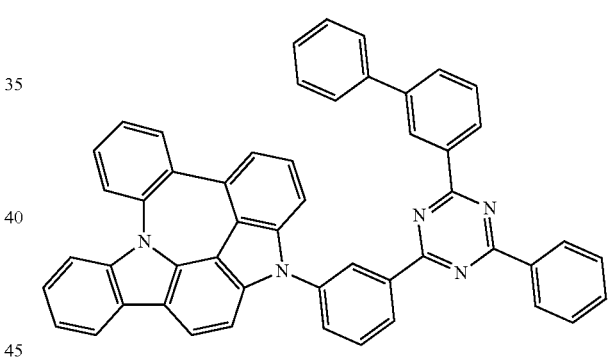
C-53
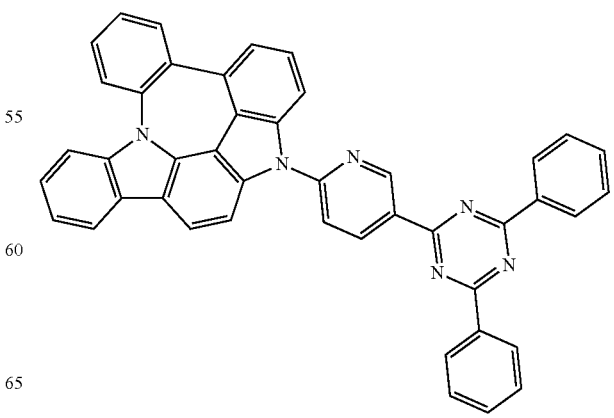

C-54
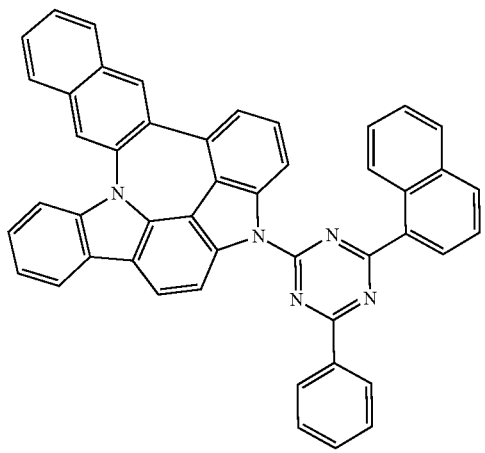
C-55
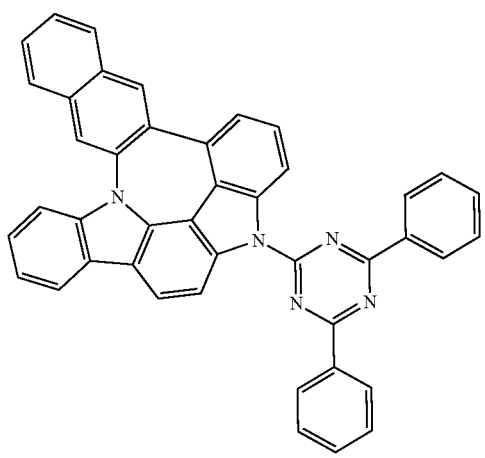
C-56
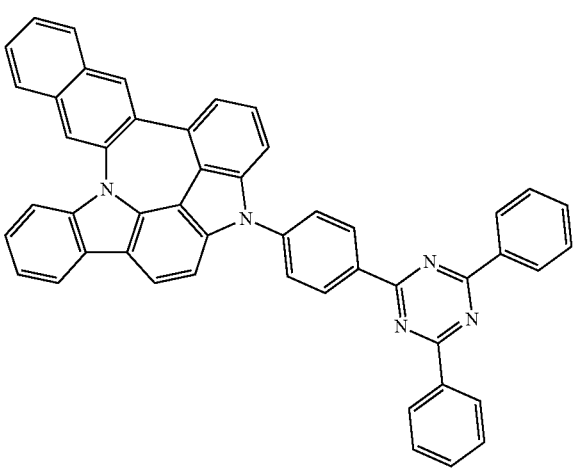
C-57
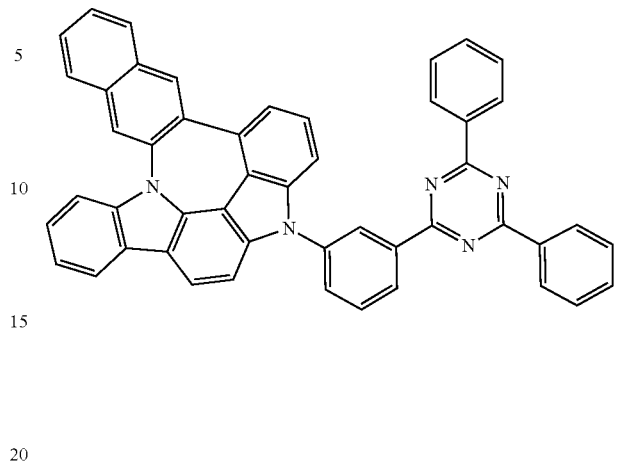
C-58
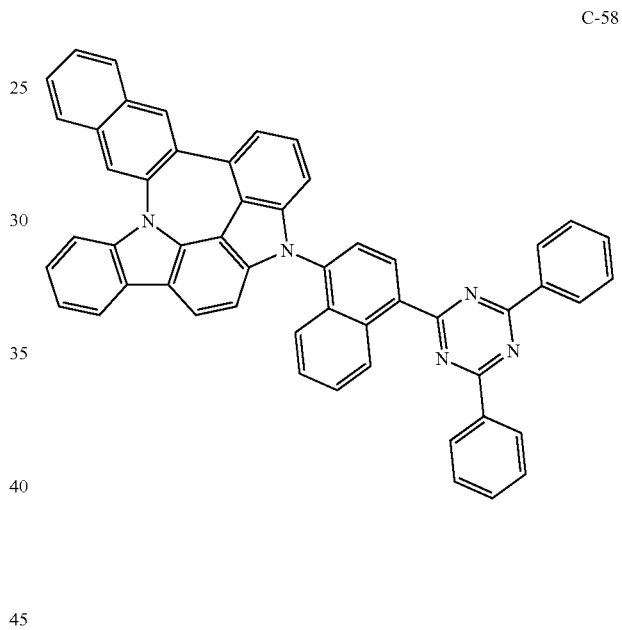
C-59
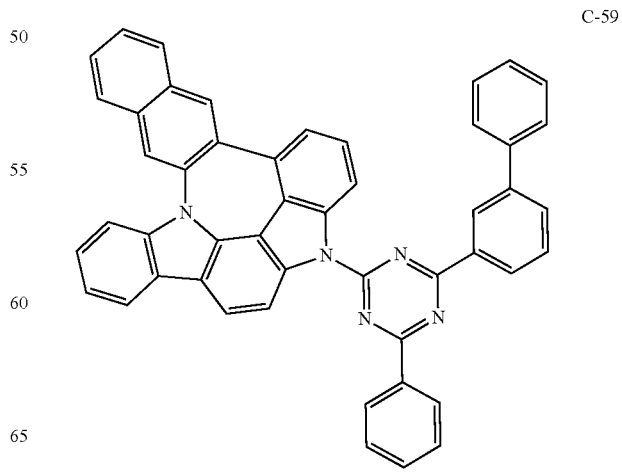

C-60
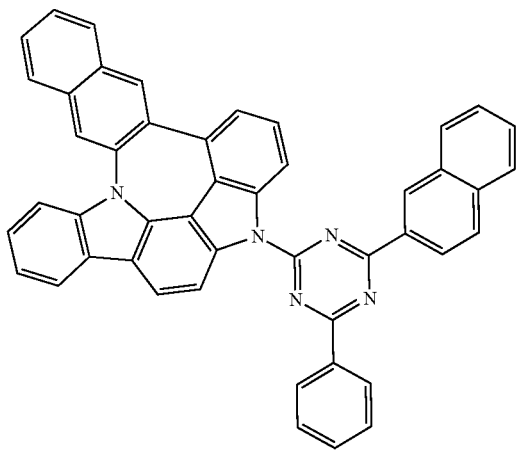
C-61
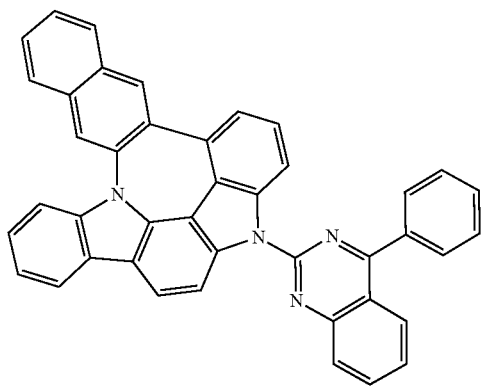
C-62
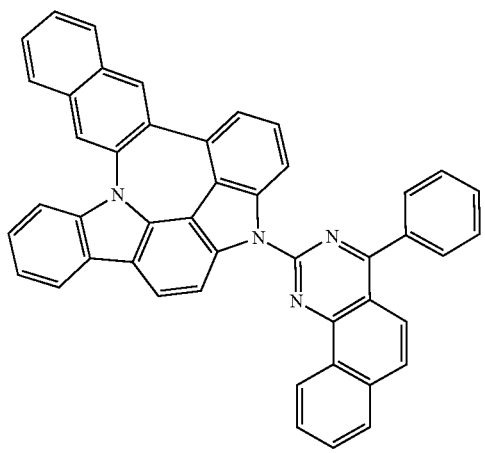
C-63
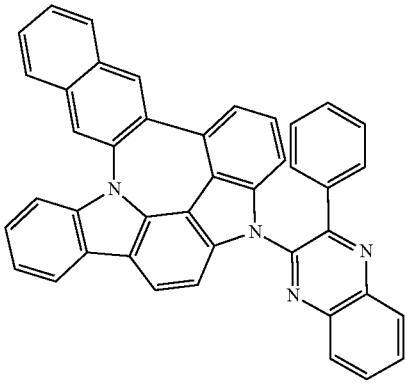
C-64
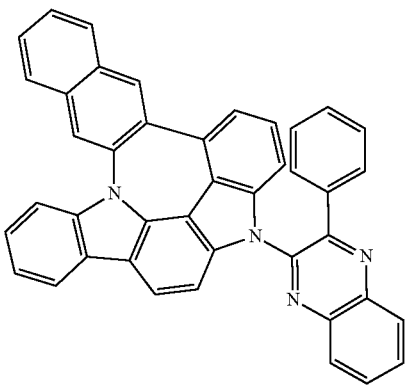
C-65
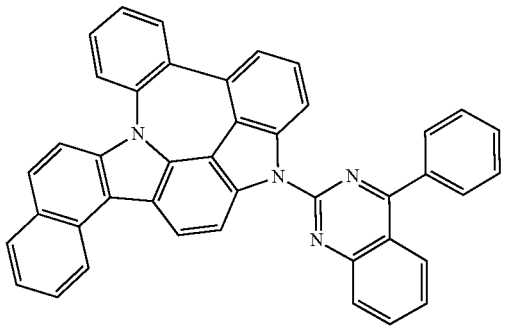
C-66
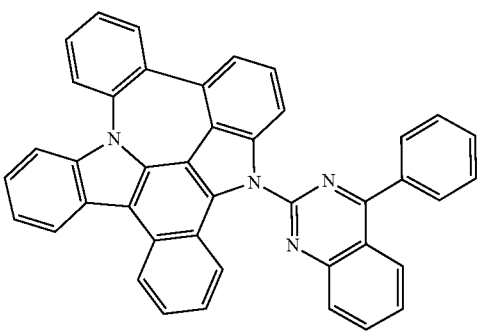

-continued
C-67
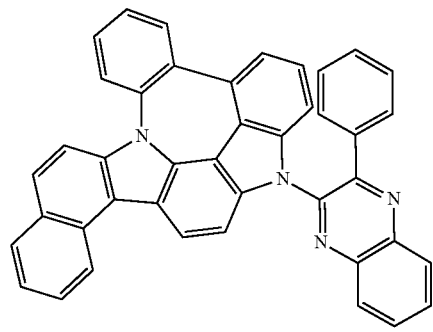
C-68
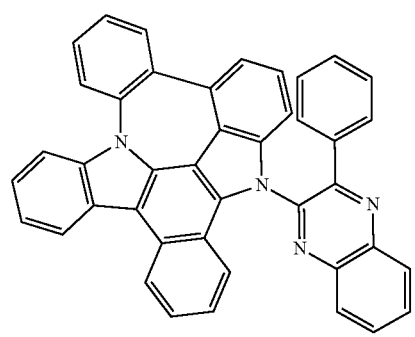
C-69
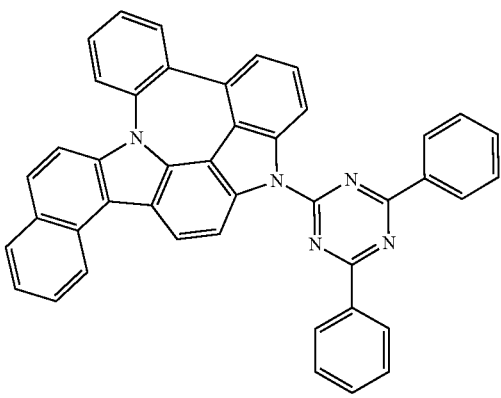
C-70
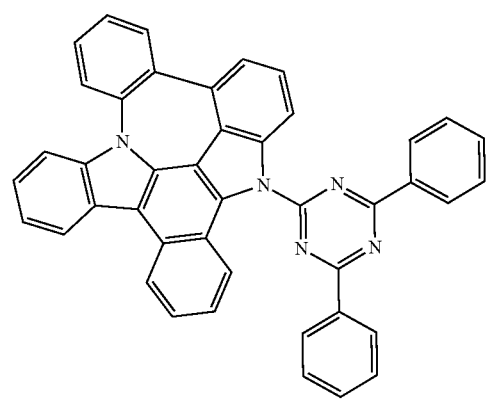
-continued
C-71
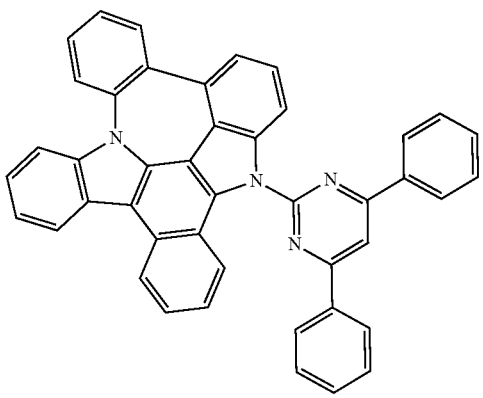
C-72
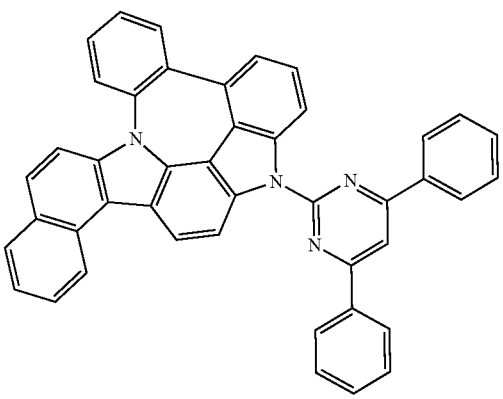
C-73
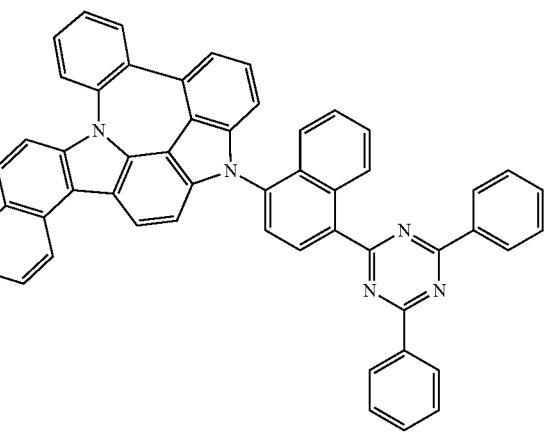

-continued
C-74
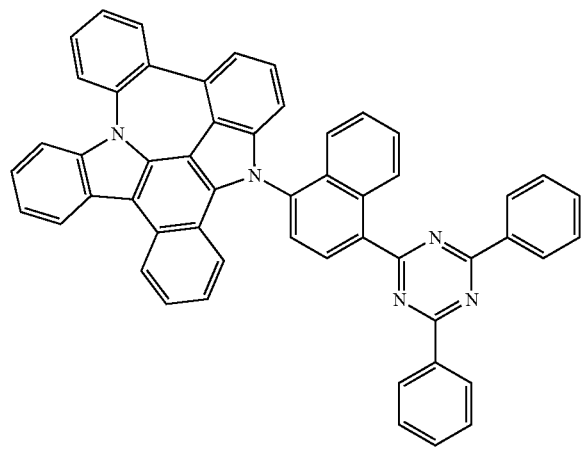
C-75
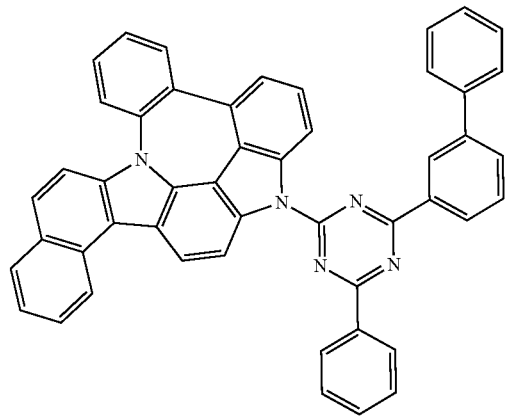
C-76
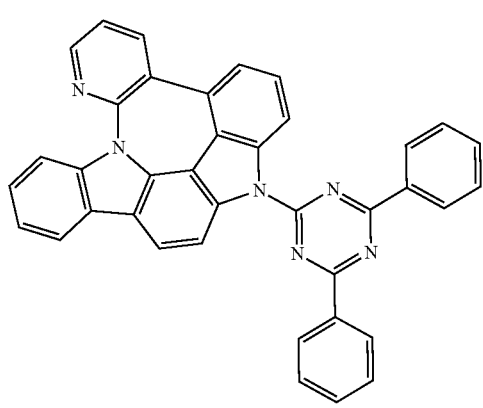
C-77
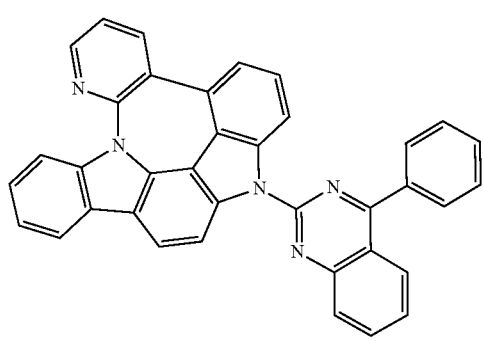
-continued
C-78
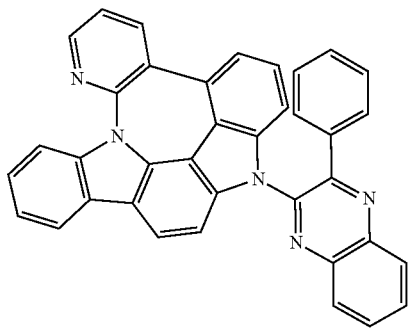
C-79
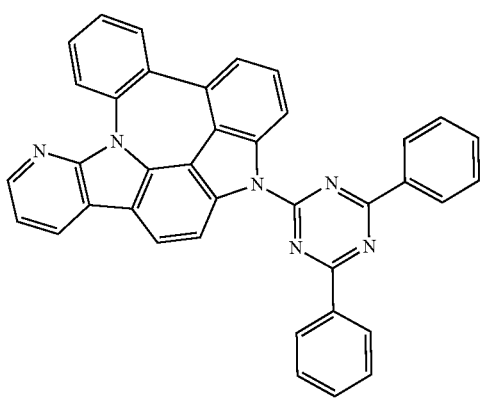
C-80
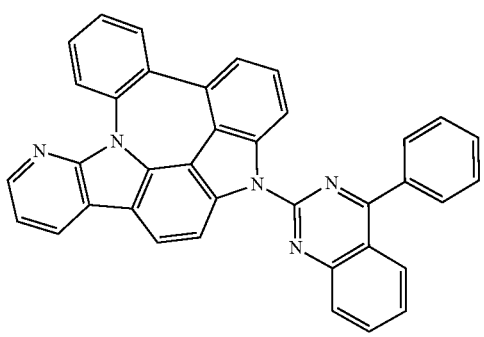
C-81
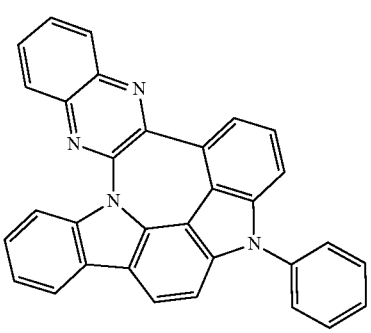

C-82
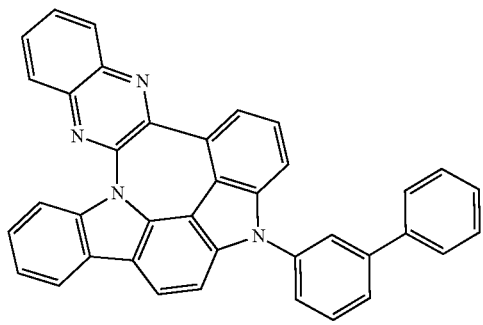
C-83
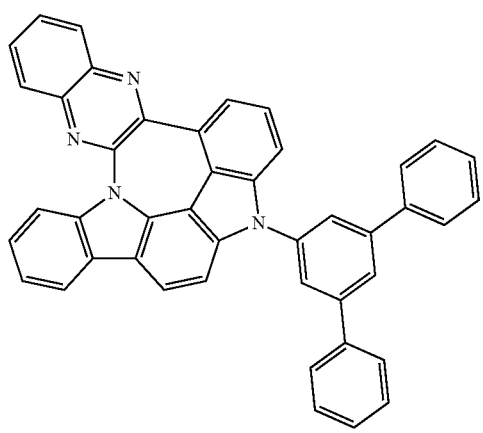
C-84
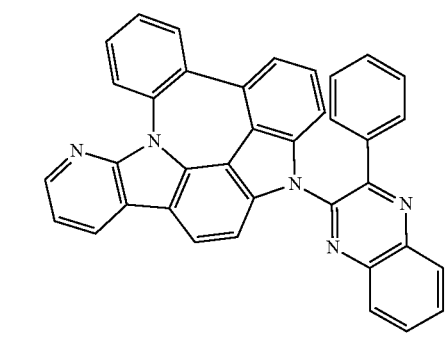
C-85
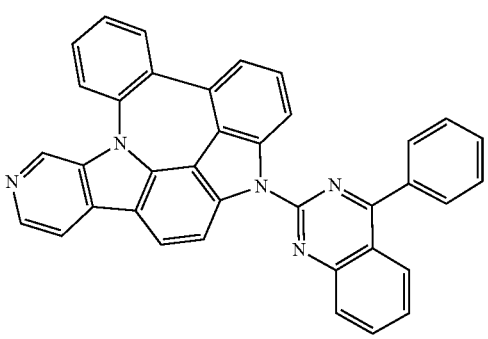
C-86
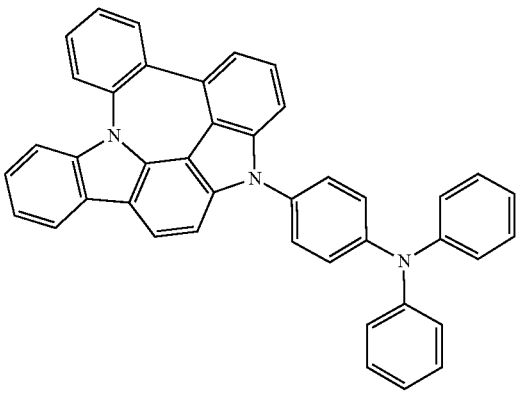
C-87
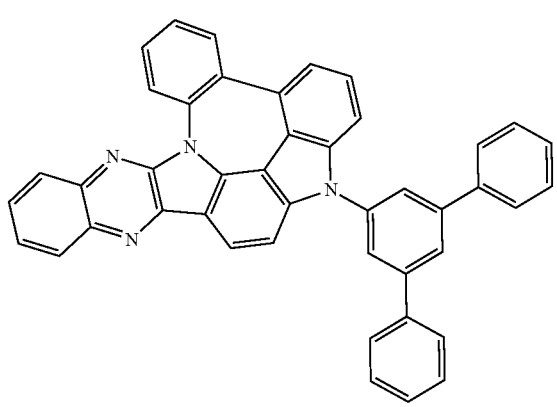
C-88
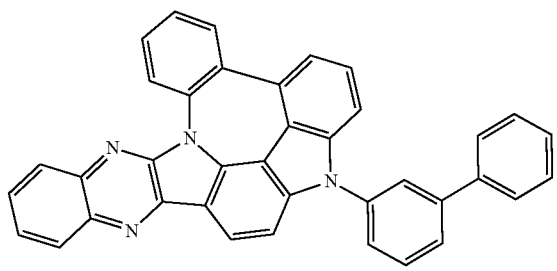
C-89
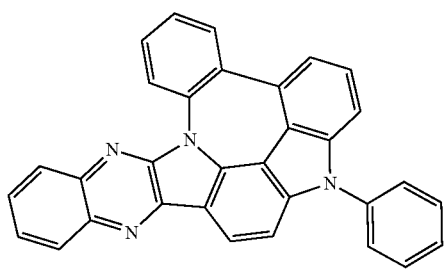
C-90
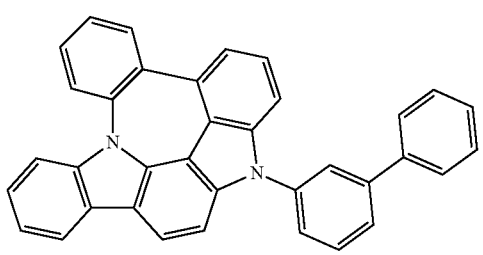

-continued
C-91
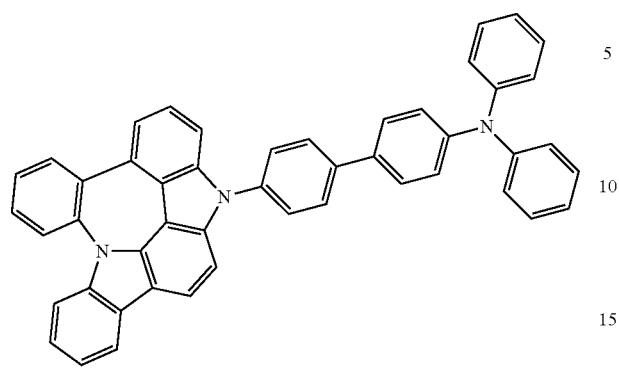
C-92
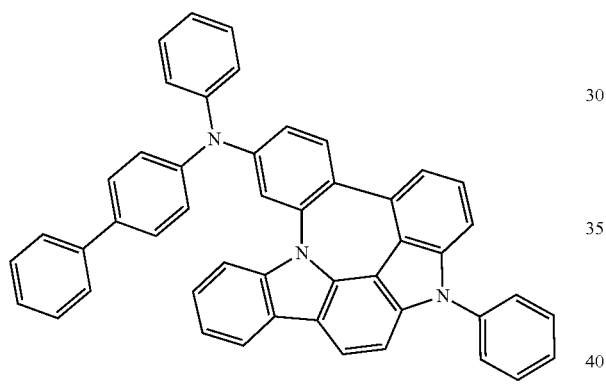
C-93
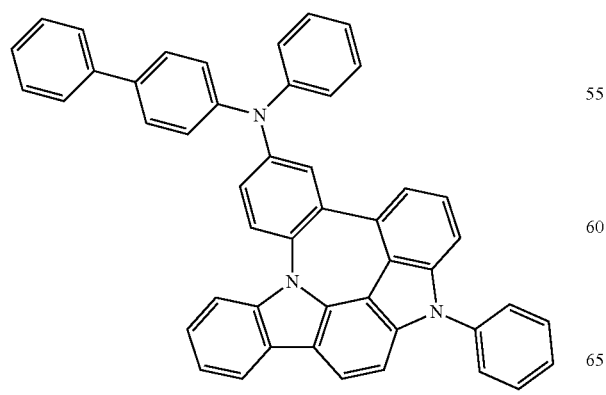
-continued
C-94
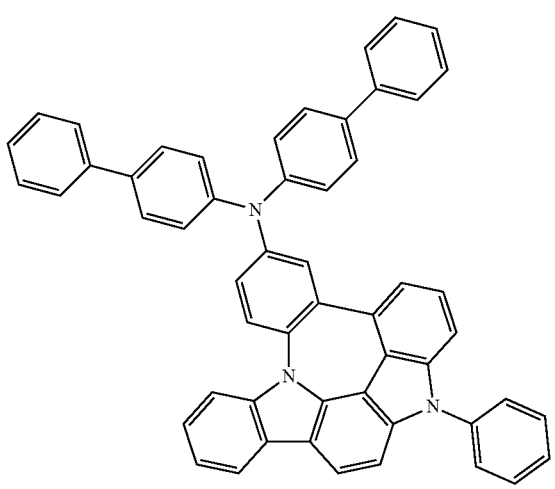
C-95
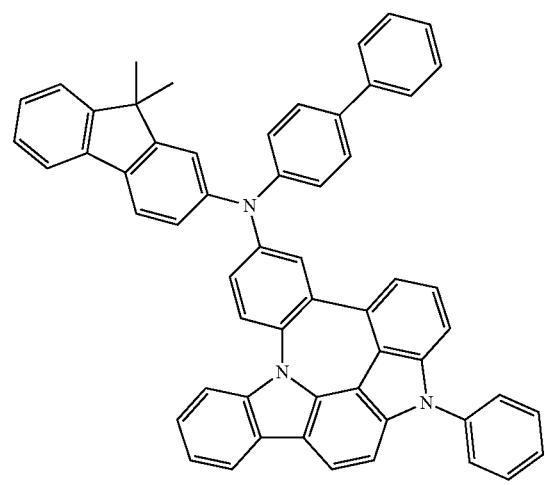
C-101
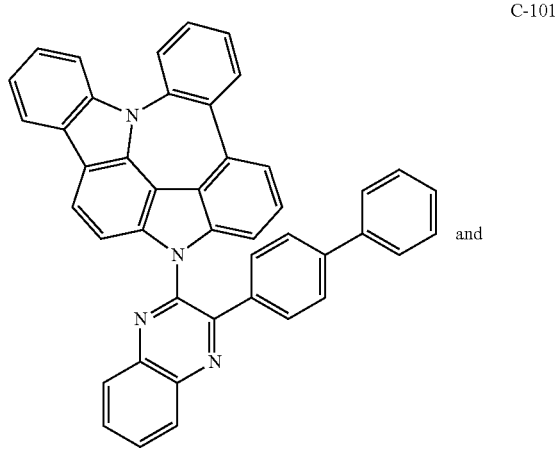
and C-102
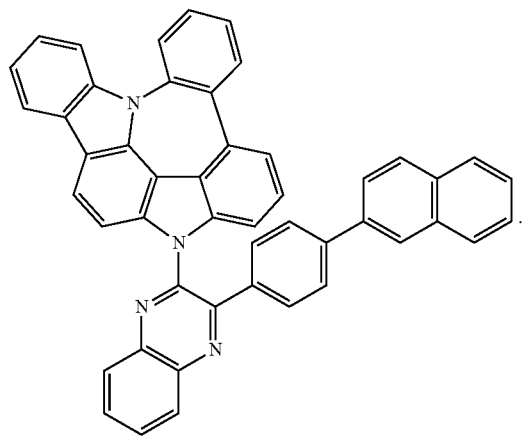
8. An organic electroluminescent material comprising the organic electroluminescent compound according to claim 1.
9. An organic electroluminescent device comprising the organic electroluminescent compound according to claim 1.
10. A display device comprising the organic electroluminescent compound according to claim 1.
* * * * *